US011358954B2

(12) United States Patent
Lagu et al.

(10) Patent No.: US 11,358,954 B2
(45) Date of Patent: Jun. 14, 2022

(54) PPAR AGONISTS, COMPOUNDS, PHARMACEUTICAL COMPOSITIONS, AND METHODS OF USE THEREOF

(71) Applicant: Mitobridge, Inc., Cambridge, MA (US)

(72) Inventors: Bharat Lagu, Acton, MA (US); Ramesh Senaiar, Hyderabad (IN)

(73) Assignee: Mitobridge, Inc., Cambridge, MA (US)

( * ) Notice: Subject to any disclaimer, the term of this patent is extended or adjusted under 35 U.S.C. 154(b) by 562 days.

(21) Appl. No.: 16/092,232

(22) PCT Filed: Apr. 13, 2017

(86) PCT No.: PCT/US2017/027327
§ 371 (c)(1),
(2) Date: Oct. 9, 2018

(87) PCT Pub. No.: WO2017/180818
PCT Pub. Date: Oct. 19, 2017

(65) Prior Publication Data
US 2020/0347037 A1 Nov. 5, 2020

Related U.S. Application Data

(60) Provisional application No. 62/322,017, filed on Apr. 13, 2016.

(51) Int. Cl.
| | | |
|---|---|---|
| C07D 405/10 | (2006.01) | |
| C07D 233/64 | (2006.01) | |
| C07D 233/68 | (2006.01) | |
| C07D 233/90 | (2006.01) | |

(52) U.S. Cl.
CPC ......... *C07D 405/10* (2013.01); *C07D 233/64* (2013.01); *C07D 233/68* (2013.01); *C07D 233/90* (2013.01)

(58) Field of Classification Search
CPC .. C07D 233/64; C07D 405/10; C07D 233/68; C07D 233/90
See application file for complete search history.

(56) References Cited

U.S. PATENT DOCUMENTS

| | | |
|---|---|---|
| 4,228,281 A | 10/1980 | Kainmuller et al. |
| 5,519,138 A | 5/1996 | Ries et al. |
| 6,054,457 A | 4/2000 | Setoi et al. |
| 9,938,234 B2 | 4/2018 | Evans et al. |
| 10,035,819 B2 | 7/2018 | Evans et al. |
| 10,399,958 B2 | 9/2019 | Downes et al. |
| 10,479,775 B1 | 11/2019 | Downes et al. |
| 2007/0054839 A1 | 3/2007 | Okamoto et al. |
| 2010/0063041 A1 | 3/2010 | Moon et al. |
| 2017/0305894 A1 | 10/2017 | Baiga et al. |
| 2018/0170857 A1 | 6/2018 | Evans et al. |
| 2018/0305403 A1 | 10/2018 | Evans et al. |
| 2020/0157074 A1 | 5/2020 | Downes et al. |
| 2021/0253549 A1 | 8/2021 | Downes et al. |
| 2021/0283116 A1* | 9/2021 | Lagu .................. A61K 31/4439 |

FOREIGN PATENT DOCUMENTS

| | | |
|---|---|---|
| AU | 2007252020 A1 | 11/2007 |
| CN | 101085772 A | 12/2007 |
| EP | 1553075 A1 | 7/2005 |
| EP | 2014652 A1 | 1/2009 |
| EP | 2128138 A1 | 12/2009 |
| JP | 2008-285452 A | 11/2008 |
| JP | 2009-525340 A | 7/2009 |
| WO | 2000/50391 A1 | 8/2000 |
| WO | 2001/12612 A1 | 2/2001 |
| WO | 2002/014285 A1 | 2/2002 |
| WO | 2004/020409 A1 | 3/2004 |
| WO | 2004/060367 A1 | 7/2004 |
| WO | 2006/027135 A1 | 3/2006 |
| WO | 2007/028424 A1 | 3/2007 |
| WO | 2007/030567 A2 | 3/2007 |
| WO | 2007/089857 A2 | 8/2007 |
| WO | 2007/110237 A2 | 10/2007 |
| WO | 2007/143951 A1 | 12/2007 |
| WO | 2009/086526 A2 | 7/2009 |
| WO | 2014/165827 A1 | 10/2014 |
| WO | 2015/035171 A1 | 3/2015 |
| WO | 2016/057322 A1 | 4/2016 |
| WO | 2016/057658 A1 | 4/2016 |
| WO | 2017/180818 A1 | 10/2017 |

OTHER PUBLICATIONS

Kadayat et al., "Targeting Peroxisome, etc.," Journal of Medicinal Chemistry, 63, 10109-10134. (Year: 2020).*
Takada et al., "Peroxisome, etc.," Expert Opinion on Therapeutic Patents, 30:1, 1-13. (Year: 2020).*
Miller, "Novel benefits, etc.," Curr Opin Lipidology, 24, pp. 233-238. (Year: 2013).*
Simone, Oncology: Introduction, Cecil Textbook of Medicine, ed. Bennett et al. W.B. Saunders CO. 20th ed. vol. 1, pp. 1004-1010. (Year: 1996).*
Gura, Systems for Identifiying New Drugs Are Often Faulty, Cancer Models, Science, vol. 278 No. 5340. pp 1041-1042. (Year: 1997).*
Johnson et al., Relationships between drug activity in NCI preclinical in vitro and in vivo and early clinical trials, British J of Cancer, 64(10): 1424-1431. (Year: 2001).*
Pearce et al., Failure modes in anticancer drug discovery and development, Cancer Drug Design and Discovery ed by Stephen Neidle, chap. 18, pp. 424-435. (Year: 2008).*
Schnegg et al., "Neuroprotective, etc.," PPAR Research, 6, Article ID373560, 1-10. (Year: 2011).*

(Continued)

*Primary Examiner* — Daniel R Carcanague
(74) *Attorney, Agent, or Firm* — McCarter & English, LLP; Steven G. Davis; Wei Song

(57) ABSTRACT

Provided herein are compounds and compositions useful in increasing PPARδ activity. The compounds and compositions provided herein are useful for the treatment of PPARδ related diseases (e.g., muscular diseases, vascular disease, demyelinating disease, and metabolic diseases).

18 Claims, No Drawings

(56) References Cited

OTHER PUBLICATIONS

Liu et al., "The Role of PPAR, etc.," International Journal if Molecular Sciences, 19, 3339, 1-14. (Year: 2018).*
Altinoz et al., "PPAR and its ligand, etc.," Molecular Aspects of Medicine 28 100871, 1-10. (Year: 2021).*
Arnold et al., Inflammatory monocytes recruited after skeletal muscle injury switch into antiinflammatory macrophages to support myogenesis. J Exp Med. May 14, 2007;204(5):1057-69.
Bräuer et al., Evolutionary chemistry approach toward finding novel inhibitors of the type 2 diabetes target glucose-6-phosphate translocase. J Comb Chem. Mar.-Apr. 2005;7(2):218-26.
Chemical Abstracts Plus, Accession No. 2000:737780, STN entry dated Oct. 19, 2000, and CAS Registry No. 312958-87-5.
Ciocoiu et al., Synthesis and dual PPARalpha/delta agonist effects of 1,4-disubstituted 1,2,3-triazole analogues of GW 501516. Eur J Med Chem. Jul. 2010;45(7):3047-55.
Ciocoiu et al., Synthesis, Biological Evaluation and Molecular Modeling of GW 501516 Analogues. Arch Pharm Chem Life Sci. 2010;10:612-624.
Ciocoiu et al., Synthesis, molecular modeling studies and biological evaluation of fluorine substituted analogs of GW 501516. Bioorg Med Chem. Dec. 1, 2011;19(23):6982-8.
Jacintho et al., Discovery of potent and seletive PPARalpha/delta dual antagonists and initial biological studies. Bioorganic & Medicinal Chemistry Letters. 6 pages, prepublication version, (2018).
Jonker et al., A PPARgamma-FGF1 axis is required for adaptive adipose remodelling and metabolic homeostasis. Nature. May 17, 2012;485(7398):391-4.
Kim et al., Synthesis and evaluation of an orally available "Y"-shaped biaryl peroxisome proliferator-activated receptor d agonist. Bioorg Med Chem. 8 pages, prepublication version, (2018).
Lagu et al., Highly selective perixisome proliferator-activated receptor delta (PPARdelta) modulator demonstrates improved safety profile to GW501516. Bioorganic & Medicinal Chemistry Letters. 2018;28:533-536.
Lagu et al., Novel highly selective peroxisome proliferator-activated receptor d (PPARd) modulators with pharmacokinetic properties suitable for once-daily oral dosing. Bioorg Med Chem Lett. Dec. 1, 2017;27(23):5230-5234.
Lagu et al., Selective PPARd Modulators Improve Mitochondrial Function: Potential Treatment for Duchenne Muscular Dystrophy (DMD). ACS Med Chem Lett. Jul. 31, 2018;9(9):935-940.
Lee et al., PPARdelta regulates glucose metabolism and insulin sensitivity. Proc Natl Acad Sci U S A. Feb. 28, 2006;103(9):3444-9.
Luquet et al., Peroxisome proliferator-activated receptor delta controls muscle development and oxidative capability. Faseb J. Dec. 2003;17(15):2299-301.
Markert et al., Exercise and Duchenne muscular dystrophy: toward evidence-based exercise prescription. Muscle Nerve. Apr. 2011;43(4):464-78.
Menetrey et al., Growth factors improve muscle healing in vivo. J Bone Joint Surg Br. Jan. 2000;82(1):131-7.
Mitachi et al., Synthesis and structure-activity relationship of disubstituted benzamides as a novel class of antimalarial agents. Bioorg Med Chem Lett. Jul. 15, 2012;22(14):4536-9.
Miura et al., Pharmacological activation of PPARbeta/delta stimulates utrophin A expression in skeletal muscle fibers and restores sarcolemmal integrity in mature mdx mice. Hum Mol Genet. Dec. 1, 2009;18(23):4640-9.
Narkar et al., AMPK and PPARdelta agonists are exercise mimetics. Cell. Aug. 8, 2008;134(3):405-15.
Naruhn et al., High-affinity peroxisome proliferator-activated receptor ß/d-specific ligands with pure antagonistic or inverse agonistic properties. Mol Pharmacol. Nov. 2011;80(5):828-38.
Pettersson et al., Design of a partial PPARdelta agonist. Bioorg Med Chem Lett. Aug. 15, 2007;17(16):4625-9.
Schwarz et al., Monitoring Solution Structures of Peroxisome Proliferator-Activated Receptor beta/d upon Ligand Binding. PLoS One. Mar. 18, 2016;11(3):e0151412. 20 pages.
Shefer et al., Reduced satellite cell numbers and myogenic capacity in aging can be alleviated by endurance axercise. PLoS One. Oct. 12, 2010;5(10):e13307. 11 pages.
Sobolevsky et al., Detection of PPARd agonists GW1516 and GW0742 and their metabolites in human urine. Drug Test Anal Oct. 2012;4(10):754-60.
Wang et al., Correction: Regulation of muscle fiber type and running endurance by PPARdelta. PLoS Biol. Jan. 2005;3(1):e61. 2 pages.
Wang et al., Peroxisome-proliferator-activated receptor delta activates fat metabolism to prevent obesity. Cell. Apr. 18, 2003;113(2):159-70.
Wang et al., Regulation of muscle fiber type and running endurance by PPARdelta. PLoS Biol. Oct. 2004;2(10):e294. 1532-1539.
Wu et al., Structural basis for specific ligation of the peroxisome proliferator-activated receptor d. Proc Natl Acad Sci U S A. Mar. 28, 2017;114(13):E2563-E2570.
Zhang et al., Discovery and SAR of para-alkylthiophenoxyacetic acids as potent and selective PPARdelta agonists. Bioorg Med Chem Lett. Feb. 15, 2009;19(4):1101-4.
International Preliminary Report on Patentability for Application No. PCT/US2015/054475, dated Apr. 20, 2017. 12 pages.
International Search Report and Written Opinion for Application No. PCT/US2014/033088, dated Jul. 22, 2014. 15 pages.
International Search Report and Written Opinion for Application No. PCT/US2016/055521, dated Jan. 2, 2017. 11 page.
International Search Report for Application No. PCT/US2015/054475, dated Dec. 15, 2015. 7 pages.
Singapore Office Action and Written Opinion for Application No. 11201802302S, dated Jan. 29, 2019, 9 pages.

* cited by examiner

PPAR AGONISTS, COMPOUNDS, PHARMACEUTICAL COMPOSITIONS, AND METHODS OF USE THEREOF

REFERENCE TO RELATED APPLICATIONS

This application is a U.S. national stage filing, under 35 U.S.C. § 371(c), of International Application No. PCT/US2017/027327, filed on Apr. 13, 2017, which claims the benefit of U.S. Provisional Application No. 62/322,017, filed Apr. 13, 2016. The entire contents of each of the aforementioned applications are incorporated herein by reference.

FIELD

This application concerns agonists of peroxisome proliferator-activated receptors (PPAR), particularly PPAR delta (PPARδ), and methods for their use, such as to treat or prevent one or more PPARδ-related diseases.

BACKGROUND

Peroxisome proliferator-activated receptor delta (PPARδ) is a nuclear receptor that is capable of regulating mitochondria biosynthesis. As shown in PCT/2014/033088, incorporated herein by reference, modulating the activity of PPARδ is useful for the treatment of diseases, developmental delays, and symptoms related to mitochondrial dysfunction, such as Alpers's Disease, MERRF-Myoclonic epilepsy and ragged-red fiber disease, Pearson Syndrome, and the like. Modulation PPARδ activity is effective in the treatment of other conditions, such as muscular diseases, demyelinating diseases, vascular diseases, and metabolic diseases. Indeed, PPARδ is an important biological target for compounds used to help treat and prevent mitochondrial diseases, muscle-related diseases and disorders, and other related conditions.

Accordingly, there remains a need in the art for novel compounds capable of effectively and reliably activating PPARδ in vitro and in vivo. There is also a need for PPARδ activating compounds with improved pharmacokinetic properties and improved metabolic stability. The present invention addresses these and other such needs.

SUMMARY

Provided herein, inter alia, are compounds and compositions comprising such compounds that are useful for increasing PPARδ activity. In particular, disclosed herein are methods modulating the activity of PPARδ for the treatment of diseases, developmental delays, and symptoms related to mitochondrial dysfunction (see, e.g., Example 1). For example, the disclosed compounds and compositions are useful in the treatment of mitochondrial diseases, such as Alpers's Disease, CPEO-Chronic progressive external ophthalmoplegia, Kearns-Sayra Syndrome (KSS), Leber Hereditary Optic Neuropathy (LHON), MELAS-Mitochondrial myopathy, encephalomyopathy, lactic acidosis, and stroke-like episodes, MERRF-Myoclonic epilepsy and ragged-red fiber disease, NARP-neurogenic muscle weakness, ataxia, and retinitis pigmentosa, and Pearson Syndrome. Alternatively, the disclosed compounds and compositions are useful in the treatment of other PPARδ-related diseases, such as muscular diseases, demyelinating diseases, vascular diseases, and metabolic diseases.

Moreover, the compounds disclosed herein possess certain advantages over similar compounds known in the art. In particular, the compounds disclosed herein only mildly inhibit, if at all, hERG activity, even at high concentrations. Further detail regarding the anti-hERG activity of the compounds disclosed herein is provided in Example 1a.

In one embodiment, provided herein is a compound of Formula (I):

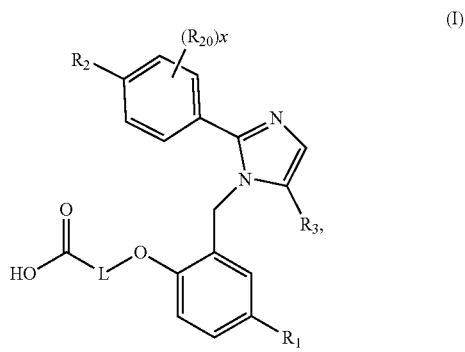

or a pharmaceutically acceptable salt thereof, wherein:

L is $(CH_2)_5$, which is optionally substituted by one methyl group;

$R^1$ is hydrogen, halogen, $C_1$-$C_4$-alkyl, $C_1$-$C_4$-haloalkyl, CN, $C_1$-$C_4$-alkoxy, $C_1$-$C_4$-haloalkoxy, or $C_3$-$C_6$-cycloalkyl;

$R^2$ is hydrogen, halogen, CN, $C_1$-$C_4$-alkyl, $C_1$-$C_4$-haloalkyl, $C_3$-$C_6$-cycloalkyl, $C_1$-$C_4$-alkoxy, $C_1$-$C_4$-haloalkoxy, $S(C_1$-$C_4$-alkyl), $SO_2(C_1$-$C_4$-alkyl), 5- or 6-membered heterocycle, aryl, 5-membered heteroaryl, $=\!\!-R^{2A}$, $O(CH_2)_m R^{2B}$, $NH(C_1$-$C_4$-alkyl), $N(C_1$-$C_4$-alkyl)$_2$, or $C(O)(C_1$-$C_4$-alkyl), wherein the aryl and the heteroaryl are optionally substituted with halogen, OH, CN, $C_1$-$C_4$-alkyl, formyl, acetyl, acetoxy, or carboxy, and wherein m is an integer having value of 1, 2, or 3;

x is an integer having a value of 0 or 1;

$R^{2A}$ and $R^{2B}$ are each independently $C_1$-$C_4$-alkyl, $C_1$-$C_4$-haloalkyl, or $C_3$-$C_6$-cycloalkyl;

$R^3$ is a $C_1$-$C_4$ haloalkyl, $-NO_2$, $-CN$, halogen, or $C(O)O(C_1$-$C_4$-alkyl); and each $R^{20}$ is independently halogen, $C_1$-$C_4$-alkyl, CN, or $C_1$-$C_4$-alkoxy.

Pharmaceutical compositions of the disclosed compounds also are disclosed herein. Particular embodiments comprise a pharmaceutically acceptable carrier or excipient and one or more of the disclosed compounds, or a pharmaceutically acceptable salt thereof. The pharmaceutical compositions of the invention can be used in therapy, e.g., for treating a PPARδ-related disease or condition in a subject.

Another embodiment comprises treating a PPARδ-related disease or condition in a subject by administering to the subject a therapeutically effective amount of one or more disclosed compounds, or a pharmaceutically acceptable salt thereof, or a pharmaceutical composition comprising the compound(s).

Also provided herein is the use of one or more of the disclosed compounds, or a pharmaceutically acceptable salt thereof, or a pharmaceutical composition comprising one or more of the disclosed compounds, for the preparation of a medicament for the treatment of a PPARδ-related disease or condition.

In another embodiment, provided herein the disclosed compounds, or a pharmaceutically acceptable salt thereof, or a pharmaceutical composition comprising one or more of the disclosed compounds for use in treating a PPARδ-related disease or condition.

DETAILED DESCRIPTION

Peroxisome proliferator-activated receptor delta (PPAR-δ), also known as peroxisome proliferator-activated receptor beta (PPAR-β) or as NR1C2 (nuclear receptor subfamily 1, group C, member 2), refers to a nuclear receptor protein that function as a transcription factor regulating the expression of genes. Ligands of PPARδ can promote myoblast proliferation after injury, such as injury to skeletal muscle. PPARδ (OMIM 600409) sequences are publically available, for example from GenBank® sequence database (e.g., accession numbers NP_001165289.1 (human, protein) NP_035275 (mouse, protein), NM_001171818 (human, nucleic acid) and NM_011145 (mouse, nucleic acid)).

Herein, the phrase "PPARδ agonist" refers to substances that increase the activity of PPARδ. Substances can be tested for their PPARδ agonist activity by contacting the substance with cells expressing PPARδ, detecting their binding with PPARδ and then detecting signals that serve as the indicator of the activation of PPARδ. See, for example, Example 1a.

Definitions

The term "alkyl" used alone or as part of a larger moiety, such as "alkoxy", "haloalkyl", "haloalkoxy", "cycloalkyl", and the like, means saturated aliphatic straight-chain or branched monovalent hydrocarbon radical. Unless otherwise specified, an alkyl group typically has 1 to 4 carbon atoms, i.e., $C_1$-$C_4$-alkyl. As used herein, a "$C_1$-$C_4$-alkyl" group means a radical having from 1 to 4 carbon atoms in a linear or branched arrangement, and includes methyl, ethyl, propyl, isopropyl, butyl, isobutyl, sec-butyl and tert-butyl.

"Alkoxy" means an alkyl radical attached through an oxygen linking atom, represented by —O-alkyl. For example, "$C_1$-$C_4$-alkoxy" includes methoxy, ethoxy, propoxy, isopropoxy, and butoxy.

The terms "haloalkyl" and "haloalkoxy" mean alkyl or alkoxy, as the case may be, substituted with one or more halogen atoms. For example, "$C_1$-$C_4$-haloalkyl" includes fluoromethyl, difluoromethyl, trifluoromethyl, chloromethyl, dichloromethyl, bromomethyl, fluoroethyl, difluoroethyl, dichloroethyl and chloropropyl, and "$C_1$-$C_4$-haloalkoxy" includes fluoromethoxy, difluoromethoxy, trifluoromethoxy, chloromethoxy, dichloromethoxy, bromomethoxy, fluoroethoxy, difluoroethoxy, dichloroethoxy and chloropropoxy.

The term "halogen" means fluorine or fluoro (F), chlorine or chloro (Cl), bromine or bromo (Br), or iodine or iodo (I).

"Aryl" refers to a carbocyclic aromatic group. Examples of "aryl" include phenyl, naphthyl, anthracenyl, 1,2-dihydronaphthyl, 1,2,3,4-tetrahydronaphthyl, fluorenyl, indanyl and indenyl.

"Cycloalkyl" means a 3-6 membered saturated aliphatic cyclic hydrocarbon radical.

It can be monocyclic, bicyclic (e.g., a bridged or fused bicyclic ring), or tricyclic. For example, monocyclic $C_3$-$C_6$-cycloalkyl means a radical having from 3 to 6 carbon atoms arranged in a monocyclic ring. For example, "$C_3$-$C_6$-cycloalkyl" includes, but is not limited to, cyclopropyl, cyclobutyl, cyclopentyl, and cyclohexyl.

"5- or 6-membered heterocycle" means a nonaromatic radical having from 5 or 6 ring atoms (including 1 to 3 ring heteroatoms) arranged in a monocyclic ring. Examples of "5- or 6-membered heterocycle" include, but are not limited to, morpholinyl, thiomorpholinyl, pyrrolidinonyl, pyrrolidinyl, piperidinyl, piperazinyl, hydantoinyl, valerolactamyl, dihydroimidazole, dihydrofuranyl, dihydropyranyl, dihydropyridinyl, dihydropyrimidinyl, dihydrothienyl, dihydrothiophenyl, dihydrothiopyranyl, tetrahydroimidazole, tetrahydrofuranyl, tetrahydropyranyl, tetrahydrothienyl, tetrahydropyridinyl, tetrahydropyrimidinyl, tetrahydrothiophenyl, and tetrahydrothiopyranyl.

"5-membered heteroaryl" means a monocyclic aromatic ring system having five ring atoms selected from carbon and at least one (typically 1 to 3, more typically 1 or 2) ring heteroatoms (e.g., oxygen, nitrogen or sulfur). Typical examples are 5-membered heteroaryl containing 1 or 2 atoms selected independently from nitrogen atoms, sulfur atoms and oxygen atoms such as pyrrolyl, thienyl, furyl, imidazolyl, pyrazolyl, isothiazolyl, isoxazolyl, and the like.

If a group is described as being "substituted", a non-hydrogen substituent is in the place of a hydrogen on a carbon, sulfur or nitrogen of the group. Thus, for example, a substituted alkyl is an alkyl wherein at least one non-hydrogen substituent is in the place of a hydrogen on the alkyl. To illustrate, monofluoroalkyl is alkyl substituted with a fluoro substituent, and difluoroalkyl is alkyl substituted with two fluoro substituents. It should be recognized that if there is more than one substitution on a group, each non-hydrogen substituent can be identical or different (unless otherwise stated).

Compounds having one or more chiral centers can exist in various stereoisomeric forms. Stereoisomers are compounds that differ only in their spatial arrangement. Stereoisomers include all diastereomeric, enantiomeric, and epimeric forms as well as racemates and mixtures thereof. The term "geometric isomer" refers to compounds having at least one double bond, wherein the double bond(s) may exist in cis (also referred to as syn or entgegen (E)) or trans (also referred to as anti or zusammen (Z)) forms as well as mixtures thereof. When a disclosed compound is named or depicted by structure without indicating stereochemistry, it is understood that the name or the structure encompasses one or more of the possible stereoisomers, or geometric isomers, or a mixture of the encompassed stereoisomers or geometric isomers.

When a geometric isomer or a stereoisomer is depicted by name or structure, it is to be understood that the named or depicted isomer exists to a greater degree than another isomer, that is that the geometric isomeric purity of the named or depicted geometric isomer is greater than 50%, such as at least 60%, 70%, 80%, 90%, 99% or 99.9% pure by weight. Geometric isomeric purity is determined by dividing the weight of the named or depicted geometric isomer in the mixture by the total weight of all of the geomeric isomers in the mixture.

Racemic mixture means 50% of one enantiomer and 50% of is corresponding enantiomer. When a compound with one chiral center is named or depicted without indicating the stereochemistry of the chiral center, it is understood that the name or structure encompasses both enantiomerically-pure, enantiomerically-enriched or racemic forms of the compound. When a compound with two or more chiral centers is named or depicted without indicating the stereochemistry of the chiral centers, it is understood that the name or structure encompasses all possible diasteriomeric forms (e.g., diastereomerically pure, diastereomerically enriched and equimolar mixtures of one or more diastereomers (e.g., racemic mixtures) of the compound.

Enantiomeric and diastereomeric mixtures can be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and diastereomers also can be obtained from diastereomerically- or enantiomerically-pure intermediates, reagents, and catalysts by well-known asymmetric synthetic methods.

When a compound is designated by a name or structure that indicates a single enantiomer, unless indicated otherwise, the compound is at least 60%, 70%, 80%, 90%, 99% or 99.9% optically pure (also referred to as "enantiomerically pure"). Optical purity is the weight in the mixture of the named or depicted enantiomer divided by the total weight in the mixture of both enantiomers.

When the stereochemistry of a disclosed compound is named or depicted by structure, and the named or depicted structure encompasses more than one stereoisomer (e.g., as in a diastereomeric pair), it is to be understood that one of the encompassed stereoisomers or any mixture of the encompassed stereoisomers is included. It is to be further understood that the stereoisomeric purity of the named or depicted stereoisomers at least 60%, 70%, 80%, 90%, 99% or 99.9% by weight. The stereoisomeric purity in this case is determined by dividing the total weight in the mixture of the stereoisomers encompassed by the name or structure by the total weight in the mixture of all of the stereoisomers.

Included in the present teachings are pharmaceutically acceptable salts of the compounds disclosed herein. The disclosed compounds have basic amine groups and therefore can form pharmaceutically acceptable salts with pharmaceutically acceptable acid(s). Suitable pharmaceutically acceptable acid addition salts of the compounds described herein include salts of inorganic acids (such as hydrochloric acid, hydrobromic, phosphoric, nitric, and sulfuric acids) and of organic acids (such as, e.g., acetic acid, benzenesulfonic, benzoic, methanesulfonic, and p-toluenesulfonic acids). The disclosed compounds have a carbocyclic group and therefore can form pharmaceutically acceptable salts with pharmaceutically acceptable acid(s). Compounds of the present teachings with acidic groups such as carboxylic acids can form pharmaceutically acceptable salts with pharmaceutically acceptable base(s). Suitable pharmaceutically acceptable basic salts include ammonium salts, alkali metal salts (such as sodium and potassium salts) and alkaline earth metal salts (such as magnesium and calcium salts).

As used herein, the term "pharmaceutically-acceptable salt" refers to pharmaceutical salts that are, within the scope of sound medical judgment, suitable for use in contact with the tissues of humans and lower animals without undue toxicity, irritation, and allergic response, and are commensurate with a reasonable benefit/risk ratio. Pharmaceutically-acceptable salts are well known in the art. For example, S. M. Berge, et al. describes pharmacologically acceptable salts in *J. Pharm. Sci.*, 1977, 66:1-19.

The neutral forms of the compounds of the invention are regenerated from their corresponding salts by contacting the salt with a base or acid and isolating the parent compound in the conventional manner. The parent form of the compound may differ from the various salt forms in certain physical properties, such as solubility in polar solvents. The neutral forms of compounds disclosed herein also are included in the invention.

The terms "administer", "administering", "administration", and the like, as used herein, refer to methods that may be used to enable delivery of compositions to the desired site of biological action. These methods include, but are not limited to, intraarticular (in the joints), intravenous, intramuscular, intratumoral, intradermal, intraperitoneal, subcutaneous, orally, topically, intrathecally, inhalationally, transdermally, rectally, and the like. Administration techniques that can be employed with the agents and methods described herein are found in e.g., Goodman and Gilman, The Pharmacological Basis of Therapeutics, current ed.; Pergamon; and Remington's, Pharmaceutical Sciences (current edition), Mack Publishing Co., Easton, Pa.

As used herein, the terms "co-administration", "administered in combination with", and their grammatical equivalents, are meant to encompass administration of two or more therapeutic agents to a single subject, and are intended to include treatment regimens in which the agents are administered by the same or different route of administration or at the same or different times. In some embodiments the one or more compounds described herein will be co-administered with other agents. These terms encompass administration of two or more agents to the subject so that both agents and/or their metabolites are present in the subject at the same time. They include simultaneous administration in separate compositions, administration at different times in separate compositions, and/or administration in a composition in which both agents are present. Thus, in some embodiments, the compounds described herein and the other agent(s) are administered in a single composition. In some embodiments, the compounds described herein and the other agent(s) are admixed in the composition.

Generally, an effective amount of a compound taught herein varies depending upon various factors, such as the given drug or compound, the pharmaceutical formulation, the route of administration, the type of disease or disorder, the identity of the subject or host being treated, and the like, but can nevertheless be routinely determined by one skilled in the art. An effective amount of a compound of the present teachings may be readily determined by one of ordinary skill by routine methods known in the art.

The term "effective amount" or "therapeutically effective amount" means an amount when administered to the subject which results in beneficial or desired results, including clinical results, e.g., inhibits, suppresses or reduces the symptoms of the condition being treated in the subject as compared to a control. For example, a therapeutically effective amount can be given in unit dosage form (e.g., from 1 mg to about 50 g per day, e.g., from 1 mg to about 5 grams per day).

The particular mode of administration and the dosage regimen will be selected by the attending clinician, taking into account the particulars of the case (e.g., the subject, the disease, the disease state involved, the particular treatment, and whether the treatment is prophylactic). Treatment can involve daily or multi-daily or less than daily (such as weekly or monthly etc.) doses over a period of a few days to months, or even years. However, a person of ordinary skill in the art would immediately recognize appropriate and/or equivalent doses looking at dosages of approved compositions for treating a PPARδ related disease using the disclosed PPAR agonists for guidance.

A "subject" is a mammal, preferably a human, but can also be an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

"Pharmaceutically acceptable excipient" and "pharmaceutically acceptable carrier" refer to a substances that aid the formulation and/or administration of an active agent to and/or absorption by a subject and can be included in the compositions of the present disclosure without causing a significant adverse toxicological effect on the subject. Non-limiting examples of pharmaceutically acceptable carriers and excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with or interfere with the activity of the compounds provided herein. One of ordinary skill in the art will recognize that other pharmaceutical carriers and excipients are suitable for use with disclosed compounds.

Compounds of the Invention

Disclosed herein are embodiments of a compound having general Formula (I): compound of Formula (I):

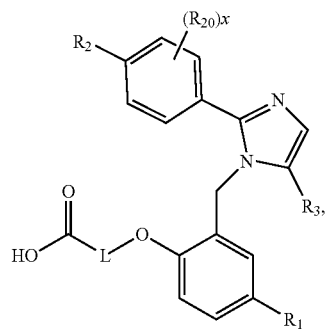
(I)

or a pharmaceutically acceptable salt thereof, wherein:

L is $(CH_2)_5$, which is optionally substituted by one methyl group;

$R^1$ is hydrogen, halogen, $C_1$-$C_4$-alkyl, $C_1$-$C_4$-haloalkyl, CN, $C_1$-$C_4$-alkoxy, $C_1$-$C_4$-haloalkoxy, or $C_3$-$C_6$-cycloalkyl;

$R^2$ is hydrogen, halogen, CN, $C_1$-$C_4$-alkyl, $C_1$-$C_4$-haloalkyl, $C_3$-$C_6$-cycloalkyl, $C_1$-$C_4$-alkoxy, $C_1$-$C_4$-haloalkoxy, $S(C_1$-$C_4$-alkyl), $SO_2(C_1$-$C_4$-alkyl), 5- or 6-membered heterocycle, aryl, 5-membered heteroaryl, =—$R^{2A}$, $O(CH_2)_m R^{2B} NH(C_1$-$C_4$-alkyl), $N(C_1$-$C_4$-alkyl)$_2$, or $C(O)(C_1$-$C_4$-alkyl), wherein the aryl and the heteroaryl are optionally substituted with halogen, OH, CN, $C_1$-$C_4$-alkyl, formyl, acetyl, acetoxy, or carboxy, and wherein m is an integer having value of 1, 2, or 3;

x is an integer having a value of 0 or 1;

$R^{2A}$ and $R^{2B}$ are each independently $C_1$-$C_4$-alkyl, $C_1$-$C_4$-haloalkyl, or $C_3$-$C_6$-cycloalkyl;

$R^3$ is a $C_1$-$C_4$ haloalkyl, —$NO_2$, —CN, halogen, or $C(O)O(C_1$-$C_4$-alkyl); and each $R^{20}$ is independently halogen, $C_1$-$C_4$-alkyl, CN, or $C_1$-$C_4$-alkoxy.

In a 1$^{st}$ embodiment, the compound has the structure of Formulas (Ia) or (Ib):

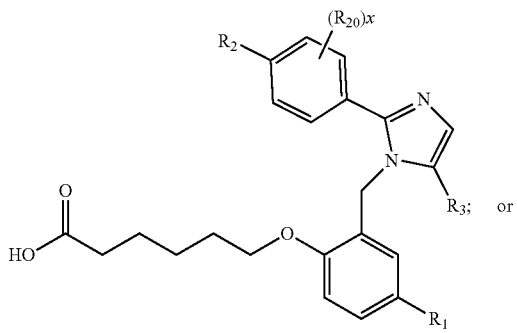
(Ia)

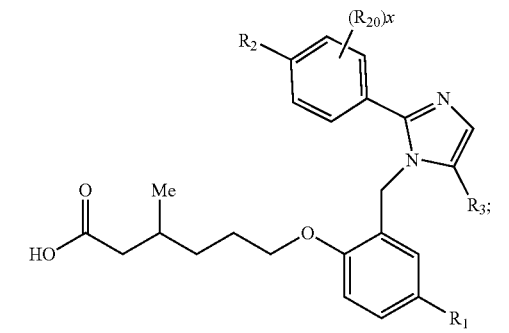
(Ib)

or a pharmaceutically acceptable salt thereof, wherein the variables are as defined for Formula (I).

In a 2$^{nd}$ embodiment, the compound has the structure of Formula (Ibb)

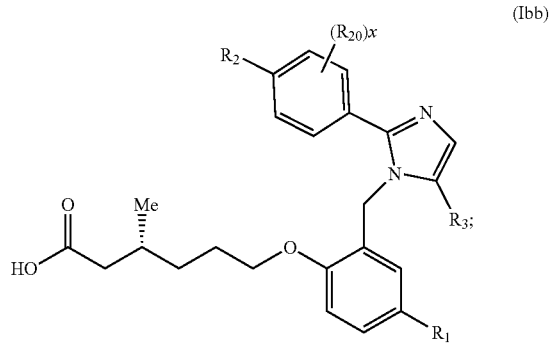
(Ibb)

or a pharmaceutically acceptable salt thereof, wherein the variables are as defined for Formula (I).

In a 3$^{rd}$ embodiment, the compound has the structure of Formulas (I), (Ia), (Ib), or (Ibb), wherein $R^3$ is halomethyl, CN or halogen; and the remainder of the variables are as defined for Formula (I) or as defined in the 1$^{st}$ embodiment.

In a 4$^{th}$ embodiment, the compound has the structure of the compound has the structure of Formulas (I), (Ia), (Ib), or (Ibb), wherein $R^3$ is $CF_3$, Cl or CN; and the remainder of the variables are as defined for Formula (I) or as defined in the 1$^{st}$ embodiment.

In a 5$^{th}$ embodiment, the compound has the structure of the compound has the structure of Formulas (I), (Ia), (Ib), or (Ibb), wherein $R^2$ is hydrogen, halogen, CN, $C_1$-$C_4$-alkyl, $C_1$-$C_4$ alkoxy, $C_1$-$C_4$-haloalkyl, $C_1$-$C_4$-haloalkoxy, $S(C_1$-$C_4$-alkyl), or furanyl, wherein the furanyl can be optionally substituted with $C_1$-$C_4$-alkyl; and x is 0 or 1; and the remainder of the variables are as defined for Formula Formula (I) or as defined in the $1^{st}$, $2^{nd}$, $3_{rd}$, or $4^{th}$ embodiment.

In a $6^{th}$ embodiment, the compound has the structure of the compound has the structure of Formulas (I), (Ia), (Ib), or (Ibb), wherein $R^2$ is H, halogen, CN, $CH_3$, halomethyl, halomethoxy, methoxy or furanyl, wherein the furanyl can be optionally substituted with $CH_3$; and $R^{20}$ is methyl or halogen; and the remainder of the variables are as defined in the $5^{th}$ embodiment.

In a $7^{th}$ embodiment, the compound has the structure of the compound has the structure of Formulas (I), (Ia), (Ib), or (Ibb), wherein $R^2$ is H, F, Cl, CN, $CF_3$, $OCF_3$ or furanyl; and x is 0; and the remainder of the variables are as defined in the $6^{th}$ embodiment.

In a $8^{th}$ embodiment, the compound has the structure of the compound has the structure of Formulas (I), (Ia), (Ib), or (Ibb), $R^1$ is hydrogen; and the remainder of the variables are as defined for Formula (I) or as defined in the 1, $2^{nd}$, $3^{rd}$, $4^{th}$, $5^{th}$, $6^{th}$, or $7^{th}$ embodiment.

In a $9^{th}$ embodiment, the compound has the structure of the compound has the structure of Formulas (I), (Ia), (Ib), or (Ibb), $R^1$ is hydrogen or fluoro; and the remainder of the variables are as defined for Formula (I) or as defined in the $1^{st}$, $2^{nd}$, $3^{rd}$, $4^{th}$, $5^{th}$, $6^{th}$, $7^{th}$, or $8^{th}$ embodiment.

In certain embodiments, the invention is any one of the compounds depicted in the exemplification section of the instant application; pharmaceutically acceptable salts as well as the neutral forms of these compounds also are included in the invention. Specifically, the invention is any one of the compounds depicted in Examples 2A-2I; pharmaceutically acceptable salts as well as the neutral forms of these compounds also are included in the invention. In preferred embodiments, the invention is any one of Compounds 2a-2i; pharmaceutically acceptable salts as well as the neutral forms of these compounds also are included in the invention.

Methods of Preparing Compounds of the Invention

Methods of preparing compounds of Formulas (I), (Ia), and (Ib) are disclosed. In general, a compound of Formula (I) may be prepared by reacting a compound of Formula (II):

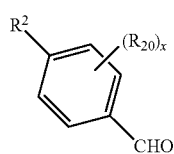

(II)

with ethane-1,2-diamine to afford a compound of Formula (III):

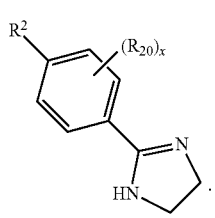

(III)

The compound of Formula (III) can be subjected oxidative conditions to afford a compound of Formula (IV):

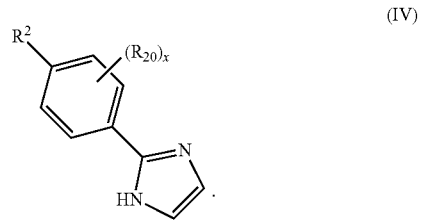

(IV)

The compound of Formula (IV) then can be reacted with 2-methoxy-5-($R^1$)-benzylbromide to afford a compound of Formula (V):

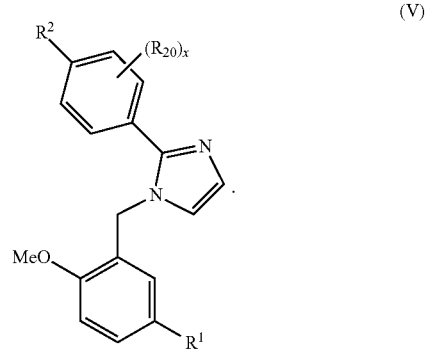

(V)

The compound of Formula (V) can be reacted with N-iodosuccinimide (NIS) to afford a compound of formula (VI):

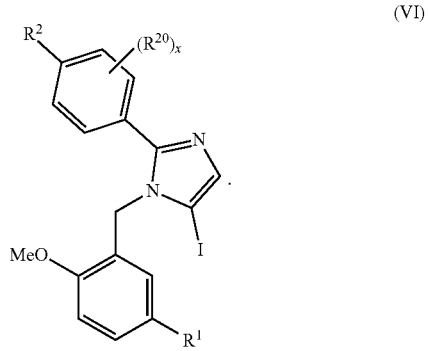

(VI)

Subsequently, the compound of Formula (VI) may be reacted with $R^3$—$X^a$, wherein $X^a$ is a leaving group, to afford the compound of Formula (VII):

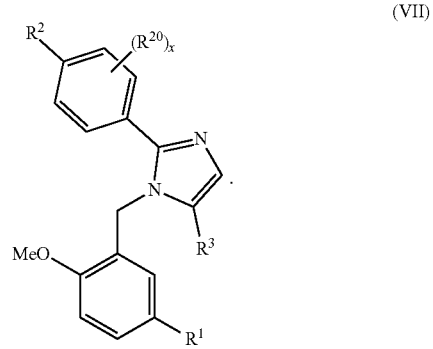

(VII)

The compound of Formula (VII) then can be subjected to O-demethylation conditions to form a compound of Formula (VIII):

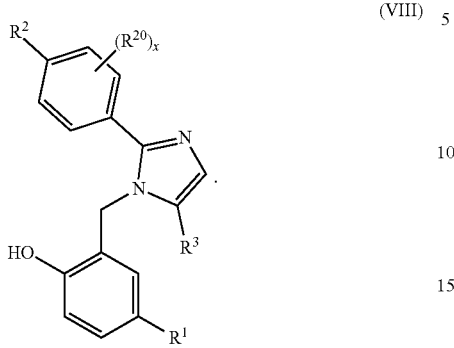
(VIII)

Subsequently, the compound of (VIII) may be reacted with a compound of Formula EtOCO-L-Br (IX) to afford a compound of Formula (X):

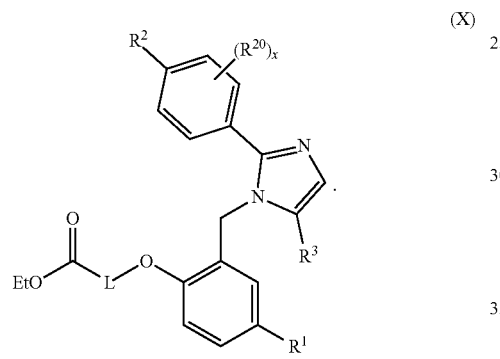
(X)

Finally, the compound of Formula (X) may be subjected to hydrolysis conditions to form a compound of Formula (I).

Similarly, a compound of Formula (Ia) may be prepared by reacting a compound of Formula (VIII) with ethyl 6-bromo-3-hexanoate to afford a compound of Formula (Xa):

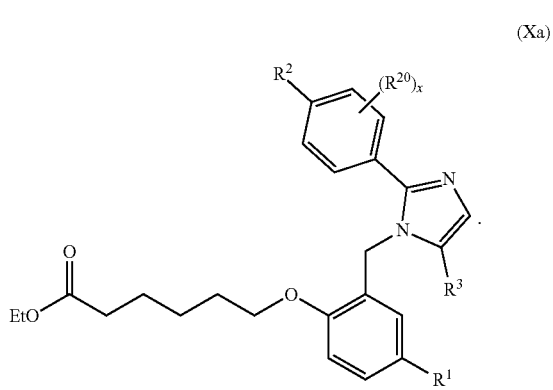
(Xa)

Subsequent hydrolysis of the compound of Formula (Xa) affords the compound of Formula (Ia).

Similarly, a compound of Formula (Ib) may be prepared by reacting a compound of Formula (VIII) with ethyl 6-bromo-3-methylhexanoate to afford a compound of Formula (Xb):

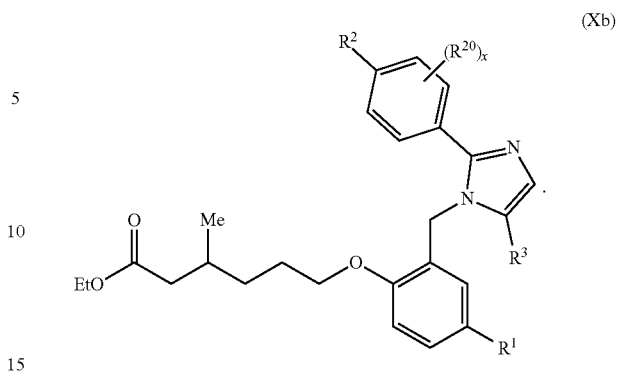
(Xb)

Subsequent hydrolysis of the compound of Formula (Xb) affords the compound of Formula (Ib).

Similarly, a compound of Formula (Ibb) may be prepared by reacting a compound of Formula (VIII) with ethyl (R)-6-bromo-3-methylhexanoate to afford a compound of Formula (Xbb):

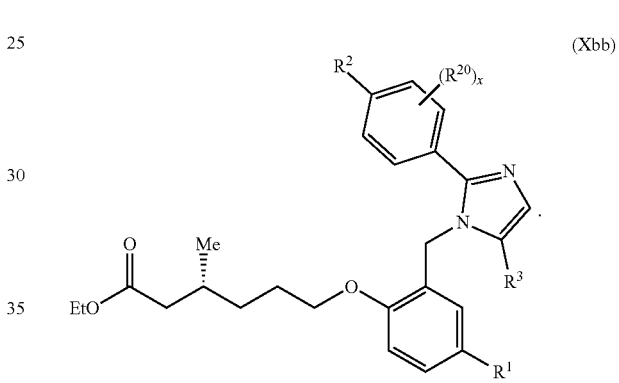
(Xbb)

Subsequent hydrolysis of the compound of Formula (Xbb) affords the compound of Formula (Ibb).

Detailed synthetic protocols for preparing exemplary compounds of Formulas (I), (Ia), (Ib), and (Ibb) are presented in Examples 2A-2I.

Methods of Treatment

Methods of treating a PPARδ-related disease or condition in a subject are disclosed. The methods can include administering to the subject a therapeutically effective amount of one or more compounds or compositions provided herein.

In one embodiment, the PPARδ-related disease is a mitochondrial disease. Examples of mitochondrial diseases include, but are not limited to, Alpers's Disease, CPEO-Chronic progressive external ophthalmoplegia, Kearns-Sayra Syndrome (KSS), Leber Hereditary Optic Neuropathy (LHON), MELAS-Mitochondrial myopathy, encephalomyopathy, lactic acidosis, and stroke-like episodes, MERRF-Myoclonic epilepsy and ragged-red fiber disease, NARP-neurogenic muscle weakness, ataxia, and retinitis pigmentosa, and Pearson Syndrome.

In other embodiments, the PPARδ-related disease is a vascular disease (such as a cardiovascular disease or any disease that would benefit from increasing vascularization in tissues exhibiting impaired or inadequate blood flow). In other embodiments, the PPARδ-related disease is a muscular disease, such as a muscular dystrophy. Examples of muscular dystrophy include but are not limited to Duchenne muscular dystrophy, Becker muscular dystrophy, limb-girdle muscular dystrophy, congenital muscular dystrophy, facioscapulohumeral muscular dystrophy, myotonic muscular dystrophy, oculopharyngeal muscular dystrophy, distal muscular dystrophy, and Emery-Dreifuss muscular dystrophy.

In some embodiments, the PPARδ-related disease or condition is a demyelinating disease, such as multiple sclerosis, Charcot-Marie-Tooth disease, Pelizaeus-Merzbacher disease, encephalomyelitis, neuromyelitis optica, adrenoleukodystrophy, or Guillian-Barre syndrome.

In other embodiments, the PPARδ-related disease is a metabolic disease. Examples of metabolic diseases include but are not limited to obesity, hypertriglyceridemia, hyperlipidemia, hypoalphalipoproteinemia, hypercholesterolemia, dyslipidemia, Syndrome X, and Type II diabetes mellitus.

In yet other embodiments, the PPARδ-related disease is a muscle structure disorder. Examples of a muscle structure disorders include, but are not limited to, Bethlem myopathy, central core disease, congenital fiber type disproportion, distal muscular dystrophy (MD), Duchenne & Becker MD, Emery-Dreifuss MD, facioscapulohumeral MD, hyaline body myopathy, limb-girdle MD, a muscle sodium channel disorders, myotonic chondrodystrophy, myotonic dystrophy, myotubular myopathy, nemaline body disease, oculopharyngeal MD, and stress urinary incontinence.

In still other embodiments, the PPARδ-related disease is a neuronal activation disorder, Examples of neuronal activation disorders include, but are not limited to, amyotrophic lateral sclerosis, Charcot-Marie-Tooth disease, Guillain-Barre syndrome, Lambert-Eaton syndrome, multiple sclerosis, myasthenia gravis, nerve lesion, peripheral neuropathy, spinal muscular atrophy, tardy ulnar nerve palsy, and toxic myoneural disorder.

In other embodiments, the PPARδ-related disease is a muscle fatigue disorder. Examples of muscle fatigue disorders include, but are not limited to chronic fatigue syndrome, diabetes (type I or II), glycogen storage disease, fibromyalgia, Friedreich's ataxia, intermittent claudication, lipid storage myopathy, MELAS, mucopolysaccharidosis, Pompe disease, and thyrotoxic myopathy.

In some embodiments, the PPARδ-related disease is a muscle mass disorder. Examples of muscle mass disorders include, but are not limited to, cachexia, cartilage degeneration, cerebral palsy, compartment syndrome, critical illness myopathy, inclusion body myositis, muscular atrophy (disuse), sarcopenia, steroid myopathy, and systemic lupus erythematosus.

In other embodiments, the PPARδ-related disease is a beta oxidation disease. Examples of beta oxidation diseases include, but are not limited to, systemic carnitine transporter, carnitine palmitoyltransferase (CPT) II deficiency, very long—chain acyl—CoA dehydrogenase (LCHAD or VLCAD) deficiency, trifunctional enzyme deficiency, medium-chain acyl—CoA dehydrogenase (MCAD) deficiency, short—chain acyl—CoA dehydrogenase (SCAD) deficiency, and riboflavin—responsive disorders of β-oxidation (RR-MADD).

In some embodiments, the PPARδ-related disease is a vascular disease. Examples of vascular diseases include, but are not limited to, peripheral vascular insufficiency, peripheral vascular disease, intermittent claudication, peripheral vascular disease (PVD), peripheral artery disease (PAD), peripheral artery occlusive disease (PAOD), and peripheral obliterative arteriopathy.

In other embodiments, the PPARδ-related disease is an ocular vascular disease. Examples of ocular vascular diseases include, but are not limited to, age-related macular degeneration (AMD), stargardt disease, hypertensive retinopathy, diabetic retinopathy, retinopathy, macular degeneration, retinal haemorrhage, and glaucoma.

In yet other embodiments, the PPARδ-related disease is a muscular eye disease. Examples of muscular eye diseases include, but are not limited to, strabismus (crossed eye/wandering eye/walleye ophthalmoparesis), progressive external ophthalmoplegia, esotropia, exotropia, a disorder of refraction and accommodation, hypermetropia, myopia, astigmatism, anisometropia, presbyopia, a disorders of accommodation, or internal ophthalmoplegia.

In yet other embodiments, the PPARδ-related disease is a metabolic disease. Examples of metabolic disorders include, but are not limited to, hyperlipidemia, dyslipidemia, hyperchlolesterolemia, hypertriglyceridemia, HDL hypocholesterolemia, LDL hypercholesterolemia and/or HLD non-cholesterolemia, VLDL hyperproteinemia, dyslipoproteinemia, apolipoprotein A-I hypoproteinemia, atherosclerosis, disease of arterial sclerosis, disease of cardiovascular systems, cerebrovascular disease, peripheral circulatory disease, metabolic syndrome, syndrome X, obesity, diabetes (type I or II), hyperglycemia, insulin resistance, impaired glucose tolerance, hyperinsulinism, diabetic complication, cardiac insufficiency, cardiac infarction, cardiomyopathy, hypertension, non-alcoholic fatty liver disease (NAFLD), nonalcoholic steatohepatitis (NASH), thrombus, Alzheimer disease, neurodegenerative disease, demyelinating disease, multiple sclerosis, adrenal leukodystrophy, dermatitis, psoriasis, acne, skin aging, trichosis, inflammation, arthritis, asthma, hypersensitive intestine syndrome, ulcerative colitis, Crohn's disease, and pancreatitis.

In still other embodiments, the PPARδ-related disease is cancer. Examples of cancer include, but are not limited to, cancers of the colon, large intestine, skin, breast, prostate, ovary, and/or lung.

In other embodiments, the PPARδ-related disease is a renal disease. Examples of renal diseases include, but are not limited to, glomerulonephritis, glomerulosclerosis, nephrotic syndrome, hypertensive nephrosclerosis, acute nephritis, recurrent hematuria, persistent hematuria, chronic nephritis, rapidly progressive nephritis, acute renal failure, chronic renal failure, diabetic nephropathy, or Bartter's syndrome. PCT/US2014/033088, incorporated herein by reference, demonstrates genetic and pharmacological activation of PPARδ promotes muscle regeneration in an acute thermal injury mouse model. Accordingly, use of PPARδ as a therapeutic target to enhance regenerative efficiency of skeletal muscle is also provided.

Pharmaceutical Compositions and Administration Thereof
Additional Therapeutic Agents Pharmaceutical compositions are disclosed that include one or more compounds provided herein (such as 1, 2, 3, 4 or 5 of such compounds), and typically at least one additional substance, such as an excipient, a known therapeutic other than those of the present disclosure, and combinations thereof. In some embodiments, the disclosed PPAR agonists can be used in combination with other agents known to have beneficial activity with the disclosed PPAR agonists. For example, disclosed compounds can be administered alone or in combination with: one or more other PPAR agonists, such as a thiazolidinedione, including rosiglitazone, pioglitazone, troglitazone, and combinations thereof, or a sulfonylurea agent or a pharmaceutically acceptable salt thereof, such as tolbutamide, tolazamide, glipizide, carbutamide, glisoxepide, glisentide, glibornuride, glibenclamide, gliquidone glimepiride, gliclazide and the pharmaceutically acceptable salts of these compounds, or muraglitazar, farglitazar, naveglitazar, netoglitazone, rivoglitazone, K-111, GW-677954, (−)-Halofenate, acid, arachidonic acid, clofbrate, gemfibrozil, fenofibrate, ciprofibrate, bezafibrate, lovastatin, pravastatin, simvastatin, mevastatin, fluvastatin, indomethacin, fenoprofen, ibuprofen, and the pharmaceutically acceptable salts of these compounds.

In one embodiment, disclosed compounds may be administered in combination with dexamphetamine, amphetamine, mazindole or phentermine; and administered in combination with medicaments having an anti-inflammatory effect.

Further, when used for the treatment of a metabolic condition, the pharmaceutical compositions provided herein can be administered as a combination therapy with one or more pharmacologically active substances having favorable effects on metabolic disturbances or disorders. For example, the disclosed pharmaceutical compositions may be administered in combination with RXR agonists for treating metabolic and cardiovascular diseases medicaments, which lower blood glucose; antidiabetics, such as insulins and insulin derivatives, including Lantus, Apidra, and other fast-acting insulins, and GLP-1 receptor modulators; active ingredients for treating dyslipidemias; anti-atherosclerotic medicaments; anti-obesity agents; anti-inflammatory active ingredients; active ingredients for treating malignant tumors; anti-thrombotic active ingredients; active ingredients for treating high blood pressure; active ingredients for treating heart failure, and combinations thereof.

EXEMPLIFICATION

Example 1a

PPARδ Activity Screen

Cell Culture and Transfection:
CV-1 cells were grown in DMEM+10% charcoal stripped FCS. Cells were seeded into 384-well plates the day before transfection to give a confluency of 50-80% at transfection. A total of 0.8 g DNA containing 0.64 micrograms pCMX-PPARDelta LBD, 0.1 micrograms pCMX.beta.Gal, 0.08 micrograms pGLMH2004 reporter and 0.02 micrograms pCMX empty vector was transfected per well using FuGene transfection reagent according to the manufacturer's instructions (Roche). Cells were allowed to express protein for 48 h followed by addition of compound.

Plasmids:
Human PPARδ was used to PCR amplify the PPARδ LBD. The amplified cDNA ligand binding domain (LBD) of PPARδ isoform was (PPARδ amino acid 128 to C-terminus) and fused to the DNA binding domain (DBD) of the yeast transcription factor GAL4 by subcloning fragments in frame into the vector pCMX GAL (Sadowski et al. (1992), Gene 118, 137) generating the plasmids pCMX-PPARDelta LBD. Ensuing fusions were verified by sequencing. The pCMXMH2004 luciferase reporter contains multiple copies of the GAL4 DNA response element under a minimal eukaryotic promoter (Hollenberg and Evans, 1988). pCMXβGal was generated.

Compounds:
All compounds were dissolved in DMSO and diluted 1:1000 upon addition to the cells. Compounds were tested in quadruple in concentrations ranging from 0.001 to 100 µM. Cells were treated with compound for 24 h followed by luciferase assay. Each compound was tested in at least two separate experiments.

Luciferase Assay:
Medium including test compound was aspirated and washed with PBS. 50 µl PBS including 1 mM Mg++ and Ca++ were then added to each well. The luciferase assay was performed using the LucLite kit according to the manufacturer's instructions (Packard Instruments). Light emission was quantified by counting on a Perkin Elmer Envision reader. To measure 3-galactosidase activity 25 µl supernatant from each transfection lysate was transferred to a new 384 microplate. Beta-galactosidase assays were performed in the microwell plates using a kit from Promega and read in a Perkin Elmer Envision reader. The beta-galactosidase data were used to normalize (transfection efficiency, cell growth etc.) the luciferase data.

Statistical Methods:
The activity of a compound is calculated as fold induction compared to an untreated sample. For each compound the efficacy (maximal activity) is given as a relative activity compared to GW501516, a PPARδ agonist. The $EC_{50}$ is the concentration giving 50% of maximal observed activity. $EC_{50}$ values were calculated via non-linear regression using GraphPad PRISM (GraphPad Software, San Diego, Calif.).

hERG Inhibition Screen

Cell Culture and Cell Harvesting:
Cells were cultured in DMEM/F-12 medium supplemented with 10% fetal bovine serum and 400 µg/mL Geneticin. Cells were grown in 75 cm tissue culture flasks maintained at 37° C. with 5% $CO_2$ and passaged every 3 days using 0.05/0.02% Trypsin/EDTA (confluency of <80%). For the purpose of electrophysiology, cells were seeded in 25 cm2 tissue culture flasks. Three day old cells were harvested using Trypsin/EDTA (0.025/0.01%) as detaching agent and resuspended in external recording solution.

Test Item Formulation:
Preweighed quantity of test item was dissolved in tissue culture grade DMSO to prepare a primary stock solution. The strength of the primary stock was 1000× of the intended highest test concentration. Subsequently, working stock solutions of appropriate strengths was prepared by dilution of primary stock with DMSO. The stock solutions were aliquoted into eppendorff tubes and stored at −20° C. freezer (<0° C.) until use. On the day of experiment, aliquots were thawed and used for preparing the assay solution (test solution).

Test solutions were prepared fresh by adding 4 µL of stock solution in to 3996 µL external recording solution such that the final DMSO concentration in the assay solution was 0.1% v/v. Upon addition, solution was inspected carefully against light by naked eye for any indications of precipitation.

Electrophysiological Procedures:
Electrophysiology Setup: Instrument: Port-A-Patch
  Patch clamp type: Semiautomatic
  Manufacturer: Nanion technologies, GmBH Germany
  Electrophysiology chips: Glasscoated NPC-1 chips
Recording Condition: Room temperature
Compound Addition Protocol: Manual addition—20 µL of solution was added on one side of the chip, followed by withdrawal of 20 µL from the other side. This way of addition and withdrawal was repeated at least 4-5 times to ensure actual test concentration is reached.
Test Concentration Exposure Period: Cells were exposed to each test concentration for 3 min or till a steady state block was reached Voltage Protocol: −40 mV subtraction pulse for 0.5 sec; +40 mV activation pre-pulse for 2 sec; −40 mV test pulse for 2 sec and −80 mV holding potential repeated at every 10 sec Assay end point: Peak hERG tail current recorded when the voltage was reduced from +40 mV to −40 mV.

Percentage hERG Current Inhibition:

The steady state current after the application of 0.1% DMSO was considered as baseline (control current). Steady state current obtained at the end of each test concentration addition was used to calculate the % hERG current inhibited at each concentration. Any rundown due to vehicle addition was corrected to calculate % hERG current inhibition. Each cell acted as its own control. Average current of last 3-5 sweeps of acceptable quality was considered for calculation of % inhibition. Sweeps with artifacts and noise were omitted while calculation.

TABLE 1

| | | PPARδ Transactivation and hERG Inhibition Data | | |
|---|---|---|---|---|
| Compound | Structure | | PPARδ Transactivation EC$_{50}$ (nM) | hERG % Inhibition at 10 μM |
| Compound 2a | 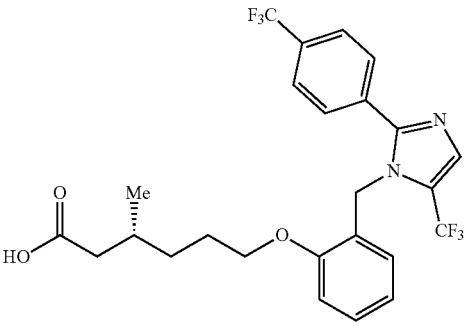 [SMILES: C[C@H](CCCOc1ccccc1Cn1c(C(F)(F)F)cnc1-c1ccc(C(F)(F)F)cc1)CC(=O)O] | | 3.00 | 6.00 |
| Compound 2b | 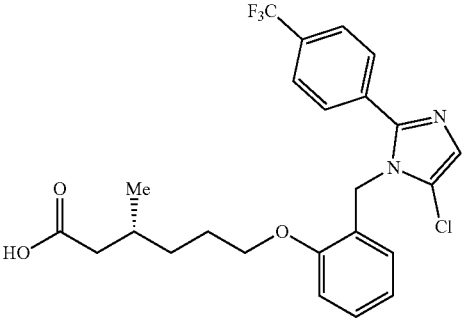 [SMILES: C[C@H](CCCOc1ccccc1Cn1c(Cl)cnc1-c1ccc(C(F)(F)F)cc1)CC(=O)O] | | 3.30 | 3.00 |
| Compound 2c | 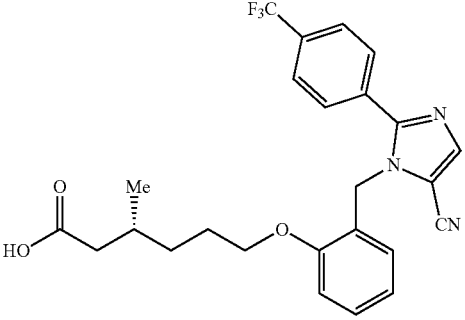 [SMILES: C[C@H](CCCOc1ccccc1Cn1c(C(F)(F)F)cnc1-c1ccc(C(F)(F)F)cc1)CC(=O)O] | | 2.70 | 2.50 |

TABLE 1-continued
PPARδ Transactivation and hERG Inhibition Data
| Compound | Structure | PPARδ Transactivation EC$_{50}$ (nM) | hERG % Inhibition at 10 μM |
|---|---|---|---|
| Compound 2d | 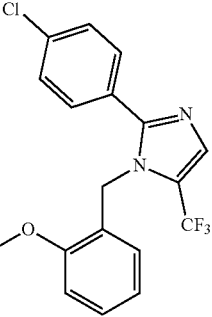 | 8.9 | 5.00 |
| Compound 2e | 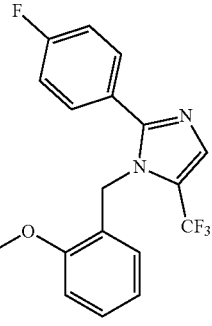 | 25.00 | Not Tested |
| Compound 2f | 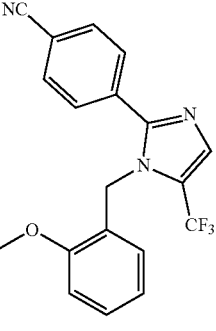 | 5.00 | 3.50 |
| Compound 2g | 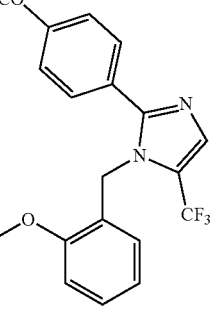 | 4.00 | 2.00 |

TABLE 1-continued

PPARδ Transactivation and hERG Inhibition Data

| Compound | Structure | PPARδ Transactivation EC$_{50}$ (nM) | hERG % Inhibition at 10 μM |
|---|---|---|---|
| Compound 2h | 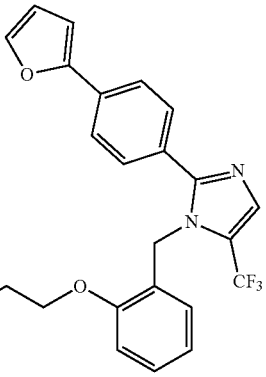 | 2.00 | 7.00 |
| Compound 2i | 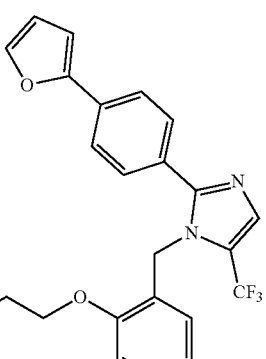 | 0.90 | 2.30 |

Example 1b

Pharmacokinetic Screening

In this example, the PK profile of several PPARδ agonists disclosed herein in male CD-1 mice or Wistar rats was determined by the methods disclosed in Boxenbaum H. (1980) Interspecies variation in liver weight, hepatic blood flow and antipyrine intrinsic clearance in extrapolation of Benzodiazepines and phenytoin. J. Pharmacokinet Biopharm 8: 165-176. Similar methods can be used to analyze other compounds provided herein.

All compounds were separately administered to CD-1 mice at 1 mg/kg iv or 3 mg/kg po. The compounds were separately administered to male Wistar rats 1 mg/kg iv or 3 mg/kg po. The species M refers to mouse and R reports to rat in the following table. NA means not available.

| Parameters/Compds | | 2a | | 2b | | 2d | | 2f | |
|---|---|---|---|---|---|---|---|---|---|
| | Species | M | R | M | R | M | R | M | R |
| IV PK | Dose, mpk | 1.0 | 1.0 | 1.0 | 1.0 | 1.0 | NA | 1.0 | 1.0 |
| | Beta T½ (h) | 5.8 | 7.1 | 3.5 | 4.8 | 6.3 | NA | 4.1 | NRV |
| | C$_0$ (ng/mL) | 740 | 1531 | 810 | 2116 | 1725 | NA | 2446 | 1819 |
| | AUC (0-inf) (ng*h/mL) | 3309 | 5042 | 1062 | 2968 | 5621 | NA | 6734 | 4091 |
| | Vss (L/kg) | 1.9 | 1.7 | 3.1 | 1.2 | 1.4 | NA | 0.6 | 3.9 |
| | Cl (mL/min/kg) | 5.0 | 3.8 | 16 | 5.8 | 5.4 | NA | 2.5 | 3.0 |
| Oral PK | Dose, mpk | 3.0 | 3.0 | 3.0 | 3.0 | 3.0 | NA | 3.0 | 3.0 |
| | T max (h) | 0.3 | 2.8 | 0.5 | 0.3 | 0.3 | NA | 0.3 | 0.3 |
| | Cmax (ng/mL) | 1257 | 1203 | 2953 | 2380 | 2827 | NA | 4240 | 4328 |
| | AUC (0-inf) | 6962 | 16104 | 3881 | 7791 | 5621 | NA | 14735 | 14874 |
| | T½ (h) | 3.8 | 77 | 4.3 | 4.1 | 10 | NA | 4.9 | 10.3 |
| | % F | 70 | 100 | 100 | 87 | 61 | NA | 73 | 100 |

Example 2

Synthetic Preparation of Compound Embodiments

Abbreviations

Me methyl
Et ethyl
OPr n-propyl
WPr isopropyl
cPr cyclopropyl
nBua n-butyl
iBu isobutyl
Boc tert-butyloxycarbonyl
Ac acetyl
Ph phenyl
Tf trifluoromethanesulfonyl
Ts 4-methylphenylsulfonyl
DIAD diisopropyl azodicarboxylate
EDCI 3-(3-dimethylaminopropyl)-1-ethylcarbodiimide
HOBt 1-hydroxybenzotriazole
HATU 1-[bis(dimethylamino)methylene]-1H-1,2,3-triazolo[4,5-b]pyridinium 3-oxide hexafluorophosphate
HBTU N,N,N,N',N'-Tetramethyl-O-(1H-benzotriazol-1-yl)uronium hexafluorophosphate
NCS N-chlorosuccinimide
NIS N-iodosuccinimide
TMSCF$_3$ (Trimethylsilyl)trifluoromethane
DIPEA diisopropylethylamine
Togni's reagent 3,3-dimethyl-1-(trifluoromethyl)-1,2-benziodoxole
DCM dichloromethane
DME dimethoxyethane
DMF N,N-dimethylformamide
DMF.DMA N,N-dimethylformamide dimethyl acetal
DMSO dimethylsulfoxide
TFA trifluoroaceticacid
THF tetrahydrofuran
MW microwaveirradiation
aq Aqueous
M concencetration expressed in mol/L
RT room temperature
TLC thin lay chromatography
HPLC high-performance liquid chromatography
MPLC medium pressure liquid chromatography
LCMS liquid chromatography-mass spectrometry
ESI+ m/z values in mass spectroscopy (Ionization ESI)
ESI− m/z values in mass spectroscopy (Ionization ESI)
$^1$H NMR (DMSO-d$_6$) S (ppm) of peak in $^1$H NMR in DMSO-d$_6$
S singlet (spectrum)
d doublet (spectrum)
t triplet (spectrum)
q quartet (spectrum)
dd double doublet (spectrum)
br broad line (spectrum)
m multiplet (spectrum).

Example 2A: Synthesis of Compound 2a

Synthesis of (3R)-3-methyl-6-(2-((5-(trifluoromethyl)-2-(4-(trifluoromethyl)phenyl)-1H-imidazol-1-yl)methyl)phenoxy)hexanoic acid

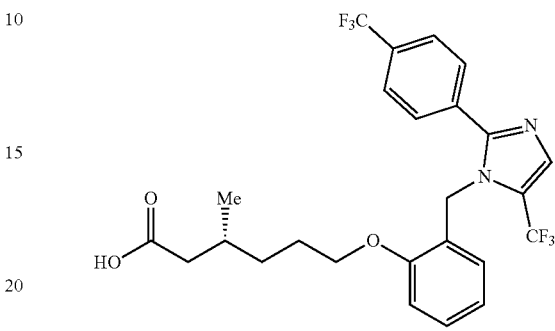

Scheme-1

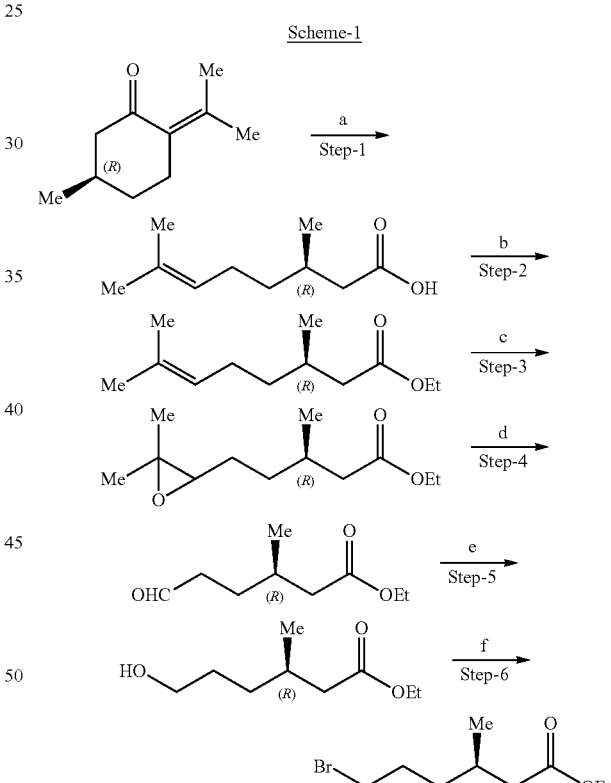

Reagents and conditions: a) i) HCl (gas), -30° C.-RT, 12 h; ii) 4N NaOH, RT, 12 h; b) Ethyl bromide, K$_2$CO$_3$, DMF, RT, 2 h; c) m-CPBA, Et$_2$O, -30° C.-0° C., 20 h; d) NaIO$_4$, 1,4 dioxane, RT, 12 h; e) NaBH$_4$, MeOH, RT, 3 h; f) PBr$_3$, DCM, 0° C.-RT, 3 h Scheme-2

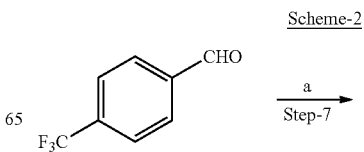

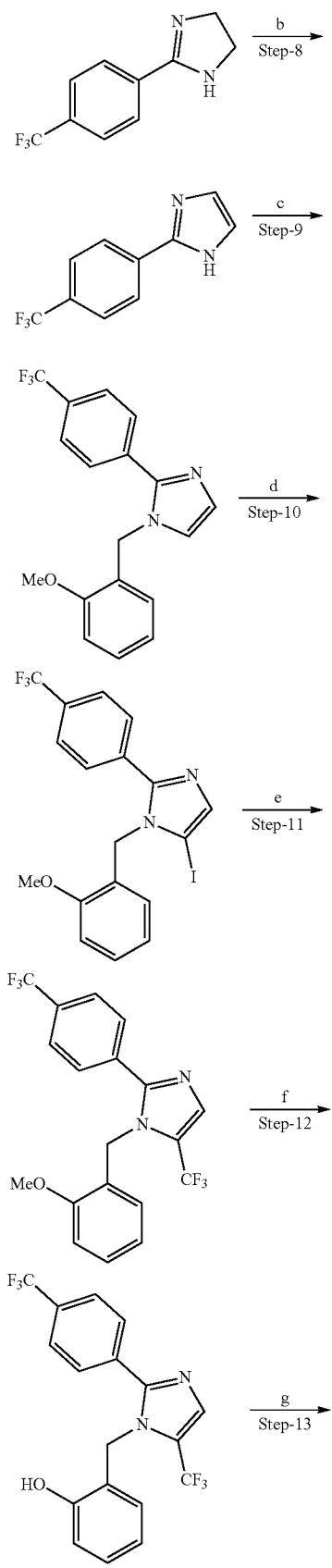

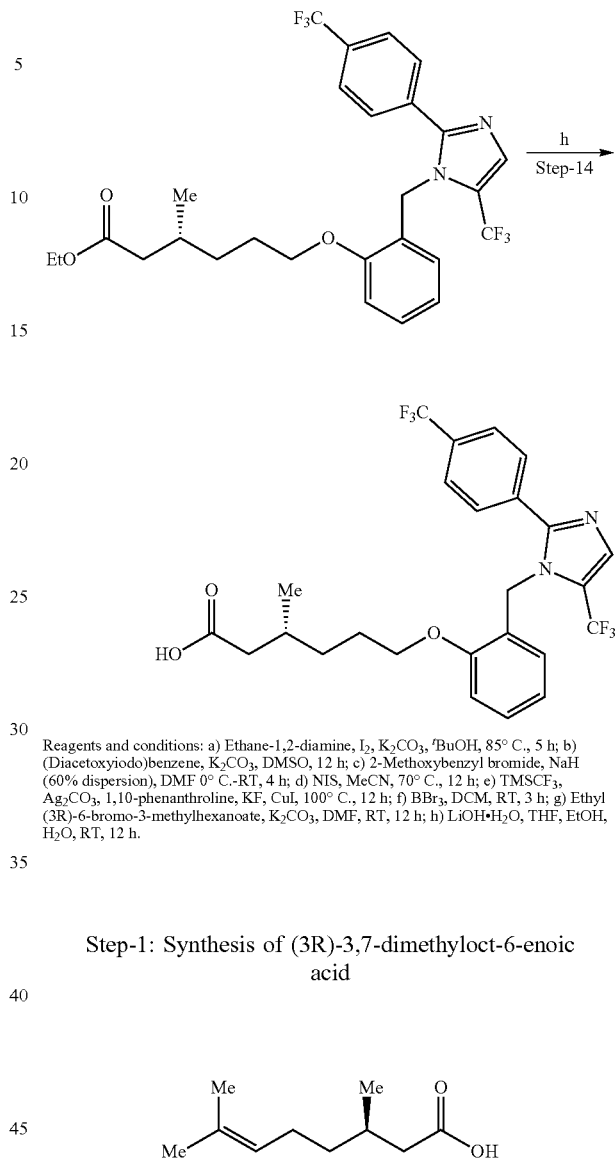

Reagents and conditions: a) Ethane-1,2-diamine, I₂, K₂CO₃, ᵗBuOH, 85° C., 5 h; b) (Diacetoxyiodo)benzene, K₂CO₃, DMSO, 12 h; c) 2-Methoxybenzyl bromide, NaH (60% dispersion), DMF 0° C.-RT, 4 h; d) NIS, MeCN, 70° C., 12 h; e) TMSCF₃, Ag₂CO₃, 1,10-phenanthroline, KF, CuI, 100° C., 12 h; f) BBr₃, DCM, RT, 3 h; g) Ethyl (3R)-6-bromo-3-methylhexanoate, K₂CO₃, DMF, RT, 12 h; h) LiOH·H₂O, THF, EtOH, H₂O, RT, 12 h.

Step-1: Synthesis of (3R)-3,7-dimethyloct-6-enoic acid

In a 5 L three neck round bottom flask, (R)-pulegone (150.0 g, 986.84 mmol) was purged with HCl gas for 3 h at −30° C. The reaction mixture was transferred to re-sealable reaction tube and mixture allowed to stand at RT for 12 h. The mixture was treated with NaOH solution (4 N, 3 L) and resulting mixture was stirred at RT for further 12 h. Upon completion of reaction (TLC), the reaction mixture was diluted with water (1 L) and washed with diethyl ether (3×1 L). The aqueous layer was acidified (pH 4) with dilute HCl before extracting with diethyl ether (3×1 L). The combined organic layer was dried over anhydrous Na₂SO₄ and concentrated under reduced pressure to get the title compound (125 g, 74.8%).

¹H NMR (300 MHz, DMSO-d₆): δ 12.01 (s, 1H), 5.07 (t, J=6.9 Hz, 1H), 2.22 (dd, J=15.0, 6.0 Hz, 1H), 2.03-1.78 (m, 4H), 1.64 (s, 3H), 1.56 (s, 3H), 1.36-1.17 (m, 2H), 0.88 (d, J=6.6 Hz, 3H).

Step-2: Synthesis of ethyl (3R)-3,7-dimethyloct-6-enoate

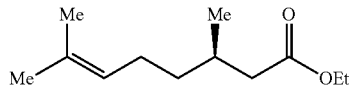 [SMILES: CCOC(=O)C[C@H](C)CCC=C(C)C]

In a 5 L round bottom flask, a suspension of (3R)-3,7-dimethyloct-6-enoic acid (100.0 g, 587.41 mmol) and K$_2$CO$_3$ (243.59 g, 1762.23 mmol) in DMF (1 L) was treated with ethyl bromide (95.94 g, 881.12 mmol) at RT. The reaction mixture was stirred at RT for 2 h. Upon completion of reaction (TLC), the reaction mixture was diluted with water (1 L) and extracted with diethyl ether (3×1 L). The combined organic extracts were dried over anhydrous Na$_2$SO$_4$ and concentrated under reduced pressure to get the title compound (101.1 g, 86.7%).
$^1$H NMR (300 MHz, CDCl$_3$): δ 5.08 (t, J=6.9 Hz, 1H), 4.12 (q, J=7.2 Hz, 2H), 2.29 (dd, J=14.7, 6.0 Hz, 1H), 2.12-2.05 (m, 1H), 1.99-1.94 (m, 3H), 1.66 (s, 3H), 1.58 (s, 3H), 1.39-1.16 (m, 2H), 1.24 (t, J=6.9 Hz, 3H), 0.93 (d, J=6.6 Hz, 3H).

Step-3: Synthesis of ethyl (3R)-5-(3,3-dimethyloxiran-2-yl)-3-methylpentanoate

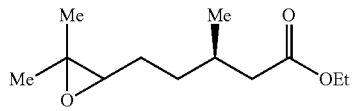 [SMILES: CCOC(=O)C[C@H](C)CCC1OC1(C)C]

In a 5 L round bottom flask, to a solution of ethyl (3R)-3,7-dimethyloct-6-enoate (100.0 g, 504.51 mmol) in diethyl ether (1 L) was added a solution of 65% m-CPBA (267.51 g, 1.01 mol) in diethyl ether (1 L) dropwise at −30° C. Once the addition was complete, the mixture was warmed to 0° C. and stirred at same temperature for 6 h, before allowing it to stand overnight (14 h) at 0-3° C. After completion of the reaction (TLC), the reaction mixture was diluted with diethyl ether (1 L) and washed with 1 N NaOH (2×1 L), followed by water (1 L). The organic layer was washed with brine, dried over anhydrous Na$_2$SO$_4$ and concentrated under reduced pressure to afford the title compound (99.5 g, 92.0%).
$^1$H NMR (300 MHz, CDCl$_3$): δ 4.12 (q, J=7.2 Hz, 2H), 2.69 (t, J=5.4 Hz, 1H), 2.30 (dd, J=8.7, 1.5 Hz 1H), 2.17-2.09 (m, 1H), 2.04-1.97 (m, 1H), 1.55-1.42 (m, 4H), 1.30 (s, 3H), 1.27 (s, 3H), 1.25 (t, J=7.2 Hz, 3H), 0.95 (d, J=6.6 Hz, 3H).

Step-4: Synthesis of ethyl (3R)-3-methyl-6-oxohexanoate

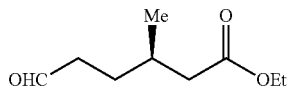 [SMILES: CCOC(=O)C[C@H](C)CCC=O]

In a 5 L round bottom flask, a solution of ethyl (3R)-5-(3,3-dimethyloxiran-2-yl)-3-methylpentanoate (99.0 g, 462.07 mmol) in 1,4-dioxane (1 L) was treated with a solution of NaIO$_4$ (296.49 g, 1.386 mol) in water (1 L) at RT. The reaction mixture was stirred at same temperature for 12 h. Upon completion of reaction (TLC), the inorganic salts were filtered through Celite® pad and filtrate was extracted with EtOAc (3×1 L). The combined organic extract was washed with water, brine and dried over anhydrous Na$_2$SO$_4$. The solution was concentrated under reduced pressure to afford the title compound (79.56 g, 99.3%).
$^1$H NMR (300 MHz, CDCl$_3$): δ 9.79 (s, 1H), 4.11 (q, J=7.2 Hz, 2H), 2.48-2.43 (m, 2H), 2.27 (dd, J=15, 6.6 Hz, 1H), 2.17-2.10 (m, 1H), 2.02-1.96 (m, 1H), 1.72-1.66 (m, 1H), 1.54-1.50 (m, 1H), 1.25 (t, J=7.2 Hz, 3H), 0.96 (d, J=6.6 Hz, 3H).

Step 5: Synthesis of ethyl (3R)-6-hydroxy-3-methylhexanoate

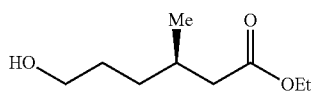

In a 1 L round bottom flask, a solution of ethyl (3R)-3-methyl-6-oxohexanoate (79.0 g, 458.76 mmol) in methanol (400 mL) was treated with NaBH$_4$ (27.75 g, 734.02 mmol) at RT. The reaction mixture was stirred at RT for 2 h. Upon completion of reaction (TLC), the reaction mixture was diluted with water (500 mL) and extracted with EtOAc (3×500 mL). The combined organic extract was dried over anhydrous Na$_2$SO$_4$ and concentrated under reduced pressure to get the title compound (70.0 g).
$^1$H NMR (300 MHz, CDCl$_3$): δ 4.12 (q, J=7.2 Hz, 2H), 3.64 (t, J=6.3 Hz, 2H), 2.30 (dd, J=14.7, 6.6 Hz, 1H), 2.17-2.09 (m, 1H), 2.02-1.96 (m, 1H), 1.67-1.56 (m, 5H), 1.26 (t, J=7.2 Hz, 3H), 0.95 (d, J=6.6 Hz, 3H).

Step-6: Synthesis of ethyl (3R)-6-bromo-3-methylhexanoate

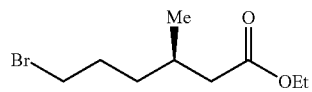 [SMILES: CCOC(=O)C[C@H](C)CCCBr]

In a 1 L round bottom flask, a solution of ethyl (3R)-6-hydroxy-3-methylhexanoate (65.0 g, 373.56 mmol) in DCM (650 mL) was treated with PBr$_3$ (101.0 g, 373.56 mmol) at RT. The reaction mixture was stirred at RT for 3 h. Upon completion of reaction (TLC), the reaction mixture was diluted with water (500 mL) and extracted with diethyl ether (3×500 mL). The organic extract was separated and dried over anhydrous Na$_2$SO$_4$. The solvent was removed under reduced pressure. The liquid obtained (57.12 g) was used directly in the next step without further purifications

Step-7: Synthesis of 2-(4-(trifluoromethyl)phenyl)-4,5-dihydro-1H-imidazole

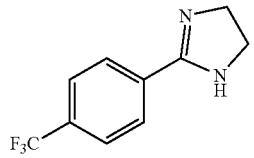 [SMILES: FC(F)(F)c1ccc(C2=NCCN2)cc1]

In a 250 mL round bottom flask, a stirred solution 4-(trifluoromethyl)benzaldehyde (5.0 g, 27.17 mmol) and ethane-1,2-diamine (1.80 g, 29.89 mmol) in $^t$BuOH (80 mL) was treated with iodine (8.60 g, 33.96 mmol) and $K_2CO_3$ (11.30 g, 81.51 mmol) at RT. The reaction mixture was heated at 85° C. for 3 h under nitrogen atmosphere. Upon completion of reaction (TLC), the reaction mixture was quenched with saturated $Na_2S_2O_3$ solution and extracted with ethyl acetate (100 mL×3). The combined organic extract was washed with brine, dried over anhydrous $Na_2SO_4$ and concentrated under reduced pressure to get desired product as a yellow solid, which was taken to next step without any purification (5.1 g, 83.1%).

$^1$H NMR (300 MHz, DMSO-$d_6$): δ 8.02 (d, J=8.1 Hz, 2H), 7.81 (d, J=8.1 Hz, 2H), 3.64 (s, 4H).

$^{19}$F NMR (300 MHz, DMSO-$d_6$): δ −66.22

LCMS (ESI+, m/z): 215.2 (M+H)$^+$.

HPLC (210 nm): 90.59%

Step-8: Synthesis of 2-(4-(trifluoromethyl)phenyl)-1H-imidazole

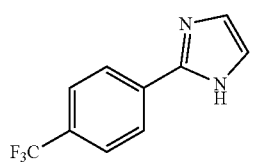 [SMILES: FC(F)(F)c1ccc(-c2ncc[nH]2)cc1]

In a 250 mL round bottom flask, a stirred solution 2-(4-(trifluoromethyl)phenyl)-4,5-dihydro-1H-imidazole (5.0 g, 23.36 mmol) in DMSO (80 mL) was treated with $K_2CO_3$ (3.55 g, 25.7 mmol) and (diacetoxyiodo)benzene (8.30 g, 25.7 mmol) at RT under nitrogen atmosphere. The reaction mixture was stirred at RT for 12 h under nitrogen atmosphere. Upon completion of reaction (TLC), the reaction mixture was diluted with ice cold water and extracted with ethyl acetate (100 mL×3). The combined organic extract was washed with brine, dried over anhydrous $Na_2SO_4$ and concentrated under reduced pressure. The residue obtained was purified by silica gel column chromatography (elution, 40% EtOAc in hexanes) to afford the title compound as a yellow solid (2.70 g, 54.7%) $^1$H NMR (400 MHz, DMSO-$d_6$): δ 12.81 (brs, 1H), 8.14 (d, J=8.8 Hz, 2H), 7.81 (d, J=8.8 Hz, 2H), 7.23 (s, 2H).

$^{19}$F NMR (400 MHz, DMSO-$d_6$): δ −60.98

LCMS (ESI+, m/z): 213.0 (M+H)$^+$.

Step-9: Synthesis of 1-(2-methoxybenzyl)-2-(4-(trifluoromethyl)phenyl)-1H-imidazole

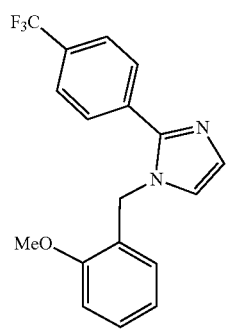 [SMILES: COc1ccccc1Cn1ccnc1-c1ccc(C(F)(F)F)cc1]

In a 250 mL round bottom flask, a stirred solution 2-(4-(trifluoromethyl)phenyl)-1H-imidazole (6.5 g, 30.66 mmol) in DMF (70 mL) was treated with NaH (60% dispersion, 1.41 g, 36.79 mmol) at 0° C. and stirred for 30 min at same temperature under nitrogen atmosphere. After 30 min, the mixture was treated with 2-methoxybenzyl bromide (7.40 g, 36.79 mmol) and reaction mixture was stirred at RT for 4 h under nitrogen atmosphere. Upon completion of reaction (TLC), the reaction mixture was quenched with saturated $NH_4Cl$ solution and extracted with ethyl acetate (100 mL×3). The combined organic extract was washed with brine, dried over anhydrous $Na_2SO_4$ and concentrated under reduced pressure. The residue obtained was purified by silica gel column chromatography (elution, 20% EtOAc in hexanes) to afford the title compound as a colorless solid (8 g, 82.5%)

$^1$H NMR (300 MHz, DMSO-$d_6$): δ 7.80 (brs, 4H), 7.30-7.26 (m, 2H), 7.10 (s, 1H), 7.01 (d, J=8.1 Hz, 1H), 6.89 (t, J=6.9 Hz, 1H) 6.75 (dd, J=7.5, 1.8 Hz, 1H), 5.29 (s, 2H), 3.68 (s, 3H).

$^{19}$F NMR (300 MHz, DMSO-$d_6$): δ −61.10

LCMS (ESI+, m/z): 333.2 (M+H)$^+$.

Step-10: Synthesis of 5-iodo-1-(2-methoxybenzyl)-2-(4-(trifluoromethyl)phenyl)-1H-imidazole

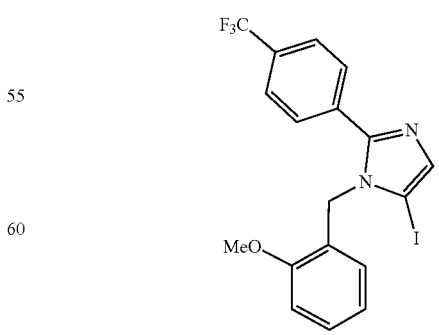

In a 250 mL round bottom flask, a stirred solution of 1-(2-methoxybenzyl)-2-(4-(trifluoromethyl)phenyl)-1H- imidazole (5 g, 15.06 mmol) in acetonitrile (50 mL) was treated with NIS (4.0 g, 18.07 mmol) at RT under nitrogen atmosphere. The reaction mixture was heated at 70° C. for 12 h. Upon completion of reaction (TLC), the reaction mixture was quenched with saturated Na₂S₂O₃ solution and extracted with ethyl acetate (100 mL×3). The combined organic extract was washed with brine, dried over anhydrous Na₂SO₄. and concentrated under reduced pressure. The residue obtained was purified by silica gel column chromatography (elution, 8% EtOAc in hexanes) to afford the title compound as a colorless solid (2.5 g, 36.3%).

LCMS (ESI+, m/z): 459.0 (M+H)⁺.

Step-11: Synthesis of 1-(2-methoxybenzyl)-5-(trifluoromethyl)-2-(4-(trifluoromethyl) phenyl)-1H-imidazole

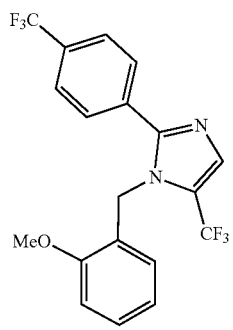 [SMILES: COc1ccccc1Cn1c(C(F)(F)F)cnc1-c1ccc(C(F)(F)F)cc1]

In a 100 mL re-sealable reaction tube, a stirred solution of 5-iodo-1-(2-methoxybenzyl)-2-(4-(trifluoromethyl)phenyl)-1H-imidazole (0.5 g, 1.09 mmol) in DMF (15 mL) was purged with argon gas at RT. Ag₂CO₃ (0.6 g, 2.18 mmol), KF (0.189 g, 3.27 mmol), 1,10-phenanthroline (0.196 g, 1.09 mmol) and CuI (0.207 g, 1.09 mmol) were sequentially added to the above reaction mixture under argon atmosphere. The reaction mixture was cooled to 0° C. and treated with TMSCF₃ (0.464 g, 3.27 mmol) under nitrogen atmosphere. The reaction mixture was heated at 100° C. for 12 h under nitrogen atmosphere. Upon completion of reaction (TLC), the reaction mixture was diluted with ethyl acetate (30 mL), filtered over Celite© bed and washed with ethyl acetate (20 mL×2). The combined organic extract was washed with brine, dried over anhydrous Na₂SO₄ and concentrated under reduced pressure. The residue obtained was purified by silica gel column chromatography (gradient elution, 3-5% EtOAc in hexanes) to afford the title compound as a clear oil (0.26 g, 59.6%).

¹H NMR (300 MHz, DMSO-d₆): δ 7.65-7.62 (m, 5H), 7.32-7.29 (m, 1H), 6.90 (t, J=7.2 Hz 2H), 6.57 (d, J=7.2 Hz, 1H), 5.31 (s, 2H), 3.82 (s, 3H).

LCMS (ESI+, m/z): 401.0 (M+H)⁺.

Step-12: Synthesis of 2-((5-(trifluoromethyl)-2-(4-(trifluoromethyl)phenyl)-1H-imidazol-1-yl)methyl) phenol

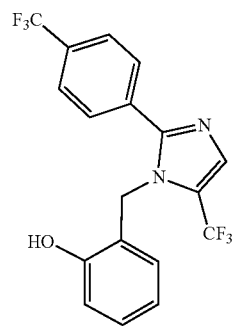 [SMILES: Oc1ccccc1Cn1c(C(F)(F)F)cnc1-c1ccc(C(F)(F)F)cc1]

In a 50 mL round bottom flask, a solution of 1-(2-methoxybenzyl)-5-(trifluoromethyl)-2-(4-(trifluoromethyl)phenyl)-1H-imidazole (0.5 g, 1.25 mmol) in DCM (5 mL) was treated with BBr₃ (1 M in DCM, 1 mL) dropwise at 0° C. The reaction mixture was stirred at RT for 3 h. Upon completion of reaction (TLC), the reaction mixture was basified with saturated NaHCO₃ solution and extracted with EtOAc (20 mL×3). The combined organic extract was dried over anhydrous Na₂SO₄ and concentrated under reduced pressure to afford the title compound Yield: 0.32 g, (66.4%).

¹H NMR (300 MHz, DMSO-d₆): δ 9.91 (s, 1H), 7.87-7.83 (m, 5H), 7.08 (t, J=9.0 Hz, 1H), 6.81-6.68 (m, 2H), 6.32 (d, J=7.5 Hz, 1H), 5.31 (s, 2H). ¹⁹F NMR (300 MHz, DMSO-d₆): δ −57.93, −61.33

LCMS (ESI+, m/z): 387.0 (M+H)⁺.

Step-13: Synthesis of ethyl (3R)-3-methyl-6-(2-((5-(trifluoromethyl)-2-(4-(trifluoromethyl)phenyl)-1H-imidazol-1-yl)methyl)phenoxy)hexanoate

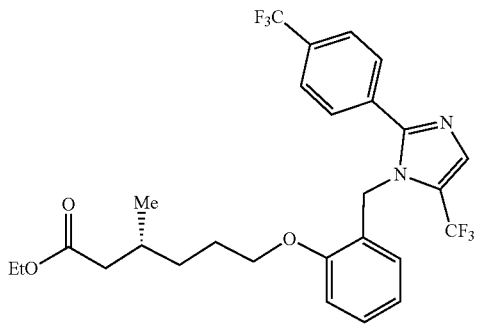

In a 50 mL round bottom flask, a stirred solution of 2-((5-(trifluoromethyl)-2-(4-(trifluoromethyl)phenyl)-1H-imidazol-1-yl)methyl)phenol (0.3 g, 0.775 mmol) in DMF (5 mL) was treated with K₂CO₃ (0.642 g, 0.465 mmol) and ethyl (3R)-6-bromo-3-methylhexanoate (0.548 g, 2.36 mmol) at RT under nitrogen atmosphere. The resulting reaction mixture was stirred at RT for 12 h. Upon completion of the reaction (TLC), the reaction mixture was quenched with ice cold water and extracted with ethyl acetate (25 mL×3). The combined organic extract was washed with brine, dried over anhydrous Na$_2$SO$_4$ and concentrated under reduced pressure. The residue obtained was purified by silica gel column chromatography (gradient elution, 15-30% EtOAc in hexanes) to afford the title compound Yield: 0.285 g (67.8%).

LCMS (ESI+, m/z): 543.0 (M+H)$^+$.

Step-14: Synthesis of (3R)-3-methyl-6-(2-((5-(trifluoromethyl)-2-(4-(trifluoromethyl) phenyl)-1H-imidazol-1-yl)methyl)phenoxy)hexanoic acid

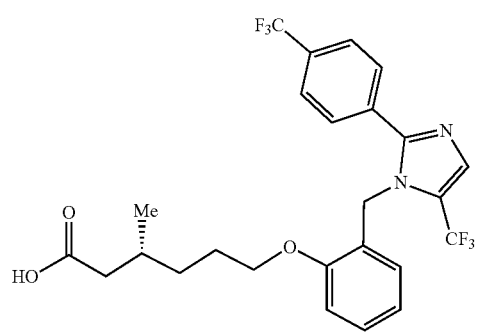 [SMILES: C[C@H](CCCOc1ccccc1Cn1c(C(F)(F)F)cnc1-c1ccc(C(F)(F)F)cc1)CC(=O)O]

In a 100 mL round bottom flask, a stirred solution of ethyl (3R)-3-methyl-6-(2-((5-(trifluoromethyl)-2-(4-(trifluoromethyl)phenyl)-1H-imidazol-1-yl)methyl)phenoxy)hexanoate (0.38 g, 0.701 mmol) in THF (5 mL), ethanol (5 mL) and water (5 mL) was treated with lithium hydroxide monohydrate (0.147 g, 3.50 mmol) at RT. The reaction mixture was stirred at RT for 12 h. Upon completion of reaction (TLC), the reaction mixture was concentrated under reduced pressure. The residue obtained was washed with EtOAc, diluted with cold water and acidified (pH ~5) with 1 N HCl. The solid obtained was purified by reverse phase preparative HPLC [Zorbax C18 (21.2 mm×150 mm, 5 μm); flow: 20 mL/min; mobile phase: A/B=0.1% TFA in water/MeCN; T/% B=0/40, 2/50, 7/80] to the yield the title compound.

Yield: 0.185 g (51.1%).

$^1$H NMR (300 MHz, DMSO-d$_6$): δ 12.0 (s, 1H), 7.82-7.76 (m, 5H), 7.22 (t, J=7.2 Hz, 1H), 6.97 (d, J=8.1 Hz, 1H), 6.83 (t, J=7.5 Hz, 1H), 6.44 (d, J=7.5 Hz, 1H), 5.34 (s, 2H), 3.94 (t, J=6.0 Hz, 2H), 2.24-2.17 (m, 1H), 2.02-1.95 (m, 1H), 1.90-1.80 (m, 1H), 1.68-1.61 (m, 2H), 1.40-1.30 (m, 1H), 1.30-1.15 (m, 1H), 0.87 (d, J=6.6 Hz, 3H).

$^{19}$F NMR (300 MHz, DMSO-d$_6$): δ −57.86, −61.38

LCMS (ESI+, m/z): 515.1 (M+H)$^+$.

HPLC (210 nm): 99.77%

Example 2B: Synthesis of Compound 2b

Synthesis of (R)-6-(2-((5-chloro-2-(4-(trifluoromethyl)phenyl)-1H-imidazol-1-yl)methyl)phenoxy)-3-methylhexanoic acid

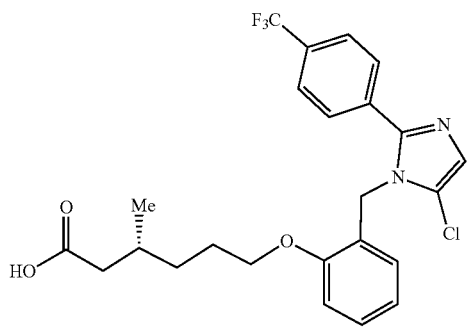

Scheme

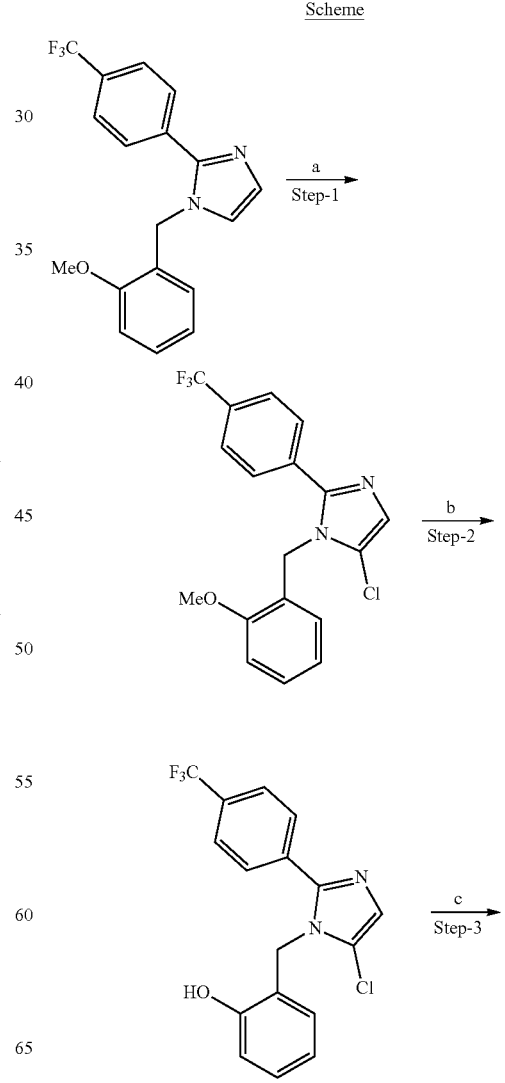

-continued

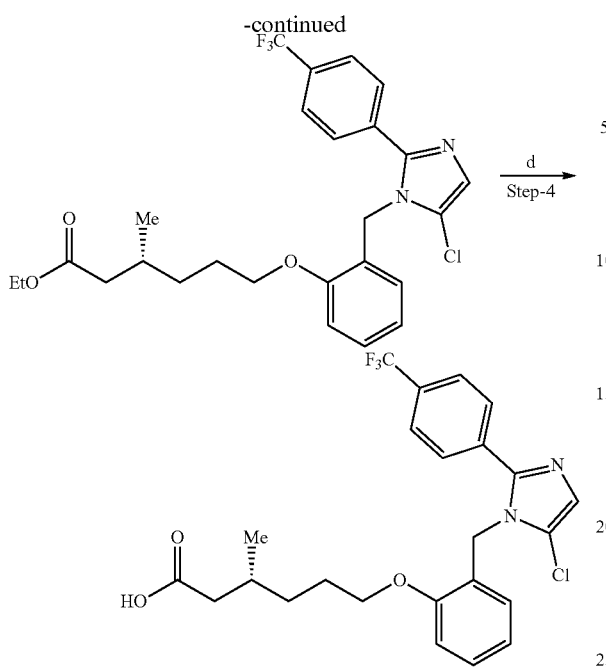

Reagents and conditions: a) NCS, DMF, 45° C., 3 h; b) BBr₃, DCM, -78° C.-RT, 2 h; c) Ethyl (R)-6-hydroxy-3-methylhexanoate, PPh₃, DIAD, PhMe, 65° C., 12 h; d) LiOH·H₂O, THF, EtOH, H₂O, RT, 16 h.

Step-1: Synthesis of 5-chloro-1-(2-methoxybenzyl)-2-(4-(trifluoromethyl)phenyl)-1H-imidazole

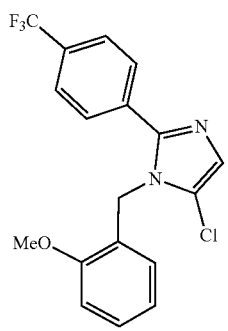 [SMILES: COc1ccccc1Cn1c(Cl)cnc1-c1ccc(C(F)(F)F)cc1]

In a 250 mL round bottom flask, a stirred solution of 1-(2-methoxybenzyl)-2-(4-(trifluoromethyl)phenyl)-1H-imidazole (9 g, 27.1 mmol), which was prepared by the methods described in Example 2A, in DMF (90 mL) was treated with NCS (4.32 g, 32.0 mmol) at RT. The reaction mixture was heated at 45° C. for 3 h. Upon completion of reaction, the reaction mixture was quenched with ice water and extracted with ethyl acetate (100 mL×2). The combined organic extracts was washed with brine, dried over anhydrous Na₂SO₄ and concentrated under reduced pressure. The residue obtained was purified by silica gel column chromatography (gradient elution, 5% EtOAc in hexanes) to afford the title compound as a white solid (4.0 g, 40.4%).

$^1$H NMR (400 MHz, CDCl₃): δ 7.60 (s, 4H), 7.33-7.29 (m, 1H), 7.20 (s, 1H), 6.94-6.90 (m, 2H), 6.70-6.65 (dd, J=8.0, 2.0 Hz, 1H), 5.23 (s, 2H), 3.84 (s, 3H).

LCMS (ESI+, m/z): 367.3 (M+H)⁺.

Step-2: Synthesis of 2-((5-chloro-2-(4-(trifluoromethyl)phenyl)-1H-imidazol-1-yl)methyl)phenol

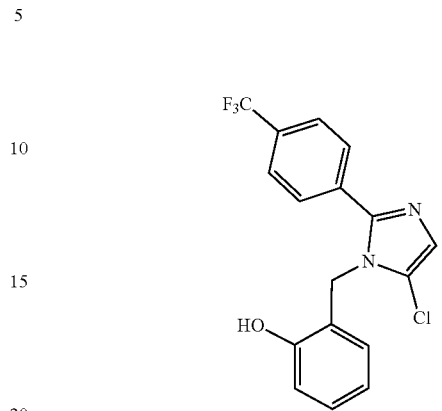

In a 500 mL round bottom flask, a solution of 5-chloro-1-(2-methoxybenzyl)-2-(4-(trifluoromethyl)phenyl)-1H-imidazole (6.0 g, 16.0 mmol) in dichloromethane (60 mL) was treated with BBr₃ (6.0 mL) dropwise at −78° C. The reaction mixture was gradually warmed to RT and stirred at RT for 2 h. Upon completion of reaction (TLC), the reaction mixture was quenched with ice water and basified with aqueous NaHCO₃. The solid was filtered and washed with EtOAc, and dried under reduced pressure to afford the title compound (5.5 g, 96.5%).

$^1$H NMR (400 MHz, DMSO-d₆): δ 9.92 (s, 1H), 7.81 (d, J=8.4 Hz, 2H), 7.74 (d, J=8.0 Hz, 2H), 7.31 (s, 1H), 7.12 (t, J=8.0 Hz, 1H), 6.83 (d, J=7.2 Hz, 1H), 6.72 (t, J=8.0 Hz, 1H), 6.38 (d, J=7.2 Hz, 1H), 5.26 (s, 2H).

LCMS (ESI+, m/z): 353.2 (M+H)⁺.

Step-3: Synthesis of ethyl (R)-6-(2-((5-chloro-2-(4-(trifluoromethyl)phenyl)-1H-imidazol-1-yl)methyl)phenoxy)-3-methylhexanoate

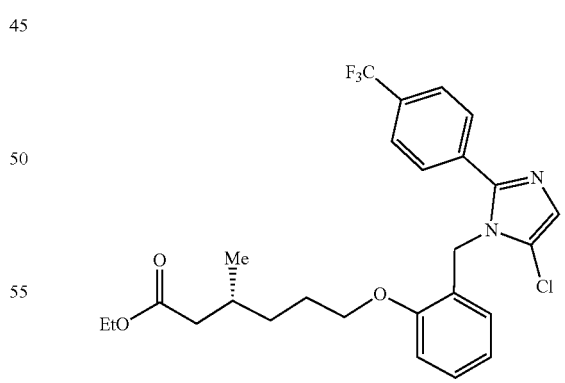

In a 250 mL round bottom flask, a stirred solution of 2-((5-chloro-2-(4-(trifluoromethyl)phenyl)-1H-imidazol-1-yl)methyl)phenol (5.5 g, 15.0 mmol) in toluene (60 mL) was treated DIAD (4.7 g, 23.0 mmol) and PPh₃ (6.1 g, 23.0 mmol) at RT under nitrogen atmosphere. The reaction mixture was stirred at RT for 15 min and treated with ethyl (3R)-6-hydroxy-3-methylhexanoate (3.2 g, 18.0 mmol), which was prepared by the methods described in Example 2A, under nitrogen atmosphere. Then resulting reaction mixture was heated to 65° C. for 12 h. Upon completion of the reaction (TLC), the reaction mixture quenched with ice cold water and extracted with n-hexane (100 mL×2). The combined organic extract was washed with brine, dried over anhydrous Na$_2$SO$_4$ and concentrated under reduced pressure. The residue obtained was purified by silica gel column chromatography (gradient elution, 5-10% EtOAc in hexanes) to afford the title compound (6.5 g, 81.9%).

LCMS (ESI+, m/z): 509.3 (M+H)$^+$.

Step-4: Synthesis of (R)-6-(2-((5-chloro-2-(4-(trifluoromethyl)phenyl)-1H-imidazol-1-yl)methyl)phenoxy)-3-methylhexanoic acid

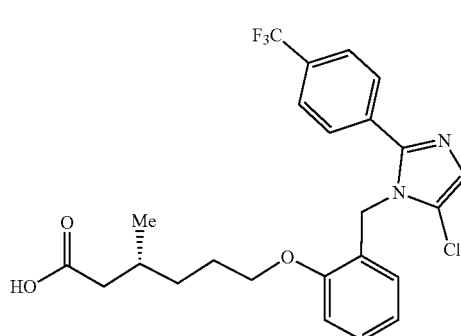

In a 500 mL round bottom flask, a stirred solution of ethyl (R)-6-(2-((5-chloro-2-(4-(trifluoromethyl)phenyl)-1H-imidazol-1-yl)methyl)phenoxy)-3-methylhexanoate (8.0 g, 15.0 mmol) in THF (100 mL) and water (100 mL), was treated with lithium hydroxide monohydrate (8.0 g, 191.0 mmol) at RT. The reaction mixture was stirred at RT for 16 h. Upon completion of reaction (TLC), the reaction mixture was diluted with water and washed with diethyl ether. The aqueous layer was neutralized with 1N HCl and solid obtained was filtered. The solid was recrystallized in ethanol and washed with n-hexane to get pure compound (3.5 g, 46.7%).

$^1$H NMR (400 MHz, DMSO-d$_6$): δ 12.03 (s, 1H), 7.78 (d, J=8.4 Hz, 2H), 7.70 (d, J=8.4 Hz, 2H), 7.30 (s, 1H), 7.23 (t, J=8.0 Hz, 1H), 7.02 (d, J=8.0 Hz, 1H), 6.85 (t, J=7.6 Hz, 1H), 6.48 (dd, J=7.6, 1.6 Hz, 1H), 5.26 (s, 2H), 3.98 (t, J=6.4 Hz, 2H), 2.22-2.17 (m, 1H), 2.01-1.95 (m, 1H), 1.85-1.78 (m, 1H), 1.69-1.63 (m, 2H), 1.37-1.33 (m, 1H), 1.24-1.22 (m, 1H), 0.85 (d, J=6.4 Hz, 3H).

$^{19}$F NMR (400 MHz, DMSO-d$_6$): δ −61.27

LCMS (ESI+, m/z): 481.3 (M+H)$^+$.

HPLC: 98.39% (210 nm).

Example 2C: Synthesis of Compound 2c

Synthesis of (3R)-6-(2-((5-cyano-2-(4-(trifluoromethyl)phenyl)-1H-imidazol-1-yl)methyl)phenoxy)-3-methylhexanoic acid

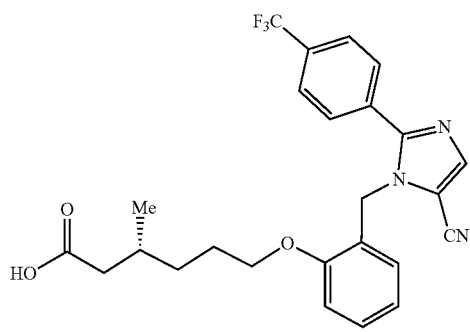 [SMILES: C[C@H](CCCOc1ccccc1Cn1c(C#N)cnc1-c1ccc(C(F)(F)F)cc1)CC(=O)O]

Scheme

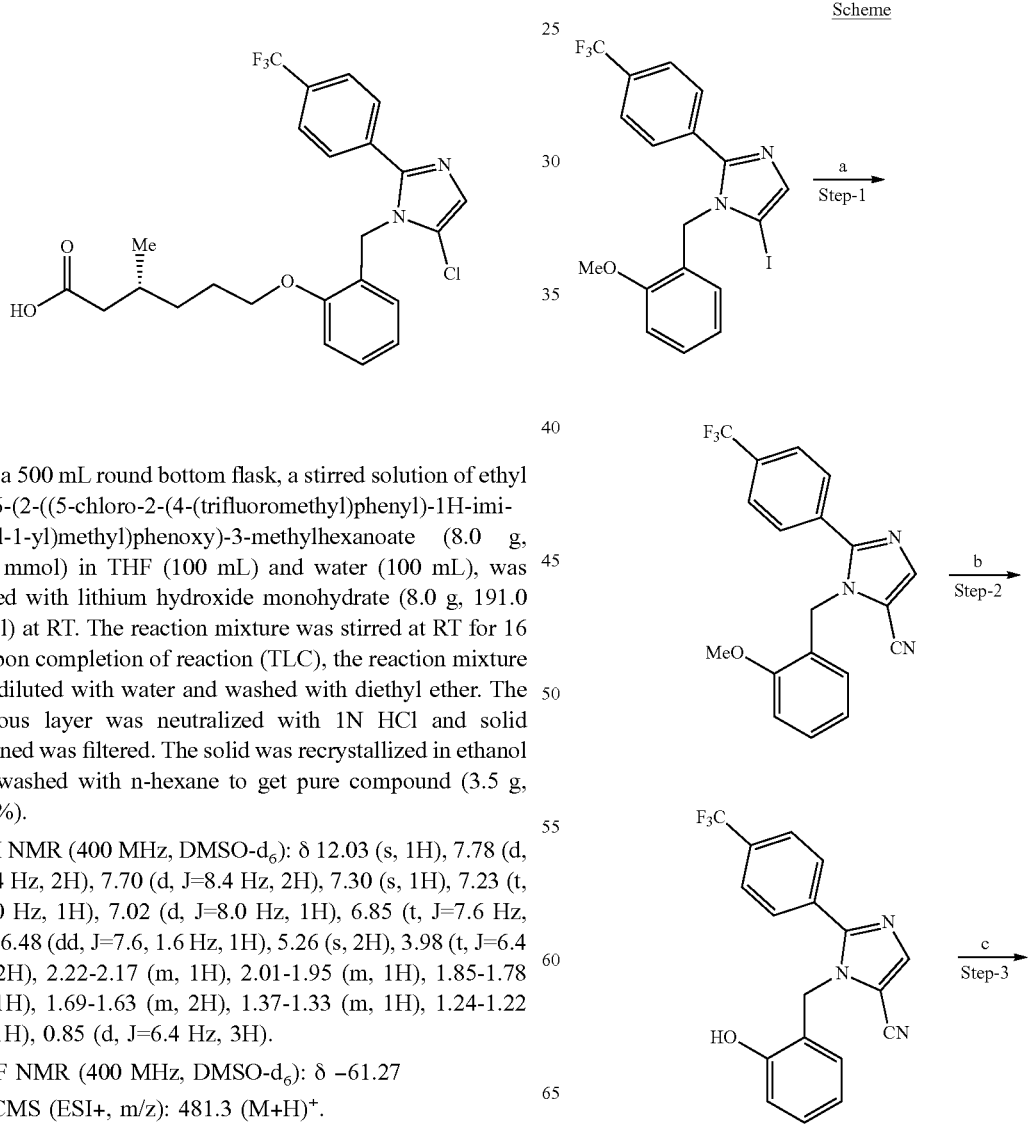

39

-continued

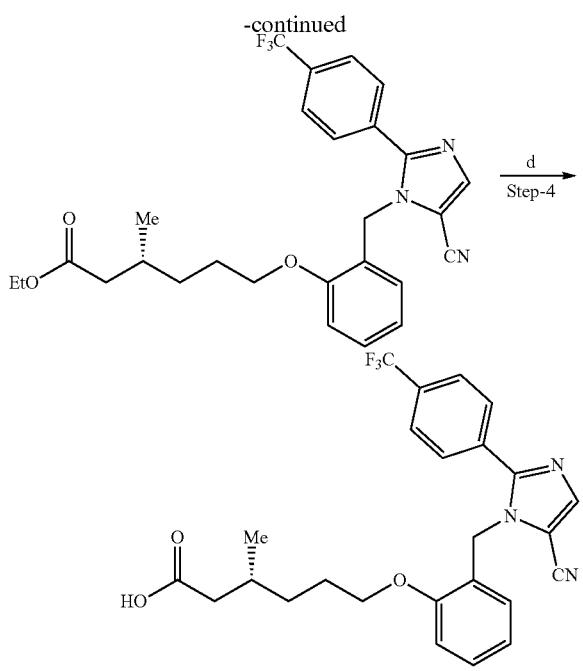

Reagents and conditions: a) CuCN, Pd(PPh₃)₄, microwave, 150° C., 2 h; b) BBr₃, DCM, RT, 36 h; c) Ethyl (3R)-6-bromo-3-methylhexanoate, K₂CO₃, DMF, RT, 24 h; d) LiOH•H₂O, THF, EtOH, H₂O, 0° C.-10° C., 36 h.

Step-1: Synthesis of 1-(2-methoxybenzyl)-2-(4-(trifluoromethyl)phenyl)-1H-imidazole-5-carbonitrile

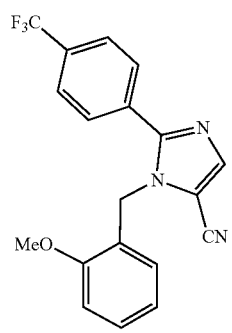

In a 20 mL microwave vial, a stirred solution 5-iodo-1-(2-methoxybenzyl)-2-(4-(trifluoromethyl)phenyl)-1H-imidazole (2 g, 4.36 mmol) in DMF (10 mL) was purged with argon gas at RT. CuCN (0.97 g, 10.917 mmol) and Pd(PPh₃)₄ (0.2 g, 0.174 mmol) were sequentially added to the above mixture under argon atmosphere. The reaction mixture was heated at 150° C. for 2 h in a microwave. Upon completion of reaction (TLC), the reaction mixture was diluted with ethyl acetate (30 mL) and water (20 mL), filtered over Celite® bed and washed with ethyl acetate (20 mL×2). The combined filtrate was washed with brine, dried over anhydrous Na₂SO₄ and concentrated under reduced pressure. The residue obtained was purified by silica gel column chromatography (elution, 10% EtOAc in hexanes) to afford the title compound as a white solid (0.7 g, 45.2%).
$^1$H NMR (300 MHz, CDCl₃): δ 7.83 (s, 1H), 7.68 (d, J=1.2 Hz, 4H), 7.32 (m, 1H), 6.93-6.88 (m, 2H), 6.73-6.71 (d, J=7.5 Hz, 1H), 5.36 (s, 2H), 3.77 (s, 3H).
LCMS (ESI+, m/z): 357.9 (M+H)⁺.

40

Step-2: Synthesis of 1-(2-hydroxybenzyl)-2-(4-(trifluoromethyl)phenyl)-1H-imidazole-5-carbonitrile

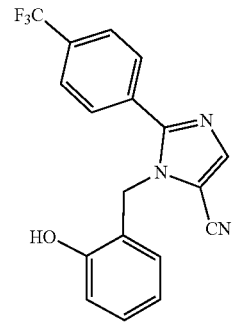 [SMILES: N#Cc1cnc(-c2ccc(C(F)(F)F)cc2)n1Cc1ccccc1O]

In a 50 mL round bottom flask, a stirred solution of 1-(2-methoxybenzyl)-2-(4-(trifluoromethyl)phenyl)-1H-imidazole-5-carbonitrile (0.7 g, 1.96 mmol) in DCM (5 mL) was treated with a solution of BBr₃ (1 M in DCM, 4.9 g, 19.60 mmol) at 0° C. under nitrogen atmosphere. The resulting reaction mixture was stirred at RT for 12 h and treated again with a solution of BBr₃ in DCM (4.9 g, 19.60 mmol) at 0° C. under nitrogen atmosphere. The reaction was stirred for another 24 h at RT under nitrogen atmosphere. Upon completion of reaction (TLC), reaction mixture was quenched with ice cold NaHCO₃ solution and extracted with DCM (50 mL×2). The combined organic extract was washed with brine, dried over anhydrous Na₂SO₄ and concentrated under reduced pressure. The residue obtained was purified by silica gel column chromatography (gradient elution, 10-15% MeOH—CHCl₃) to afford the title compound as off-white solid (0.31 g, 44.8%).
$^1$H NMR (300 MHz, DMSO-d₆): δ 9.90 (brs, 1H), 8.10 (s, 1H), 8.0-7.81 (m, 4H), 7.15-7.10 (t, J=7.5 Hz, 1H), 6.82-6.62 (m, 3H), 5.35 (s, 2H).
LCMS (ESI+, m/z): 344.2 (M+H)⁺.

Step-3: Synthesis of ethyl (3R)-6-(2-((5-cyano-2-(4-(trifluoromethyl)phenyl)-1H-imidazol-1-yl)methyl)phenoxy)-3-methylhexanoate

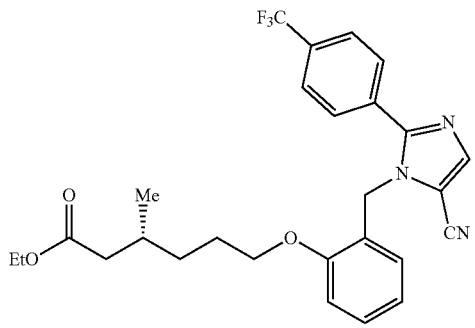

The title compound was synthesized from 1-(2-hydroxybenzyl)-2-(4-(trifluoromethyl)phenyl)-1H-imidazole-5-carbonitrile (0.15 g, 0.437 mmol) and ethyl (3R)-6-bromo-3-methylhexanoate (0.31 g, 1.311 mmol) following the experimental procedure described in step-13 of Example 2A.

Yield: 0.11 g (47.6%).
$^1$H NMR (300 MHz, CDCl$_3$): δ 7.84 (s, 1H), 7.67 (m, 4H), 7.30-7.27 (m, 1H), 6.92-6.87 (t, J=8.1 Hz, 2H), 6.76 (d, J=6.6 Hz, 1H), 5.36 (s, 2H), 4.13 (q, J=6.6 Hz, 2H), 4.01 (t, J=6.9 Hz, 2H), 2.26-2.24 (m, 1H), 2.16-2.08 (m, 2H), 1.77-1.76 (m, 2H), 1.41 (m, 1H), 1.22-1.18 (m, 4H), 0.95 (d, J=6.6 Hz, 3H).
LCMS (ESI+, m/z): 500.1 (M+H)$^+$.

Step-4: Synthesis of (3R)-6-(2-((5-cyano-2-(4-(trifluoromethyl)phenyl)-1H-imidazol-1-yl)methyl)phenoxy)-3-methylhexanoic acid

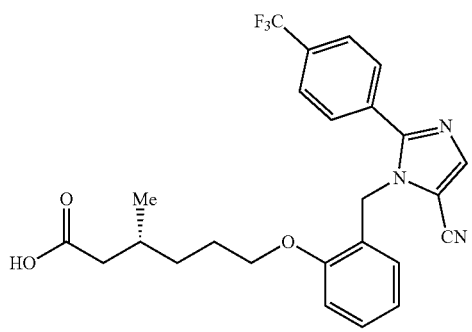

The title compound was synthesized from ethyl (3R)-6-(2-((5-cyano-2-(4-(trifluoromethyl)phenyl)-1H-imidazol-1-yl)methyl)phenoxy)-3-methylhexanoate (0.075 g, 0.150 mmol) following the experimental procedure described in step-14 of Example 2A and purification was done by reverse phase preparative HPLC [Kinetex EVO C18: 21.2 mm×150 mm); flow: 15 mL/min; mobile phase: A/B=water/MeCN; T/% B=0/45, 2/55, 12/75].

Yield: 0.032 g (45.1%).
$^1$H NMR (400 MHz, CD$_3$OD): δ 7.92 (s, 1H), 7.80-7.73 (m, 4H), 7.31-7.27 (m, 1H), 6.97 (d, J=8.0 Hz, 1H), 6.86-6.80 (m, 2H), 5.24 (s, 2H), 3.94 (t, J=6.4 Hz, 2H), 2.29-2.14 (m, 1H), 1.98-1.92 (m, 1H), 1.83-1.78 (m, 1H), 1.67-1.6 (m, 2H), 1.37-1.331 (m, 1H), 1.22-1.18 (m, 1H), 0.97 (d, J=6.4 Hz, 3H).
$^{19}$F NMR (400 MHz, CD$_3$OD): δ -61.38
LCMS (ESI+, m/z): 472.3 (M+H)$^+$.
HPLC: 95.05% (210 nm).

Example 2D: Synthesis of Compound 2d

Synthesis of (3R)-6-(2-((2-(4-chlorophenyl)-5-(trifluoromethyl)-1H-imidazol-1-yl)methyl)phenoxy)-3-methylhexanoic acid

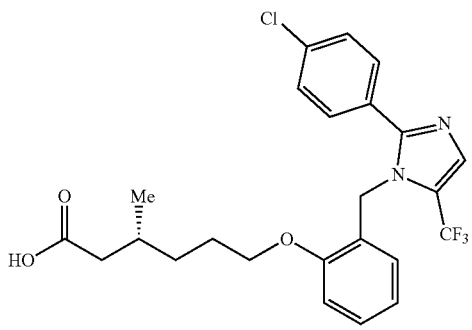 [SMILES: C[C@H](CCCOc1ccccc1Cn1c(C(F)(F)F)cnc1-c1ccc(Cl)cc1)CC(=O)O]

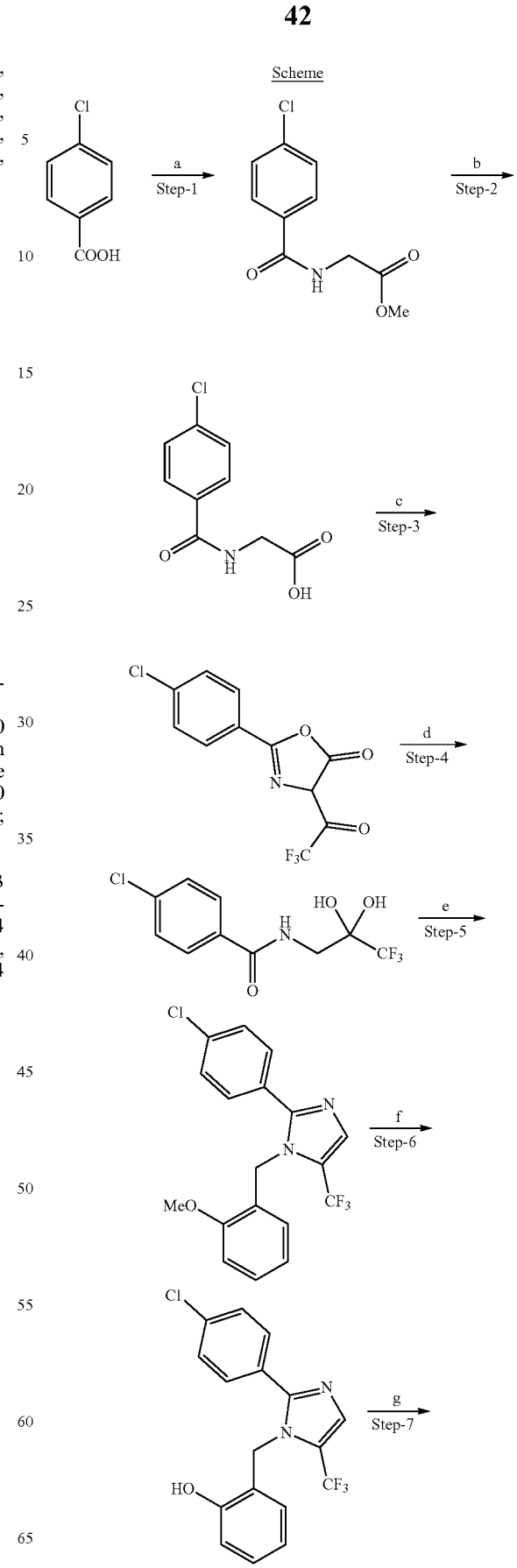

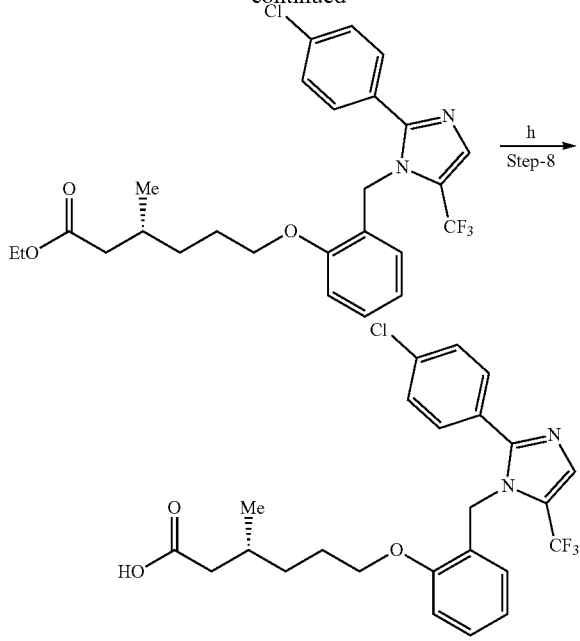

Reagents and conditions: a) Methyl glycinate hydrochloride, EDCI•HCl, HOBt, Et₃N, DMF, 12 h; b) LiOH•H₂O, THF, EtOH, H₂O, RT, 12 h; c) 2,2,2-Trifluoroacetic anhydride, acetone, 0° C., 12 h; d) 1,4-Dioxane, H₂O, 3 h; e) 2-Methoxybenzyl amine, AcOH, toluene, 120° C., 12 h; f) BBr₃, DCM, -78° C.-RT, 3 h; g) Ethyl (3R)-6-bromo-3-methylhexanoate, K₂CO₃, DMF, RT, 12 h; 12 h; h) LiOH•H₂O, THF, H₂O, RT, 12 h.

Step-1: Synthesis of methyl 2-(4-chlorobenzamido)acetate

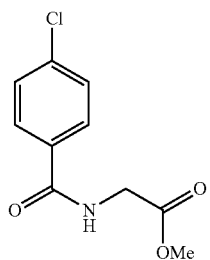 [SMILES: COC(=O)CNC(=O)c1ccc(Cl)cc1]

In a 1000 mL round bottom flask, a stirred solution of 4-chlorobenzoic acid (25.0 g, 160 mmol) and methyl glycinate hydrochloride (30.12 g, 240 mmol) in DMF (250 mL) was treated sequentially with EDCI.HCl (61.28 g, 320 mmol), HOBt (43.23 g, 320 mmol) and Et₃N (111 mL, 800 mmol) at RT under nitrogen atmosphere. The reaction mixture was stirred at RT for 12 h under nitrogen atmosphere. Upon completion of reaction (TLC), the reaction mixture was diluted with ice cold water and extracted with ethyl acetate (500 mL×3). The combined organic extract was washed with brine, dried over anhydrous Na₂SO₄ and concentrated under reduced pressure. The residue obtained was purified by silica gel column chromatography (gradient elution, 15-30% EtOAc in hexanes) to afford the title compound (20.5 g, 56.4%)

¹H NMR (300 MHz, CDCl₃): δ 7.75 (d, J=8.4 Hz, 2H), 7.42 (d, J=8.4 Hz, 2H), 6.66 (brs, 1H), 4.24 (d, J=4.8 Hz, 2H), 3.80 (s, 3H).

LCMS (ESI+, m/z): 227.9, 229.9 (M+H)⁺.

Step-2: Synthesis of (4-chlorobenzoyl)glycine

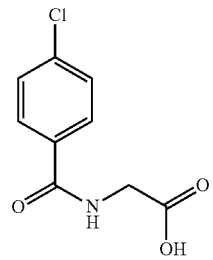 [SMILES: O=C(O)CNC(=O)c1ccc(Cl)cc1]

In a 500 mL round bottom flask, a stirred solution of methyl 2-(4-chlorobenzamido)acetate (20 g, 88.1 mmol) in THF (100 mL), methanol (100 mL) and water (100 mL) was treated with lithium hydroxide monohydrate (18.5 g, 441 mmol) at RT. The reaction mixture was stirred at RT for 12 h. Upon completion of reaction (TLC), the reaction mixture was concentrated under reduced pressure. The residue obtained was washed with EtOAc, diluted with cold water and acidified (pH 5) with 1 N HCl. The solid was filtered and dried under reduced pressure to give the title compound (14.21 g, 75.6%).

¹H NMR (300 MHz, DMSO-d₆): δ 12.7 (brs, 1H), 8.93 (t, J=5.7 Hz, 1H), 7.88-7.84 (m, 2H), 7.54 (d, J=8.7 Hz, 2H), 3.90 (d, J=6.3 Hz, 2H).

LCMS (ESI+, m/z): 214.0, 216.0 (M+H)⁺.

Step-3: Synthesis of 2-(4-chlorophenyl)-4-(2,2,2-trifluoroacetyl)oxazol-5 (4H)-one

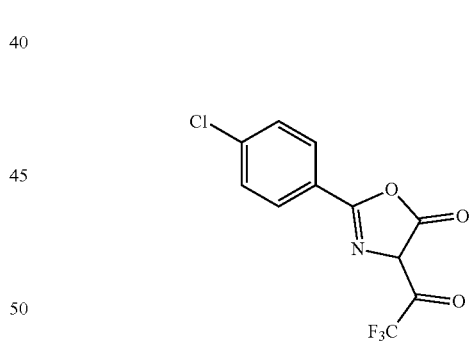

In a 250 mL round bottom flask, a stirred solution of (4-chlorobenzoyl)glycine (10 g, 46.9 mmol) in acetone (100 mL) was treated with 2,2,2-trifluoroacetic anhydride (29.8 g, 140 mmol) at 0° C. under argon atmosphere. The reaction mixture was stirred at RT for 12 h. Upon completion of reaction (TLC), the reaction mixture was concentrated under reduced pressure. The residue obtained was diluted with cold water and solid precipitated was filtered. The solid was washed with water (100 mL) and dried under reduced pressure to give the desired product as a brown solid which was taken to next step without any purification (9.92 g).

¹H NMR (300 MHz, DMSO-d₆): δ 7.91 (d, J=8.7 Hz, 1H), 7.22 (d, J=8.4 Hz, 1H), 7.60 (d, J=8.7 Hz, 1H), 7.47 (d, J=8.7 Hz, 1H).

Step-4: Synthesis of 4-chloro-N-(3,3,3-trifluoro-2,2-dihydroxypropyl)benzamide

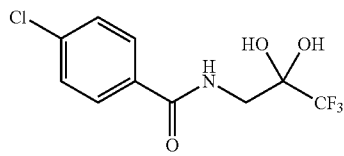 [SMILES: O=C(NCC(O)(O)C(F)(F)F)c1ccc(Cl)cc1]

In a 250 mL round bottom flask, a stirred solution of 2-(4-chlorophenyl)-4-(2,2,2-trifluoroacetyl)oxazol-5 (4H)-one (9.9 g, 34.1 mmol) in 1,4-dioxane (100 mL) and water (100 mL) was heated at 100° C. under argon atmosphere for 3 h. Upon completion of reaction (TLC), the reaction mixture was diluted with ice cold water and extracted with ethyl acetate (100 mL×3). The combined organic extract was washed with brine, dried over anhydrous $Na_2SO_4$ and concentrated under reduced pressure to give the desired product as a brown solid which was taken to next step without any purification (8.82 g).

$^1$H NMR (300 MHz, DMSO-$d_6$): δ 8.61 (t, J=6.0 Hz, 1H) 7.88 (d, J=8.7 Hz, 2H), 7.56 (d, J=8.7 Hz, 2H), 7.22 (brs, 2H), 3.60 (d, J=6.0 Hz, 2H)

Step-5: Synthesis of 2-(4-chlorophenyl)-1-(2-methoxybenzyl)-5-(trifluoromethyl)-1H-imidazole

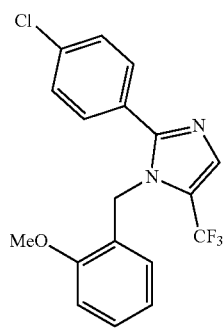 [SMILES: COc1ccccc1Cn1c(C(F)(F)F)cnc1-c1ccc(Cl)cc1]

In a 100 mL re-sealable reaction tube, a stirred solution of 4-chloro-N-(3,3,3-trifluoro-2,2-dihydroxypropyl)benzamide (2 g, 7.06 mmol) in toluene (20 mL) was treated with 2-methoxylbenzyl amine (1.46 g, 10.70 mmol) and acetic acid (0.6 mL) at RT. The reaction mixture was heated at 120° C. under argon atmosphere for 18 h. Upon completion of reaction (TLC), the reaction mixture was quenched with saturated $NaHCO_3$ solution and extracted with ethyl acetate (25 mL×3). The combined organic extract was washed with brine, dried over anhydrous $Na_2SO_4$ and concentrated under reduced pressure. The residue obtained was purified by silica gel column chromatography (elution, 5% EtOAc in hexanes) to afford the title compound as a clear oil. (0.186 g, 7.2%)

LCMS (ESI+, m/z): 367.0, 369.0 (M+H)$^+$.

Step-6: Synthesis of 2-((2-(4-chlorophenyl)-5-(trifluoromethyl)-1H-imidazol-1-yl)methyl)phenol

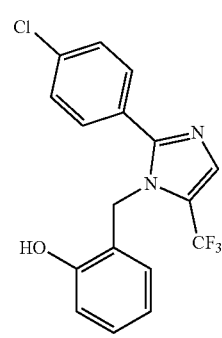 [SMILES: Oc1ccccc1Cn1c(C(F)(F)F)cnc1-c1ccc(Cl)cc1]

The title compound was synthesized from 2-(4-chlorophenyl)-1-(2-methoxybenzyl)-5-(trifluoromethyl)-1H-imidazole (0.4 g, 1.09 mmol) following the experimental procedure described in step-12 of Example 2A.

Yield: 0.15 g.

LCMS (ESI+, m/z): 352.9, 354.9 (M+H)$^+$.

Step-7: Synthesis of ethyl (3R)-6-(2-((2-(4-chlorophenyl)-5-(trifluoromethyl)-1H-imidazol-1-yl)methyl)phenoxy)-3-methylhexanoate

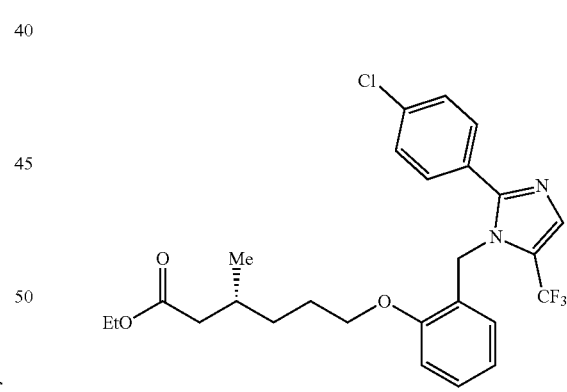

The title compound was synthesized from 2-((2-(4-chlorophenyl)-5-(trifluoromethyl)-1H-imidazol-1-yl)methyl)phenol (0.15 g, 0.426 mmol) and ethyl (3R)-6-bromo-3-methylhexanoate (0.29 g, 1.29 mmol) following the experimental procedure described in step-13 of Example 2A.

Yield: 0.141 g (65.3%).

LCMS (ESI+, m/z): 508.9, 510.9 (M+H)$^+$.

Step-8: Synthesis of (3R)-6-(2-((2-(4-chlorophenyl)-5-(trifluoromethyl)-1H-imidazol-1-yl)methyl)phenoxy)-3-methylhexanoic acid

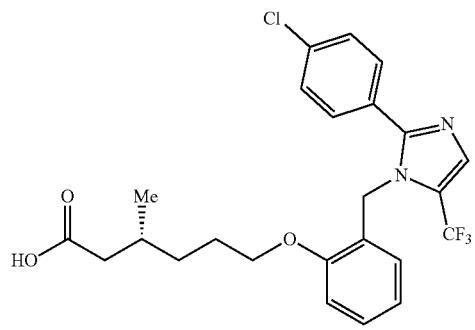 [SMILES: C[C@H](CCCOc1ccccc1Cn1c(C(F)(F)F)cnc1-c1ccc(Cl)cc1)CC(=O)O]

The title compound was synthesized from ethyl (3R)-6-(2-((2-(4-chlorophenyl)-5-(trifluoromethyl)-1H-imidazol-1-yl)methyl)phenoxy)-3-methylhexanoate (0.140 g, 0.275 mmol) following the experimental procedure described in step-14 of Example 2A.

Yield: 0.032 g (24.2%).

$^1$H NMR (400 MHz, CD$_3$OD): δ 7.67 (d, J=1.2 Hz, 1H), 7.47-7.41 (m, 4H), 7.26 (t, J=8.4 Hz, 1H), 6.95 (d, J=7.6 Hz, 1H), 6.86 (t, J=7.6 Hz, 1H), 6.53 (d, J=6.4 Hz, 1H), 5.36 (s, 2H), 3.99 (t, J=6.0 Hz, 2H), 2.34-2.29 (m, 1H), 2.15-2.10 (m, 1H), 2.00-1.82 (m, 1H), 1.80-1.73 (m, 2H), 1.54-1.45 (m, 1H), 1.36-1.29 (m, 1H), 0.95 (d, J=6.8 Hz, 3H).

$^{19}$F NMR (400 MHz, CD$_3$OD): δ −60.58

LCMS (ESI+, m/z): 481.0, 483.0 (M+H)$^+$.

HPLC (210 nm): 96.02%

Example 2E: Synthesis of Compound 2e

Synthesis of (3R)-6-(2-((2-(4-fluorophenyl)-5-(trifluoromethyl)-1H-imidazol-1-yl)methyl)phenoxy)-3-methylhexanoic acid

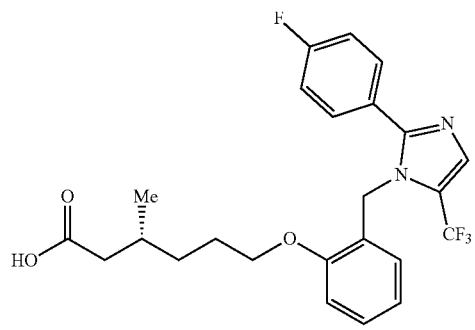 [SMILES: C[C@H](CCCOc1ccccc1Cn1c(C(F)(F)F)cnc1-c1ccc(F)cc1)CC(=O)O]

Scheme

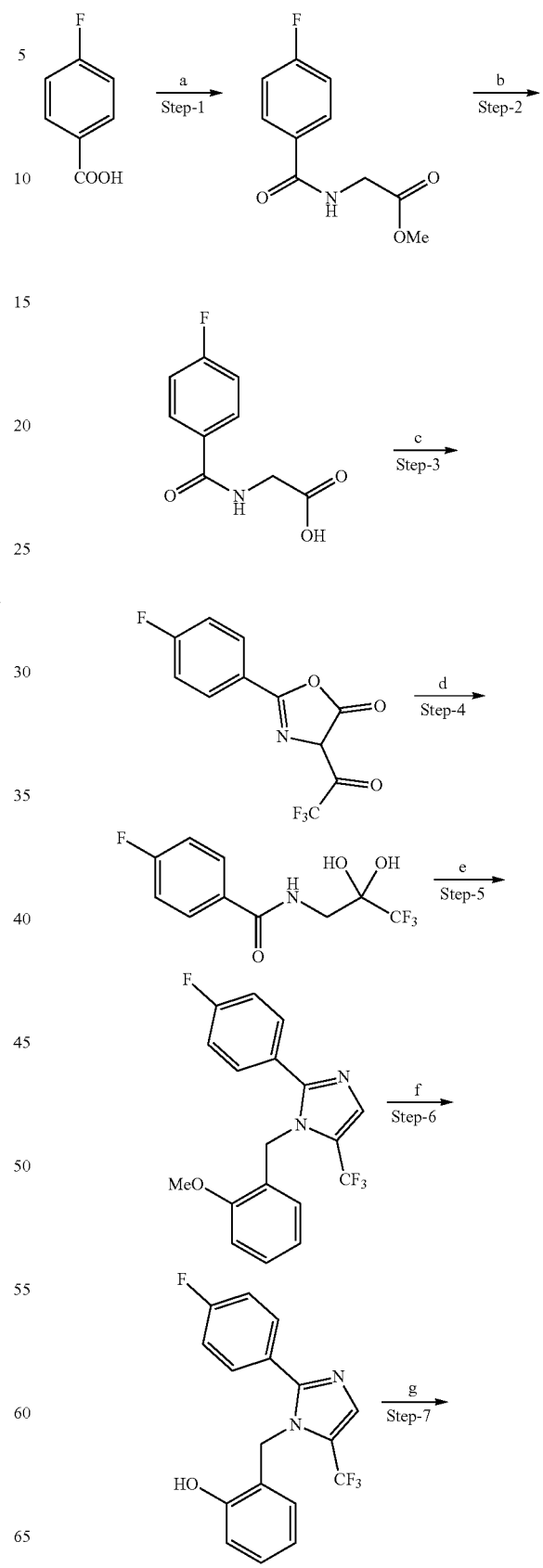

-continued

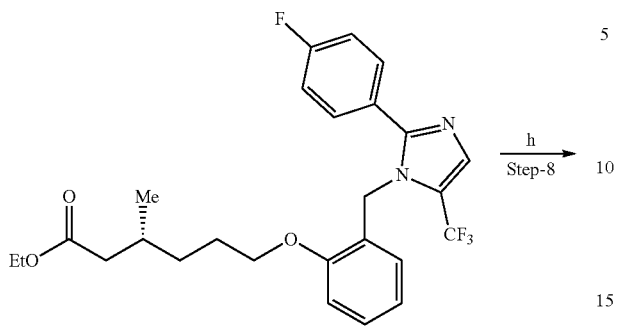

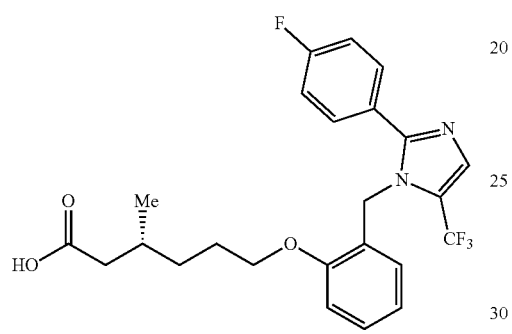

Reagents and conditions: a) Methyl glycinate hydrochloride, EDCI•HCl, HOBt, Et₃N, DMF, RT, 12 h; b) LiOH•H₂O, THF, EtOH, H₂O, RT, 12 h; c) 2,2,2-Trifluoroacetic anhydride, acetone, 0° C., RT, 4 h; d) 1,4-Dioxane, H₂O, 100° C., 3 h; e) 2-Methoxybenzyl amine, AcOH, toluene, 120° C., 12 h; f) BBr₃, DCM 78° C.-RT; g) Ethyl (3R)-6-bromo-3-methylhexanoate, K₂CO₃, DMF, RT, 12 h; h) LiOH•H₂O, THF, EtOH, H₂O, RT, 12 h.

Step-1: Synthesis of methyl (4-fluorobenzamido)acetate

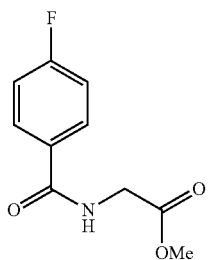 [SMILES: COC(=O)CNC(=O)c1ccc(F)cc1]

The title compound was synthesized from 4-fluorobenzoic acid (20.0 g, 142.74 mmol) and methyl glycinate hydrochloride (26.87 g, 214.11 mmol) following the experimental procedure described in step-1 of Example 2D.

Yield: 24.65 g (81.7%).

$^1$H NMR (400 MHz, DMSO-d$_6$): δ 9.0 (t, J=6.4 Hz, 1H), 7.96-7.92 (m, 2H), 7.32 (t, J=8.8 Hz, 2H), 4.01 (d, J=6.0 Hz, 2H), 3.65 (s, 3H).

LCMS (ESI+, m/z): 212.0 (M+H)$^+$.

Step-2: Synthesis of (4-fluorobenzoyl)glycine

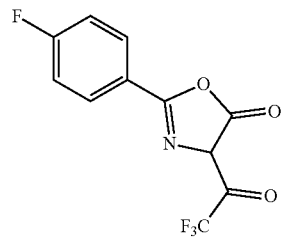

The title compound was synthesized from methyl (4-fluorobenzamido)acetate (12.5 g, 59.1 mmol) following the experimental procedure described in step-2 of Example 2D.

Yield: 7.15 g (61.3%).

$^1$H NMR (400 MHz, DMSO-d$_6$): δ 12.7 (brs, 1H), 8.88 (t, J=6.0 Hz, 1H), 7.96-7.91 (m, 2H), 7.35-7.29 (m, 2H), 3.92 (t, J=6.0 Hz, 2H).

$^{19}$F NMR (400 MHz, DMSO-d$_6$): δ −109.18

Step-3: Synthesis of 2-(4-fluorophenyl)-4-(2,2,2-trifluoroacetyl)oxazol-5 (4H)-one

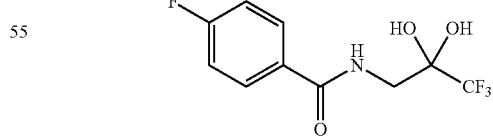

The title compound was synthesized from (4-fluorobenzoyl)glycine (11.2 g, 56.8 mmol) following the experimental procedure described in step-3 of Example 2D.

Yield: 11.7 g (74.8%).

LCMS (ESI+, m/z): 276.1 (M+H)$^+$.

Step-4: Synthesis of 4-fluoro-N-(3,3,3-trifluoro-2,2-dihydroxypropyl)benzamide

The title compound was synthesized from 2-(4-fluorophenyl)-4-(2,2,2-trifluoroacetyl)oxazol-5 (4H)-one (11.7 g, 42.5 mmol) following the experimental procedure described in step-4 of Example 2D.

Yield: 9.75 g (85.8%).

LCMS (ESI+, m/z): 268.0 (M+H)$^+$.

Step-5: Synthesis of 2-(4-fluorophenyl)-1-(2-methoxybenzyl)-5-(trifluoromethyl)-1H-imidazole

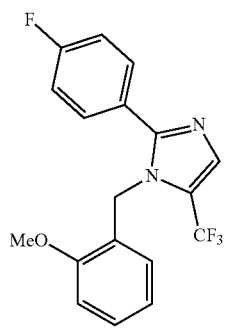

The title compound was synthesized from of 4-fluoro-N-(3,3,3-trifluoro-2,2-dihydroxypropyl)benzamide (1.0 g, 3.74 mmol) and 2-methoxybenzyl amine (0.769 g, 5.61 mmol) following the experimental procedure described in step-5 of Example 2D.

Yield: 0.12 g (9.2%).

$^1$H NMR (400 MHz, CDCl$_3$): δ 7.62 (brs, 1H), 7.47-7.44 (m, 2H), 7.29-7.26 (m, 1H), 7.06-7.02 (m, 2H), 6.89 (t, J=8.0 Hz, 2H), 6.56 (d, J=7.6 Hz, 1H), 5.27 (s, 2H), 3.81 (s, 3H).

$^{19}$F NMR (400 MHz, CDCl$_3$): δ −110.50, −59.24

LCMS (ESI+, m/z): 350.9 (M+H)$^+$.

Step-6: Synthesis of 2-((2-(4-fluorophenyl)-5-(trifluoromethyl)-1H-imidazol-1-yl)methyl)phenol

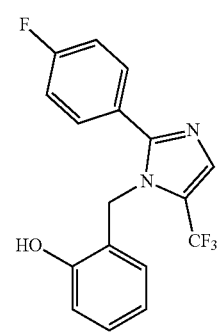 [SMILES: Oc1ccccc1Cn1c(C(F)(F)F)cnc1-c1ccc(F)cc1]

The title compound was synthesized from 2-(4-fluorophenyl)-1-(2-methoxybenzyl)-5-(trifluoromethyl)-1H-imidazole (0.12 g, 0.34 mmol) following the experimental procedure described in step-12 of Example 2A.

Yield: 0.10 g (crude).

$^1$H NMR (400 MHz, DMSO-d$_6$): δ 9.85 (brs, 1H), 8.06 (brs, 1H), 7.64 (dd, J=5.2 Hz, 2H), 7.35 (t, J=8.8 Hz, 2H), 7.08 (t, J=7.6 Hz, 1H), 6.80-6.68 (m, 2H), 6.45 (t, J=8.0 Hz, 1H), 5.27 (s, 2H).

$^{19}$F NMR (400 MHz, DMSO-d$_6$): δ −109.0, −58.20.

LCMS (ESI+, m/z): 337.2 (M+H)$^+$.

Step-7: Synthesis of ethyl (3R)-6-(2-((2-(4-fluorophenyl)-5-(trifluoromethyl)-1H-imidazol-1-yl)methyl)phenoxy)-3-methylhexanoate

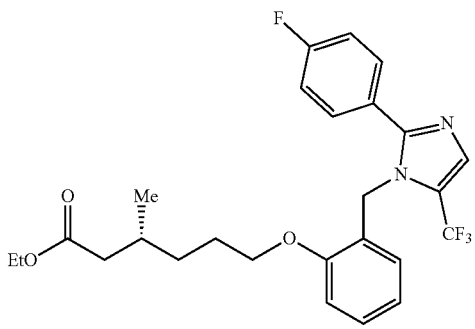

The title compound was synthesized from 2-((2-(4-fluorophenyl)-5-(trifluoromethyl)-1H-imidazol-1-yl)methyl)phenol (0.1 g, 0.29 mmol) and ethyl (3R)-6-bromo-3-methylhexanoate (0.14 g, 0.59 mmol) following the experimental procedure described in step-13 of Example 2A.

Yield: 0.05 g (34.2%).

LCMS (ESI+, m/z): 492.9 (M+H)$^+$.

Step-8: Synthesis (3R)-6-(2-((2-(4-fluorophenyl)-5-(trifluoromethyl)-1H-imidazol-1-yl)methyl)phenoxy)-3-methylhexanoic acid

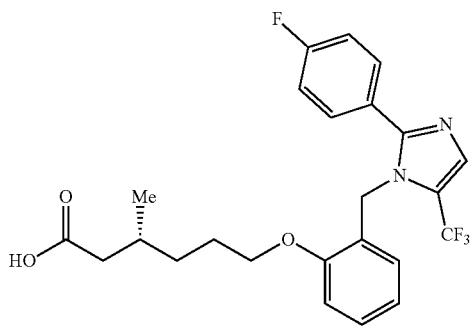 [SMILES: C[C@H](CCCOc1ccccc1Cn1c(C(F)(F)F)cnc1-c1ccc(F)cc1)CC(=O)O]

The title compound was synthesized from ethyl (3R)-6-(2-((2-(4-fluorophenyl)-5-(trifluoromethyl)-1H-imidazol-1-yl)methyl)phenoxy)-3-methylhexanoate (0.62 g, 1.25 mmol) following the experimental procedure described in step-14 of Example 2A.

Yield: 0.018 g (38.3%).

$^1$H NMR (400 MHz, CD$_3$OD): δ 7.64 (brs, 1H), 7.48-7.45 (m, 2H), 7.21 (t, J=7.2 Hz, 1H), 7.14-7.09 (m, 2H), 6.91 (d, J=8.0 Hz, 1H), 6.82 (t, J=7.6 Hz, 1H), 6.49 (d, J=7.2 Hz, 1H), 5.31 (s, 2H), 3.95 (t, J=6.0 Hz, 2H), 2.28-2.23 (m, 1H), 2.13-2.06 (m, 1H), 1.94-1.93 (m, 1H), 1.75-1.71 (m, 2H), 1.44 (m, 1H), 1.31-1.26 (m, 1H), 0.94 (d, J=6.8 Hz, 3H).

$^{19}$F NMR (400 MHz, CD$_3$OD): δ −112.00, −60.62.

LCMS (ESI+, m/z): 465.3 (M+H)$^+$.

HPLC: 93.72% (210 nm).

Example 2F: Synthesis of Compound 2f

Synthesis of (R)-6-(2-((2-(4-cyanophenyl)-5-(trifluoromethyl)-1H-imidazol-1-yl)methyl) phenoxy)-3-methylhexanoic acid

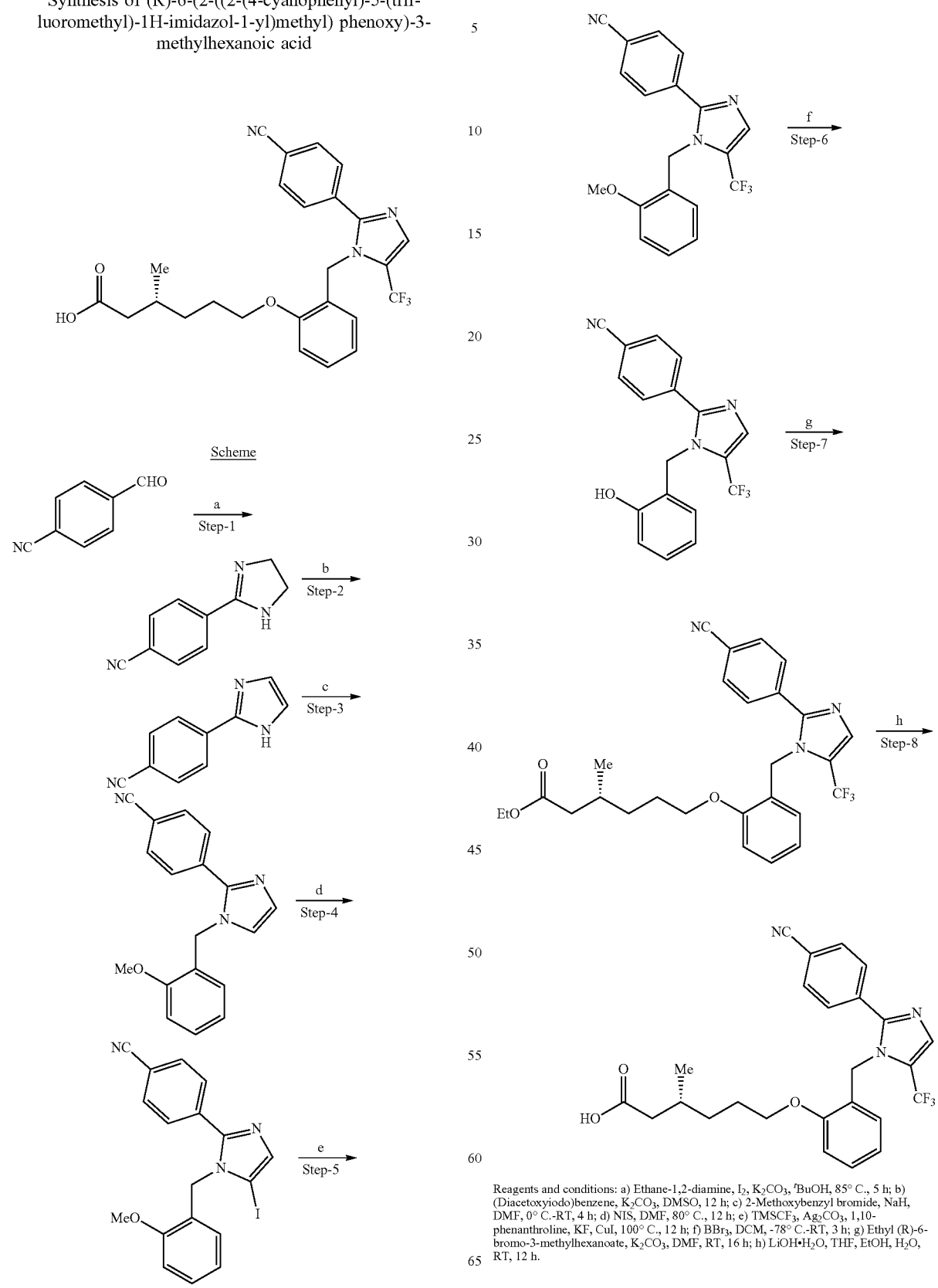

Reagents and conditions: a) Ethane-1,2-diamine, I$_2$, K$_2$CO$_3$, $^t$BuOH, 85° C., 5 h; b) (Diacetoxyiodo)benzene, K$_2$CO$_3$, DMSO, 12 h; c) 2-Methoxybenzyl bromide, NaH, DMF, 0° C.-RT, 4 h; d) NIS, DMF, 80° C., 12 h; e) TMSCF$_3$, Ag$_2$CO$_3$, 1,10-phenanthroline, KF, CuI, 100° C., 12 h; f) BBr$_3$, DCM, -78° C.-RT, 3 h; g) Ethyl (R)-6-bromo-3-methylhexanoate, K$_2$CO$_3$, DMF, RT, 16 h; h) LiOH•H$_2$O, THF, EtOH, H$_2$O, RT, 12 h.

Step-1: Synthesis of 4-(4,5-dihydro-1H-imidazol-2-yl)benzonitrile

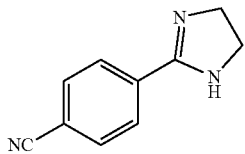 [SMILES: N#Cc1ccc(C2=NCCN2)cc1]

In a 1000 mL round bottom flask, a stirred solution of 4-formylbenzonitrile (25.0 g, 190.65. mmol) and ethane-1,2-diamine (12.60 g, 209.7 mmol) in $^t$BuOH (250 mL) was stirred for 30 min at RT under nitrogen atmosphere. Iodine (58.11 g, 228.78 mmol) and $K_2CO_3$ (79.04 g, 571.95 mmol) were sequentially added and reaction mixture was heated at 85° C. for 5 h under nitrogen atmosphere. Upon completion of reaction (TLC), the reaction mixture was quenched with saturated $Na_2S_2O_3$ solution and extracted with ethyl acetate (100 mL×3).

The combined organic extract was washed with brine, dried over anhydrous $Na_2SO_4$. and concentrated under reduced pressure to give title compound as a yellow solid, which was taken to next step without any purification. (24.0 g, 73.5%).

LCMS (ESI+, m/z): 172.2 (M+H)$^+$.

Step-2: Synthesis of 4-(1H-imidazol-2-yl)benzonitrile

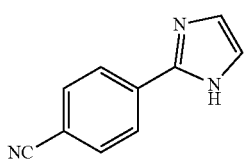 [SMILES: N#Cc1ccc(-c2ncc[nH]2)cc1]

In a 1000 mL round bottom flask, a stirred solution 4-(4,5-dihydro-1H-imidazol-2-yl)benzonitrile (24.0 g, 140.18 mmol) in DMSO (400 mL) was treated with $K_2CO_3$ (23.24 g, 168.21 mmol) and (diacetoxyiodo)benzene (54.18 g, 168.21 mmol) at RT under nitrogen atmosphere. The reaction was stirred at RT for 12 h under nitrogen atmosphere. Upon completion of reaction (TLC), the reaction mixture was diluted with ice cold water and extracted with ethyl acetate (200 mL×3). The combined organic extract was washed with brine, dried over anhydrous $Na_2SO_4$ and concentrated under reduced pressure. The residue obtained was purified by silica gel column chromatography (gradient elution, 40% EtOAc in hexanes) to afford the title compound as a yellow solid (18.5 g, 78.0%)

$^1$H NMR (400 MHz, DMSO-$d_6$): δ 12.81 (brs, 1H), 8.09 (d, J=8.8 Hz, 2H), 7.90 (d, J=8.4 Hz, 2H), 7.36 (bs, 1H), 7.12 (brs, 1H).

LCMS (ESI+, m/z): 170.3 (M+H)$^+$.

Step-3: Synthesis of 4-(1-(2-methoxybenzyl)-1H-imidazol-2-yl)benzonitrile

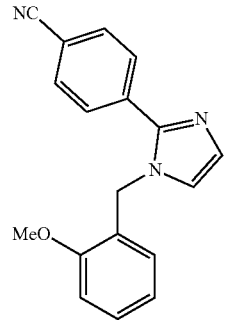

In a 500 mL round bottom flask, a stirred solution 4-(1H-imidazol-2-yl)benzonitrile (10 g, 59.10 mmol) in DMF (100 mL) was treated with NaH (60%, 4.72 g, 118.20 mmol) at 0° C. under nitrogen atmosphere. The reaction mixture was stirred for 30 min at same temperature under nitrogen atmosphere. The mixture was treated with 2-methoxybenzyl bromide (15.48 g, 76.83 mmol) and resulting reaction mixture was stirred for 4 h at RT under nitrogen atmosphere. Upon completion of reaction (TLC), the reaction mixture was quenched with saturated $NH_4Cl$ solution and extracted with ethyl acetate (300 mL×3). The combined organic extract was washed with brine, dried over anhydrous $Na_2SO_4$ and concentrated under reduced pressure. The residue obtained was purified by silica gel column chromatography (gradient elution, 20% EtOAc in hexanes) to afford the title compound as a white solid (9.1 g, 53.2%)

$^1$H NMR (400 MHz, CDCl$_3$): δ 7.72-7.64 (m, 4H), 7.32 (t, J=7.6 Hz, 1H), 7.22 (s, 1H), 7.02 (s, 1H), 6.94-6.90 (m, 2H), 6.81 (d, J=6.8 Hz, 1H), 5.22 (s, 2H), 3.81 (s, 3H).

LCMS (ESI+, m/z): 290.3 (M+H)$^+$.

Step-4: Synthesis of 4-(5-iodo-1-(2-methoxybenzyl)-1H-imidazol-2-yl)benzonitrile

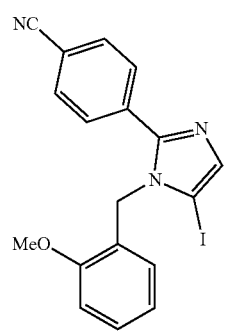

In a 250 mL round bottom flask, a stirred solution of 4-(1-(2-methoxybenzyl)-1H-imidazol-2-yl)benzonitrile (5 g, 17.30 mmol) in DMF (60 mL) was treated with NIS (3.89 g, 17.30 mmol) at RT. The reaction mixture was heated at 80° C. for 12 h. Upon completion of reaction (TLC), the reaction mixture was quenched with saturated $Na_2S_2O_3$ solution and extracted with ethyl acetate (100 mL×3). The combined organic extract was washed with brine, dried over anhydrous $Na_2SO_4$ and concentrated under reduced pressure. The residue obtained was purified by silica gel column chromatography (gradient elution, 7-8% EtOAc in hexanes) to afford the title compound as a white solid (1.41 g, 19.8%)
$^1H$ NMR (300 MHz, $CDCl_3$): δ 7.64-7.56 (m, 4H), 7.38 (s, 1H), 7.32 (t, J=8.1 Hz, 1H), 6.95-6.89 (m, 2H), 6.56 (d, J=7.5 Hz, 1H), 5.22 (s, 2H), 3.87 (s, 3H).

LCMS (ESI+, m/z): 415.6 (M+H)+.

Step-5: Synthesis of 4-(1-(2-methoxybenzyl)-5-(trifluoromethyl)-1H-imidazol-2-yl)benzonitrile

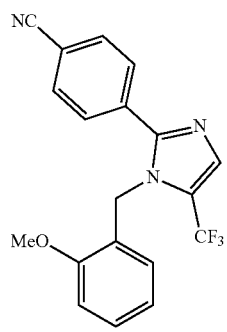 [SMILES: COc1ccccc1Cn1c(C(F)(F)F)cnc1-c1ccc(C#N)cc1]

In a 100 mL re-sealable reaction tube, a stirred solution 4-(5-iodo-1-(2-methoxybenzyl)-1H-imidazol-2-yl)benzonitrile (2.5 g, 6.02 mmol) in DMF (15 mL) was degassed by purging with argon gas for 5 min at RT. $Ag_2CO_3$ (3.31 g, 12.04 mmol), KF (1.047 g, 18.06 mmol), 1,10-phenanthroline (1.08 g, 6.02 mmol), CuI (1.143 g, 6.02 mmol) were sequentially added to the above mixture under nitrogen atmosphere. The resulting mixture was cooled to 0° C. and treated with $TMSCF_3$ (2.56 g, 18.06 mmol) dropwise under nitrogen atmosphere. The reaction mixture was heated at 100° C. for 12 h under nitrogen atmosphere and treated with additional quantity of $TMSCF_3$ (1.28 g, 9.03 mmol) to ensure completion of reaction (TLC). The reaction mixture was cooled to RT and diluted with ethyl acetate (30 mL) before filtering over Celite® bed. The solid residue was washed with ethyl acetate (20 mL×2). The combined filtrate was washed with water, brine, dried over anhydrous $Na_2SO_4$ and concentrated under reduced pressure. The residue obtained was purified by silica gel column chromatography (gradient elution, 3-5% EtOAc in hexanes) to afford the title compound as a clear oil (1.73 g, 74.4%).

$^1H$ NMR (400 MHz, $CDCl_3$): δ 7.67-7.60 (m, 5H), 7.32 (t, J=8.4 Hz, 1H), 6.96-6.89 (m, 2H), 6.57 (d, J=7.2 Hz, 1H), 5.33 (s, 2H), 3.85 (s, 3H).

$^{19}F$ NMR (400 MHz, $CDCl_3$): δ -59.25.

LCMS (ESI+, m/z): 358.8 (M+H)+.

Step-6: Synthesis of 4-(1-(2-hydroxybenzyl)-5-(trifluoromethyl)-1H-imidazol-2-yl)benzonitrile

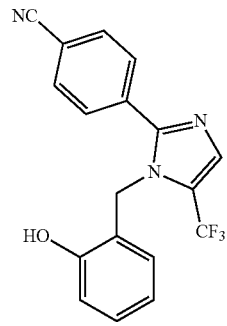 [SMILES: N#Cc1ccc(-c2ncc(C(F)(F)F)n2Cc2ccccc2O)cc1]

In a 1000 mL round bottom flask, a solution of 4-(1-(2-methoxybenzyl)-5-(trifluoromethyl)-1H-imidazol-2-yl) benzonitrile (1.5 g, 4.20 mmol) in dichloromethane (15 mL) was treated with $BBr_3$ (1.5 mL) dropwise at −78° C. under nitrogen atmosphere. The reaction mixture was stirred at RT for 3 h. Upon completion of reaction (TLC), the reaction mixture was basified with aqueous $NaHCO_3$ and extracted with DCM (30 mL×2). The combined organic extract was separated and washed with brine, dried over anhydrous $Na_2SO_4$ and concentrated under reduced pressure. The residue obtained was washed with n-hexane (3×10 mL) and dried under reduced pressure to afford the title compound (1.13 g).

LCMS (ESI+, m/z): 344.4 (M+H)+.

Step-7: Synthesis of ethyl(R)-6-(2-((2-(4-cyanophenyl)-5-(trifluoromethyl)-1H-imidazol-1-yl)methyl) phenoxy)-3-methylhexanoate

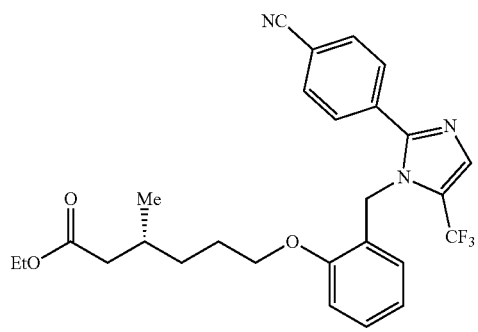

In a 250 mL round bottom flask, a stirred solution of 4-(1-(2-hydroxybenzyl)-5-(trifluoromethyl)-1H-imidazol-2-yl)benzonitrile (1.0 g, 2.91 mmol) in DMF (5 mL) was treated with $K_2CO_3$ (1.2 g, 8.73 mmol) and ethyl (R)-6-bromo-3-methylhexanoate (1.37 g, 5.83 mmol) at RT under nitrogen atmosphere. The resulting reaction mixture was stirred at RT for 16 h. Upon completion of the reaction (TLC), the reaction mixture was diluted with cold water (50 mL), before extracting with ethyl acetate (50 mL). The organic extract was washed with brine, dried over anhydrous $Na_2SO_4$ and concentrated under reduced pressure. The residue obtained was purified by purified by preparative HPLC [Column: GEMINI NX C18, 21.2 mm×150 mm); Flow: 20 mL/min; mobile phase: A/B=0.05% TFA in water/MeCN-MeOH (2:1); T/% B=0/40, 2/50, 5/80] to afford the title compound.

$^1$H NMR (300 MHz, CDCl$_3$): δ 7.65-7.63 (m, 5H), 7.30-7.26 (m, 1H), 6.90-6.85 (m, 2H), 6.54 (d, J=7.8 Hz, 1H), 5.31 (s, 2H), 4.12 (q, J=6.9 Hz, 2H), 3.98 (t, J=6.3 Hz, 2H), 2.32-2.25 (m, 1H), 2.18-2.10 (s, 1H), 2.09-1.86 (m, 1H), 1.77-1.65 (m, 2H), 1.51-1.42 (m, 1H), 1.35-1.26 (m, 1H), 1.24 (t, J=6.9 Hz, 3H), 0.96 (d, J=6.3 Hz, 3H).

$^{19}$F NMR (300 MHz, CDCl$_3$): δ −59.27.

LCMS (ESI+, m/z): 500.5 (M+H)$^+$.

Step-8: Synthesis of (R)-6-(2-((2-(4-cyanophenyl)-5-(trifluoromethyl)-1H-imidazol-1-yl)methyl)phenoxy)-3-methylhexanoic acid

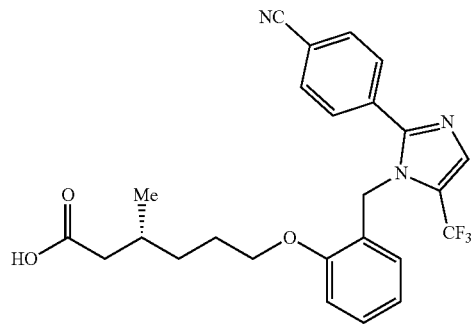

In a 500 mL round bottom flask, a stirred solution of ethyl (R)-6-(2-((2-(4-cyanophenyl)-5-(trifluoromethyl)-1H-imidazol-1-yl)methyl)phenoxy)-3-methylhexanoate (140 mg, 0.280 mmol) in THF (5 mL) and water (5 mL), was treated with lithium hydroxide monohydrate (14.0 g, 0.336 mmol) at RT. The reaction mixture was stirred at RT for 12 h. Upon completion of reaction (TLC), the reaction mixture was diluted with water and washed with diethyl ether. The aqueous layer was acidified with 1 N HCl, and extracted with ethyl acetate (50 mL). The organic extract was washed with brine, dried over anhydrous Na$_2$SO$_4$ and concentrated under reduced pressure. The residue obtained was purified by preparative HPLC (Kinetex C18, 21.2 mm×150 mm; flow: 18.0 mL/min; mobile phase: A/B=water: MeCN, T/% B=0/10, 2/20/8/80) to afford the title compound (81 mg, 61.8%).

$^1$H NMR (400 MHz, CD$_3$OD): δ 7.75 (d, J=8.4 Hz, 2H), 7.71 (s, 1H), 7.66 (d, J=8.4 Hz, 2H), 7.23 (t, J=7.2 Hz, 1H), 6.92 (d, J=8.4 Hz, 1H), 6.82 (t, J=8.4 Hz, 1H), 6.52 (d, J=7.2 Hz, 1H), 5.38 (s, 2H), 3.96 (t, J=6.0 Hz, 2H), 2.31-2.26 (m, 1H), 2.13-2.07 (m, 1H), 2.03-1.91 (m, 1H), 1.79-1.71 (m, 2H), 1.47-1.44 (m, 1H), 1.34-1.28 (m, 1H), 0.96 (d, J=6.8 Hz, 3H).

$^1$H NMR (400 MHz, CD$_3$OD): δ −60.58

LCMS (ESI+, m/z): 472.4 (M+H)$^+$.

HPLC: 92.02% (210 nm).

Example 2G: Synthesis of Compound 2

Synthesis of (3R)-3-methyl-6-(2-((2-(4-(trifluoromethoxy)phenyl)-5-(trifluoromethyl)-1H-imidazol-1-yl)methyl)phenoxy)hexanoic acid

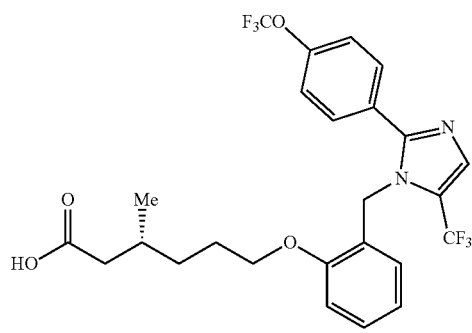

Scheme

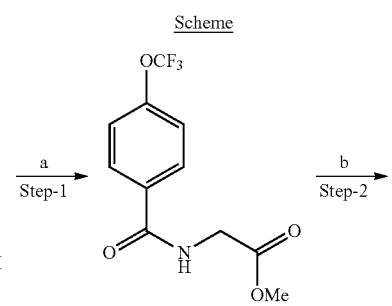

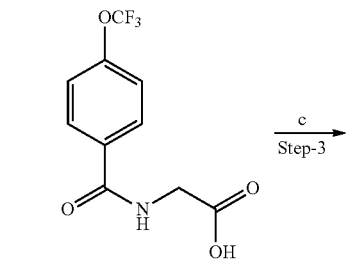

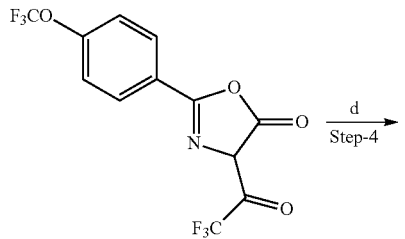

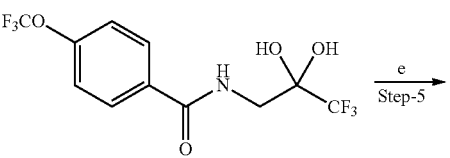

61
-continued

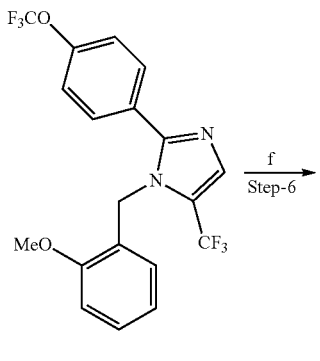

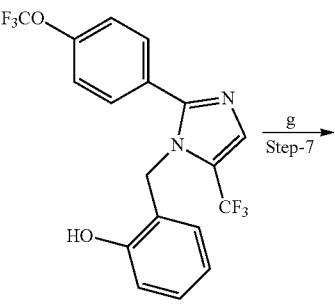

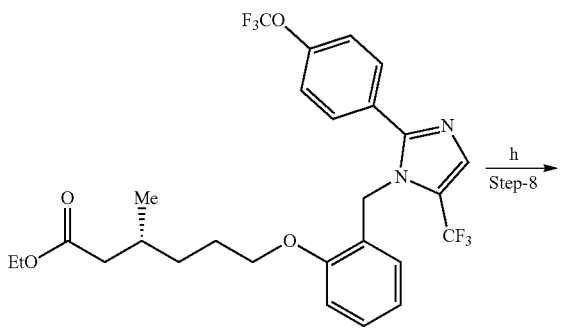

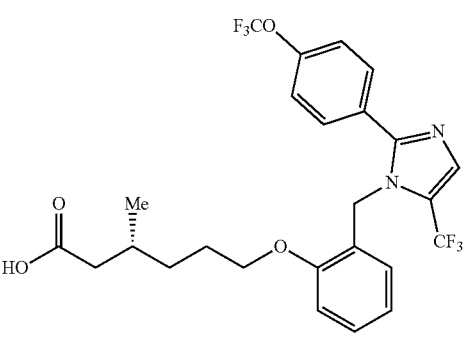

Reagents and conditions: a) Methyl glycinate hydrochloride, EDCI•HCl, HOBt, Et₃N, DMF, RT, 12 h; b) LiOH•H₂O, THF, EtOH, H₂O, RT, 12 h;
c) 2,2,2-Trifluoroacetic anhydride, acetone, 0° C.-RT, 12 h; d) 1,4-Dioxane-H₂O, 100° C., 3 h; e) 2-Methoxybenzyl amine, AcOH, toluene, 120° C., 12 h; f) BBr₃, DCM, 0° C.-RT, 3 h; g) Ethyl (3R)-6-bromo-3-methylhexanoate, K₂CO₃, DMF, RT, 12 h; h) LiOH•H₂O, THF, EtOH, H₂O, RT, 12 h.

62

Step-1: Synthesis of methyl (4-(trifluoromethoxy)benzamido)acetate

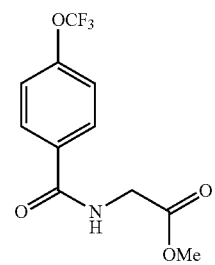 [SMILES: COC(=O)CNC(=O)c1ccc(OC(F)(F)F)cc1]

The title compound was synthesized from 4-(trifluoromethoxy)benzoic acid (10.0 g, 48.53 mmol) and methyl glycinate hydrochloride (9.13 g, 72.80 mmol) following the experimental procedure described in step-1 of Example 2D.

Yield: 9.8 g (72.8%).

$^1$H NMR (300 MHz, CDCl₃): δ 7.86 (d, J=6.9 Hz, 2H), 7.28 (d, J=6.9 Hz, 2H), 6.72 (brs, 1H), 4.25 (d, J=5.4 Hz, 2H), 3.81 (s, 3H).

$^{19}$F NMR (300 MHz, CDCl₃): δ −57.73

LCMS (ESI+, m/z): 277.6 (M+H)⁺.

Step-2: Synthesis of (4-(trifluoromethoxy)benzoyl)glycine

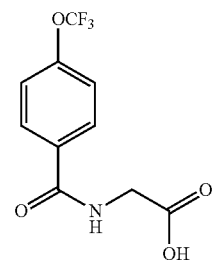 [SMILES: O=C(O)CNC(=O)c1ccc(OC(F)(F)F)cc1]

The title compound was synthesized from methyl (4-(trifluoromethoxy)benzamido)acetate (9.8 g, 35.35 mmol) following the experimental procedure described in step-2 of Example 2D.

Yield: 7.5 g (80.6%).

$^1$H NMR (300 MHz, DMSO-d₆): δ 12.73 (brs, 1H), 8.97 (t, J=5.4 Hz, 1H), 7.98 (d, J=8.7 Hz, 2H), 7.47 (d, J=8.1 Hz, 2H), 3.91 (d, J=6.0 Hz, 2H).

$^{19}$F NMR (300 MHz, DMSO-d₆): δ −56.69.

LCMS (ESI+, m/z): 263.6 (M+H)⁺.

Step-3: Synthesis of 4-(2,2,2-trifluoroacetyl)-2-(4-(trifluoromethoxy)phenyl)oxazol-5 (4H)-one

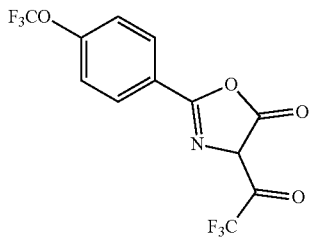 [SMILES: O=C1OC(c2ccc(OC(F)(F)F)cc2)=NC1C(=O)C(F)(F)F]

The title compound was synthesized from of (4-(trifluoromethoxy)benzoyl)glycine (1.0 g, 3.80 mmol) following the experimental procedure described in step-3 of Example 2D.

Yield: 1.1 g.
$^1$H NMR (400 MHz, DMSO-$d_6$): δ 7.99 (d, J=8.8 Hz, 1H), 7.81 (d, J=8.8 Hz, 1H), 7.50 (d, J=8.4 Hz, 1H), 7.40 (d, J=8.4 Hz, 1H).

Step-4: Synthesis of N-(3,3,3-trifluoro-2,2-dihydroxypropyl)-4-(trifluoromethoxy) benzamide

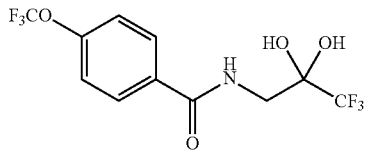 [SMILES: O=C(NCC(O)(O)C(F)(F)F)c1ccc(OC(F)(F)F)cc1]

The title compound was synthesized from 4-(2,2,2-trifluoroacetyl)-2-(4-(trifluoromethoxy)phenyl)oxazol-5 (4H)-one (1.0 g, 4.14 mmol) following the experimental procedure described in step-4 of Example 2D.

Yield: 0.92 g.
LCMS (ESI+, m/z): 333.9 (M+H)$^+$.

Step-5: Synthesis of 1-(2-methoxybenzyl)-2-(4-(trifluoromethoxy)phenyl)-5-(trifluoromethyl)-1H-imidazole

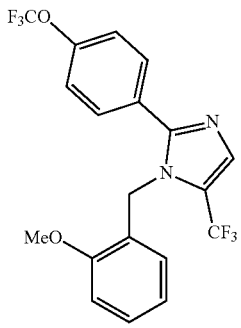 [SMILES: COc1ccccc1Cn1c(C(F)(F)F)cnc1-c1ccc(OC(F)(F)F)cc1]

The title compound was synthesized from N-(3,3,3-trifluoro-2,2-dihydroxypropyl)-4-(trifluoromethoxy)benzamide (0.9 g, 2.83 mmol) and 2-methoxybenzyl amine (2.33 mL, 17.03 mmol) following the experimental procedure described in step-5 of Example 2D.

Yield: 0.14 g (13.4%).
$^1$H NMR (300 MHz, CDCl$_3$): δ 7.64 (brs, 1H), 7.55-7.52 (m, 2H), 7.21 (d, J=8.1 Hz, 2H), 6.90 (d, J=8.1 Hz, 2H), 6.59 (d, J=6.9 Hz, 2H), 5.31 (s, 2H), 3.84 (s, 3H).
LCMS (ESI+, m/z): 416.9 (M+H)$^+$.

Step-6: Synthesis of 2-((2-(4-(trifluoromethoxy)phenyl)-5-(trifluoromethyl)-1H-imidazol-1-yl)methyl)phenol

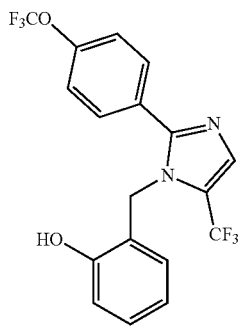 [SMILES: Oc1ccccc1Cn1c(C(F)(F)F)cnc1-c1ccc(OC(F)(F)F)cc1]

The title compound was synthesized from 1-(2-methoxybenzyl)-2-(4-(trifluoromethoxy)phenyl)-5-(trifluoromethyl)-1H-imidazole (0.14 g, 0.33 mmol) following the experimental procedure described in step-12 of Example 2A.

Yield: 0.115 g (crude).
$^1$H NMR (400 MHz, DMSO-$d_6$): δ 9.80 (brs, 1H), 7.84 (s, 1H), 7.68 (d, J=8.8 Hz, 2H), 7.43 (d, J=8.0 Hz, 2H), 7.06-7.02 (m, 1H), 6.79-6.64 (m, 1H), 6.59 (t, J=6.9 Hz, 1H), 6.32 (d, J=7.6 Hz, 1H), 5.24 (s, 2H).

Step-7: Synthesis of ethyl(3R)-3-methyl-6-(2-((2-(4-(trifluoromethoxy)phenyl)-5-(trifluoromethyl)-1H-imidazol-1-yl)methyl)phenoxy)hexanoate

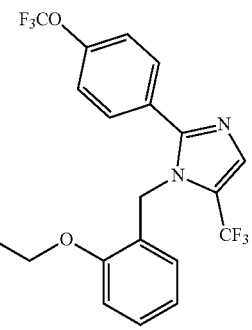

The title compound was synthesized from 2-((2-(4-(trifluoromethoxy)phenyl)-5-(trifluoromethyl)-1H-imidazol-1-yl)methyl)phenol (0.110 g, 0.27 mmol) and ethyl (3R)-6-bromo-3-methylhexanoate (0.185 g, 0.81 mmol) following the experimental procedure described in step-13 of Example 2A.

Yield: 0.075 g.
LCMS (ESI+, m/z): 558.8 (M+H)$^+$.

Step-8: Synthesis (3R)-3-methyl-6-(2-((2-(4-(trifluoromethoxy)phenyl)-5-(trifluoromethyl)-1H-imidazol-1-yl)methyl)phenoxy)hexanoic acid

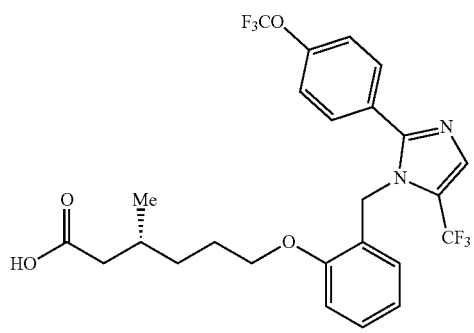 [SMILES: C[C@H](CCCOc1ccccc1Cn1c(C(F)(F)F)cnc1-c1ccc(OC(F)(F)F)cc1)CC(=O)O]

The title compound was synthesized from ethyl (3R)-3-methyl-6-(2-((2-(4-(trifluoromethoxy)phenyl)-5-(trifluoromethyl)-1H-imidazol-1-yl)methyl)phenoxy)hexanoate (0.07 g, 0.12 mmol) following the experimental procedure described in step-14 of Example 2A. The compound was purified by reverse phase preparative HPLC conditions [EVO C18 (21.2 mm×150 mm, 5μ; flow: 15 mL/min; mobile phase: A/B=0.1% TFA water/MeCN; Time/% B in mobile phase=0/40, 2/45, 10/70]

Yield: 0.021 g (31.8%).

$^1$H NMR (400 MHz, DMSO-d$_6$): δ 12.10 (brs, 1H), 7.77 (s, 1H), 7.68-7.66 (m, 2H), 7.42 (d, J=8.0 Hz, 2H), 7.21 (t, J=6.8 Hz, 1H), 6.96 (d, J=8.4 Hz, 1H), 6.82 (t, J=7.2 Hz, 1H), 6.42 (d, J=7.2 Hz, 1H), 5.31 (s, 2H), 3.93 (t, J=6.4 Hz, 2H), 2.34-2.29 (m, 1H), 2.01-1.95 (m, 1H), 1.86-1.84 (m, 1H), 1.66-1.63 (m, 2H), 1.48-1.46 (m, 1H), 1.30-1.23 (m, 1H), 0.87 (d, J=6.4 Hz, 3H).

$^{19}$F NMR (400 MHz, CDCl$_3$): δ −57.80, −59.25

LCMS (ESI+, m/z): 531.0 (M+H)$^+$.

HPLC: 95.19% (210 nm).

Example 2H: Synthesis of Compound 2h

Synthesis of 6-(2-((2-(4-(furan-2-yl)phenyl)-5-(trifluoromethyl)-1H-imidazol-1-yl)methyl)phenoxy)hexanoic acid

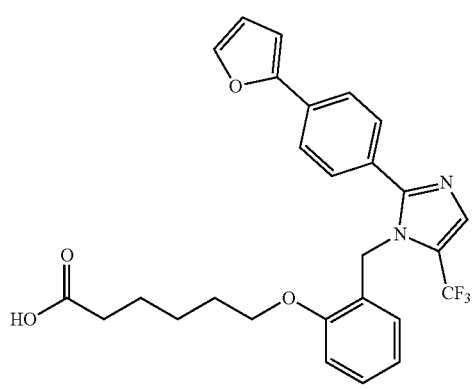 [SMILES: O=C(O)CCCCCOc1ccccc1Cn1c(C(F)(F)F)cnc1-c1ccc(-c2ccco2)cc1]

Scheme

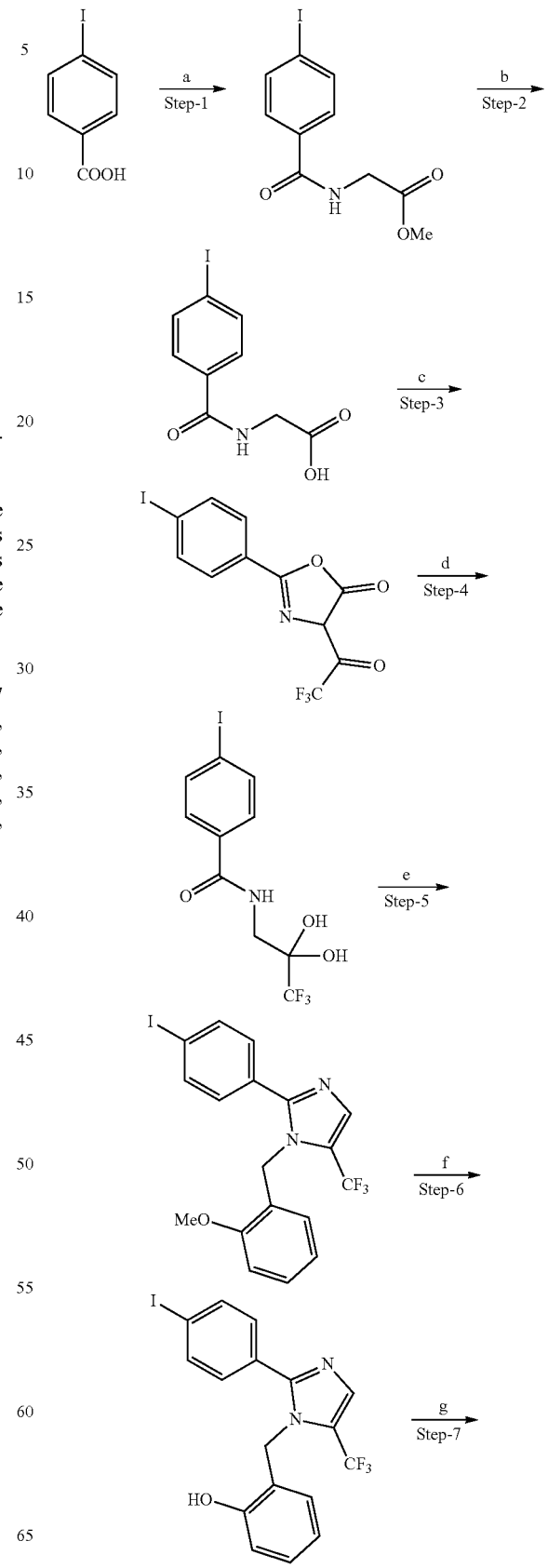

-continued

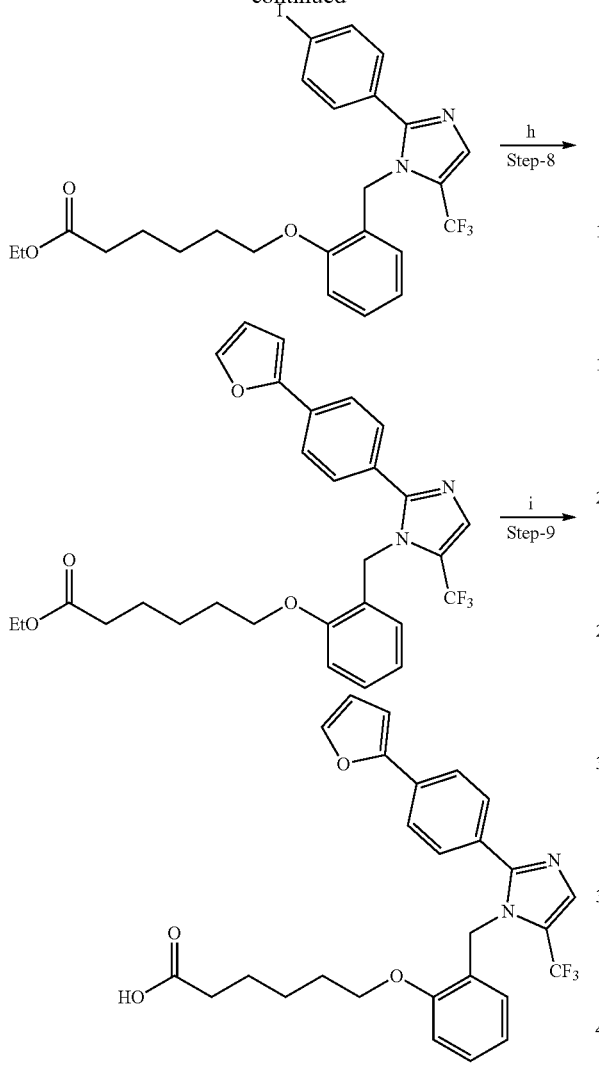

Reagents and conditions: a) Methyl glycinate hydrochloride, EDCI•HCl, HOBt, Et₃N, DMF, 12 h; b) LiOH•H₂O, THF, EtOH, H₂O, RT, 12 h; c) 2,2,2-Trifluoroacetic anhydride, acetone, 0° C.- RT, 12 h; d) 1,4-Dioxane, H₂O, 100° C., 3 h; e) 2-Methoxybenzyl amine, AcOH, toluene, 120° C., 12 h; f) BBr₃, DCM, -78° C.; g) Ethyl 6-bromohexanoate, K₂CO₃, DMF, RT, 12 h; h) Furan-2-boronic acid, Pd(PPh₃)₄, Na₂CO₃, DME, EtOH, H₂O, 90° C., 12 h; i) LiOH•H₂O, THF, EtOH, H₂O, RT, 12 h.

Step-1: Synthesis of methyl (4-iodobenzamido)acetate

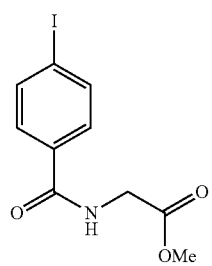 [SMILES: COC(=O)CNC(=O)c1ccc(I)cc1]

The title compound was synthesized from 4-iodobenzoic acid (20.0 g, 142.74 mmol) and methyl glycinate hydrochloride (26.87 g, 214.11 mmol) following the experimental procedure described in step-1 of Example 2D.

Yield: (21.1 g, 81.6%)
LCMS (ESI+, m/z): 319.9 (M+H)⁺.

Step-2: Synthesis of (4-iodobenzoyl)glycine

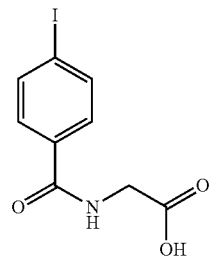 [SMILES: O=C(O)CNC(=O)c1ccc(I)cc1]

The title compound was synthesized from methyl (4-iodobenzamido)acetate (21 g, 65.83 mmol) following the experimental procedure described in step-2 of Example 2D.

Yield: (17.1 g, 84.7%).
¹H NMR (300 MHz, DMSO-d₆): δ 12.63 (brs, 1H), 8.93 (t, J=5.7 Hz, 1H), 7.89 (d, J=8.1 Hz, 2H), 7.65 (d, J=8.1 Hz, 2H), 3.91 (d, J=5.7 Hz, 2H).
LCMS (ESI+, m/z): 306.0 (M+H)⁺.

Step-3: Synthesis of 2-(4-iodophenyl)-4-(2,2,2-trifluoroacetyl)oxazol-5 (4H)-one

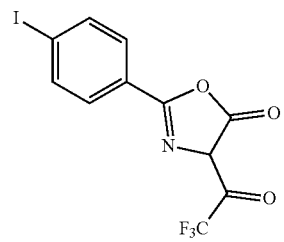

The title compound was synthesized from (4-iodobenzoyl)glycine (17 g, 55.73 mmol) and 2,2,2-trifluoroacetic anhydride (23.5 mL, 167.21 mmol) following the experimental procedure described in step-3 of Example 2D.

Yield: (11.7 g, 66.5%)
¹H NMR (400 MHz, DMSO-d₆): δ 7.87 (d, J=8.0 Hz, 1H), 7.77 (d, J=8.4 Hz, 1H), 7.63 (d, J=8.0 Hz, 1H), 7.49 (d, J=8.0 Hz, 1H).
LCMS (ESI-, m/z): 382.1 (M–H)⁺.

Step-4: Synthesis of 4-iodo-N-(3,3,3-trifluoro-2,2-dihydroxypropyl)benzamide

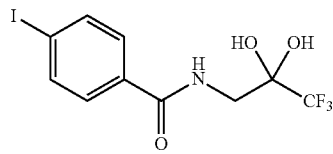 [SMILES: O=C(NCC(O)(O)C(F)(F)F)c1ccc(I)cc1]

The title compound was synthesized from 2-(4-iodophenyl)-4-(2,2,2-trifluoroacetyl)oxazol-5 (4H)-one (14 g, 36.55 mmol) following the experimental procedure described in step-4 of Example 2D.

Yield: 9.75 g (59.1%)

LCMS (ESI+, m/z): 376.1 (M+H)+.

Step-5: Synthesis of 2-(4-iodophenyl)-1-(2-methoxybenzyl)-5-(trifluoromethyl)-1H-imidazole

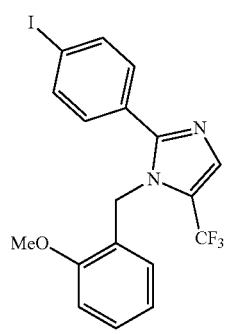

The title compound was synthesized from 4-iodo-N-(3,3,3-trifluoro-2,2-dihydroxypropyl)benzamide (3 g, 8.0 mmol) and 2-methoxy benzylamine (1.7 g, 12.0 mmol) following the experimental procedure described in step-5 of Example 2D.

Yield: 0.53 g (14.5%)

$^1$H NMR (300 MHz, CDCl$_3$): δ 7.69 (d, J=6.6 Hz, 2H), 7.06 (d, J=1.2 Hz, 1H), 7.30-7.27 (m, 1H), 7.2 (d, J=6.6 Hz, 2H), 6.90-6.85 (m, 2H), 6.53 (d, J=6.6 Hz, 1H), 5.27 (s, 2H), 3.81 (s, 3H).

LCMS (ESI+, m/z): 459.1 (M+H)+.

Step-6: Synthesis of 2-((2-(4-iodophenyl)-5-(trifluoromethyl)-1H-imidazol-1-yl)methyl)phenol

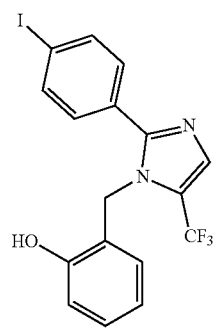 [SMILES: Oc1ccccc1Cn1c(C(F)(F)F)cnc1-c1ccc(I)cc1]

The title compound was synthesized from 2-(4-iodophenyl)-1-(2-methoxybenzyl)-5-(trifluoromethyl)-1H-imidazole (0.5 g, 1.09 mmol) following the experimental procedure described in step-12 of Example 2A.

Yield: 0.31 g (61.9%)

LCMS (ESI+, m/z): 444.8 (M+H)+.

Step-7: Synthesis of ethyl 6-(2-((2-(4-iodophenyl)-5-(trifluoromethyl)-1H-imidazol-1-yl)methyl)phenoxy)hexanoate

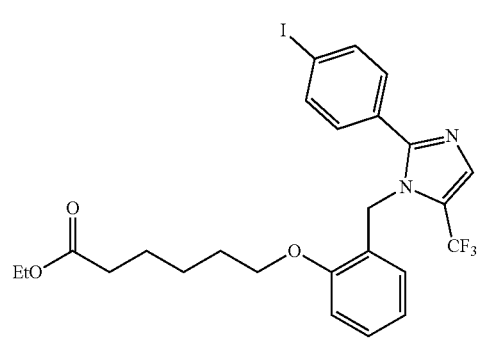 [SMILES: CCOC(=O)CCCCCOc1ccccc1Cn1c(C(F)(F)F)cnc1-c1ccc(I)cc1]

The title compound was synthesized from 2-((2-(4-iodophenyl)-5-(trifluoromethyl)-1H-imidazol-1-yl)methyl)phenol (0.15 g, 0.337 mmol) and ethyl 6-bromohexanoate (0.115 g, 0.506 mmol) following the experimental procedure described in step-13 of Example 2A.

Yield: 0.21 g

LCMS (ESI+, m/z): 586.9 (M+H)+.

Step-8: Synthesis of ethyl 6-(2-((2-(4-(furan-2-yl)phenyl)-5-(trifluoromethyl)-1H-imidazol-1-yl)methyl)phenoxy)hexanoate

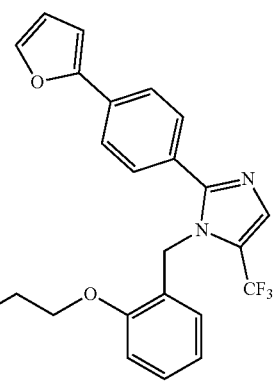

In a 100 mL resealable reaction tube, ethyl 6-(2-((2-(4-iodophenyl)-5-(trifluoromethyl)-1H-imidazol-1-yl)methyl)phenoxy)hexanoate (0.2 g, 0.341 mmol) and furan-2-boronic acid (0.075 g, 0.682 mmol) were dissolved in degassed solvent combination of DME (10 mL), EtOH (10 mL) and water (10 mL) at RT under nitrogen atmosphere. Pd(PPh$_3$)$_4$ (0.040 g, 0.0341 mmol), and Na$_2$CO$_3$ (0.110 g, 1.023 mmol) were added to the above solution under nitrogen atmosphere. The resulting mixture was degassed by purging argon gas for 15 min, and reaction mixture was heated to 90° C. until completion of the reaction (TLC). The reaction mixture was cooled to RT, diluted with cold water and extracted with ethyl acetate (3×30 mL). The combined extract was washed with brine, dried over anhydrous Na$_2$SO$_4$ and concentrated under reduced pressure to get the title compound.

Yield: 0.11 g (55.5%)

LCMS (ESI+, m/z): 527.3 (M+H)+.

Step-9: Synthesis of 6-(2-((2-(4-(furan-2-yl)phenyl)-5-(trifluoromethyl)-1H-imidazol-1-yl)methyl)phenoxy)hexanoic acid The title compound was synthesized from ethyl 6-(2-((2-(4-(furan-2-yl)phenyl)-5-(trifluoromethyl)-1H-imidazol-1-yl)methyl)phenoxy)hexanoate (0.14 g, 0.265 mmol) following the experimental procedure described in step-14 of Example 2A.

Yield: 0.03 g (23.1%)

$^1$H NMR (400 MHz, DMSO-$d_6$, 80° C.): δ 12.1 (brs, 1H), 7.76 (brs, 2H), 7.72 (d, J=8.4 Hz, 2H), 7.59 (d, J=8.4 Hz, 2H), 7.21 (t, J=7.6 Hz, 1H), 7.03 (d, J=3.2 Hz, 1H), 6.97 (d, J=8.0 Hz, 1H), 6.83 (t, J=8.0 Hz, 1H), 6.60-6.59 (m, 1H), 6.40 (d, J=7.2 Hz, 1H), 5.32 (s, 2H), 3.95 (t, J=6.0 Hz, 2H), 2.2-2.1 (m, 2H), 1.66-1.63 (m, 2H), 1.52-1.46 (m, 2H), 1.36-1.34 (m, 2H).

$^{19}$F NMR (400 MHz, DMSO-$d_6$): δ −57.85

LCMS (ESI+, m/z): 499.3 (M+H)$^+$.

HPLC: 98.97% (210 nm).

Example 21: Synthesis of Compound 2i

Synthesis of (3R)-6-(2-((2-(4-(furan-2-yl)phenyl)-5-(trifluoromethyl)-1H-imidazol-1-yl)methyl)phenoxy)-3-methylhexanoic acid Scheme

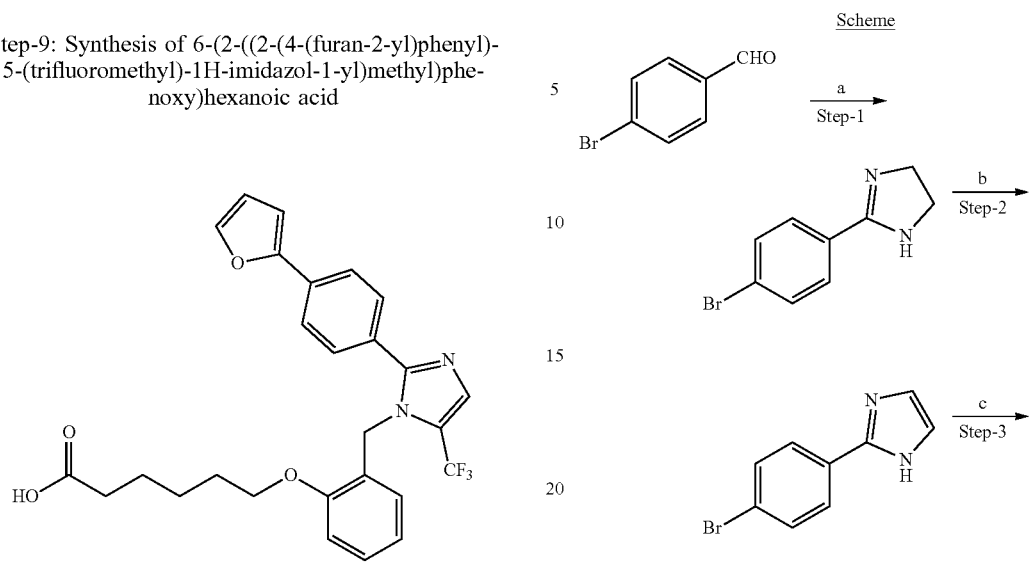

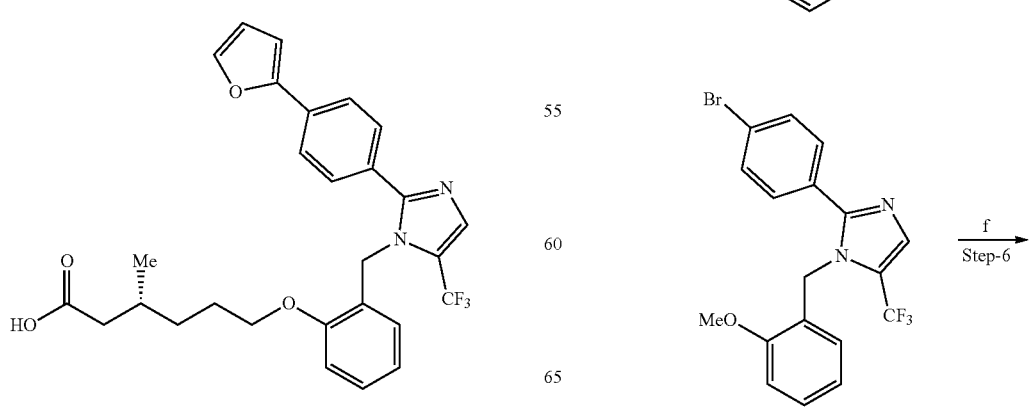

73
-continued

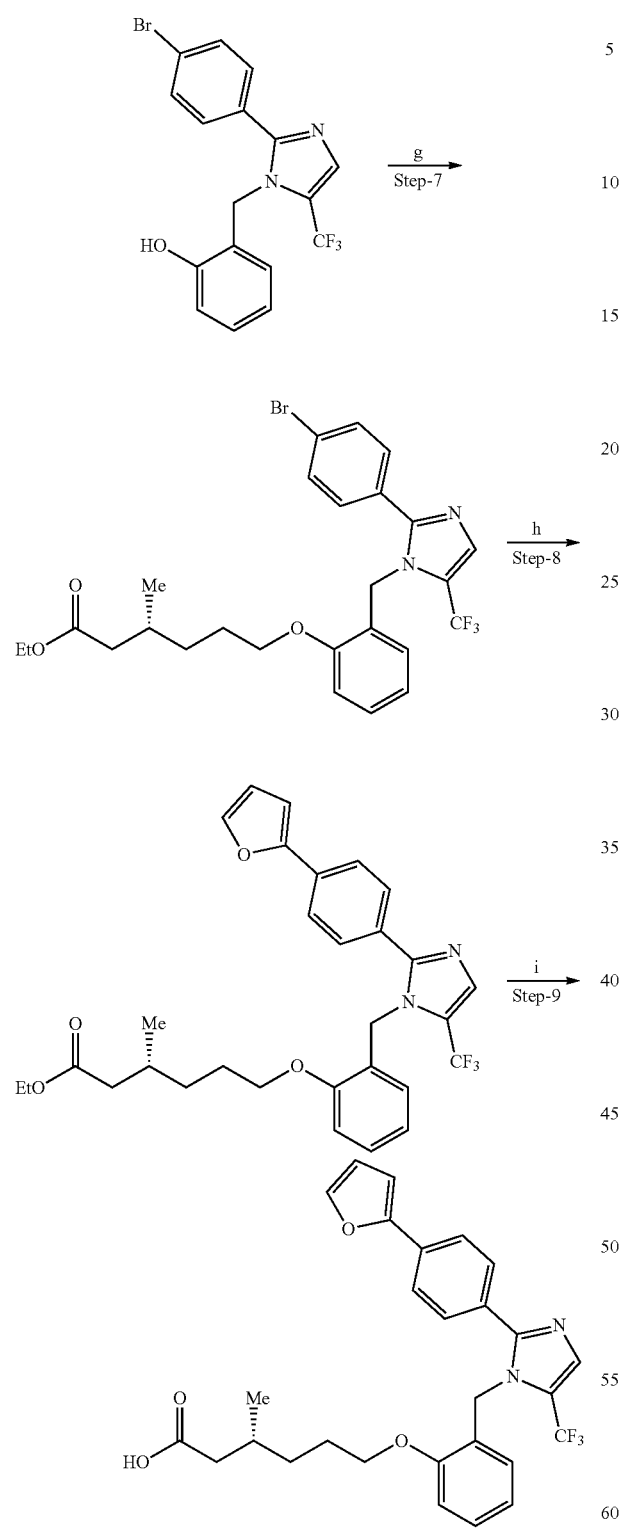

Reagents and conditions: a) Ethane-1,2-diamine, I₂, K₂CO₃, tert-BuOH, 85° C., 5 h; b) (Diacetoxyiodo)benzene, K₂CO₃, DMSO, 12 h; c) 2-Methoxybenzyl bromide, NaH (60% dispersion), DMF 0° C.-RT, 4 h; d) NIS, DMF, 70° C., 12 h; e) TMSCF₃, Ag₂CO₃, 1,10-phenanthroline, KF, CuI, 100° C., 12 h; f) BBr₃, DCM, 0° C.-RT, 3 h; g) Ethyl (3R)-6-bromo-3-methylhexanoate, tBuOK, DMF, RT, 12 h; h) Furan-2-boronic acid, Pd(PPh₃)₄, Na₂CO₃, DME, EtOH, H₂O, 90° C., 12 h; i) LiOH·H₂O, THF, EtOH, H₂O, RT, 12 h.

74

Step-1: Synthesis of 2-(4-bromophenyl)-4,5-dihydro-1H-imidazole

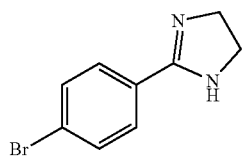 [SMILES: Brc1ccc(C2=NCCN2)cc1]

The title compound was synthesized from 4-bromobenzaldehyde (25.0 g, 131.52 mmol) following the experimental procedure described in step-7 of Example 2A.

Yield: 22.3 g (77.13%).

¹H NMR (400 MHz, DMSO-d₆): δ 7.73 (d, J=8.0 Hz, 2H), 7.62 (d, J=8.4 Hz, 2H), 3.59 (s, 4H), 3.48 (brs, 1H).

LCMS (ESI+, m/z): 225.0, 227.0 (M+H)⁺.

Step-2: Synthesis of 2-(4-bromophenyl)-1H-imidazole

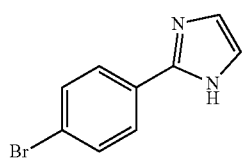 [SMILES: Brc1ccc(-c2ncc[nH]2)cc1]

The title compound was synthesized from 2-(4-bromophenyl)-4,5-dihydro-1H-imidazole (10.0 g, 44.44 mmol) following the experimental procedure described in step-8 of Example 2A.

Yield: 4.5 g (45.4%).

¹H NMR (300 MHz, DMSO-d₆): δ 12.6 (s, 1H), 7.85 (dd, J=9.0, 1.8 Hz, 2H), 7.62 (dd, J=6.6, 1.8 Hz, 2H), 7.13 (brs, 2H).

LCMS (ESI+, m/z): 223.1, 225.1 (M+H)⁺.

Step-3: Synthesis of 2-(4-bromophenyl)-1-(2-methoxybenzyl)-1H-imidazole

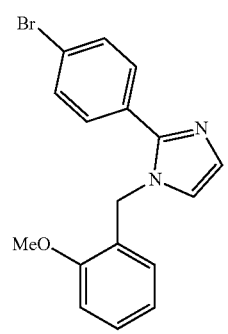 [SMILES: COc1ccccc1Cn1ccnc1-c1ccc(Br)cc1]

The title compound was synthesized from 2-(4-bromophenyl)-1H-imidazole (4.5 g, 20.17 mmol) following the experimental procedure described in step-9 of Example 2A.

Yield: 3.1 g (82.5%)

LCMS (ESI+, m/z): 342.9, 344.9 (M+H)+.

Step-4: Synthesis of 2-(4-bromophenyl)-5-iodo-1-(2-methoxybenzyl)-1H-imidazole

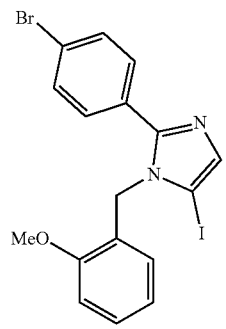 [SMILES: COc1ccccc1Cn1c(I)cnc1-c1ccc(Br)cc1]

The title compound was synthesized from 2-(4-bromophenyl)-1-(2-methoxybenzyl)-1H-imidazole (3 g, 8.746 mmol) following the experimental procedure described in step-10 of Example 2A.

Yield: 2.1 g (51.2%).

$^1$H NMR (300 MHz, CDCl$_3$): δ 7.47 (d, J=8.7 Hz, 2H), 7.33 (d, J=5.2 Hz, 2H), 7.31 (s, 1H), 6.92 (d, J=7.5 Hz, 2H), 6.53 (d, J=8.1 Hz, 2H), 5.18 (s, 2H), 3.86 (s, 3H).

LCMS (ESI+, m/z): 468.9, 470.9 (M+H)+.

Step-5: Synthesis of 2-(4-bromophenyl)-1-(2-methoxybenzyl)-5-(trifluoromethyl)-1H-imidazole

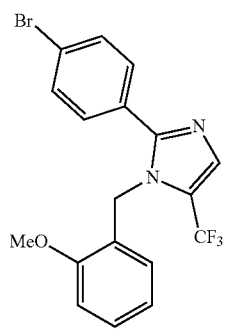

The title compound was synthesized from 2-(4-bromophenyl)-5-iodo-1-(2-methoxybenzyl)-1H-imidazole (0.5 g, 1.06 mmol) following the experimental procedure described in step-11 of Example 2A.

Yield: 0.22 g (50.2%).

$^1$H NMR (400 MHz, CDCl$_3$): δ 7.61 (s, 1H), 7.49 (d, J=6.3 Hz, 2H), 7.35 (d, J=6.3 Hz, 2H), 7.30-7.26 (m, 1H), 6.91-6.75 (m, 2H), 6.55 (d, J=5.7 Hz, 1H), 5.28 (s, 2H), 3.82 (s, 3H).

$^{19}$F NMR (400 MHz, CDCl$_3$): δ −63.21.

LCMS (ESI+, m/z): 411.1, 413.1 (M+H)+.

Step-6: Synthesis of 2-((2-(4-bromophenyl)-5-(trifluoromethyl)-1H-imidazol-1-yl)methyl)phenol

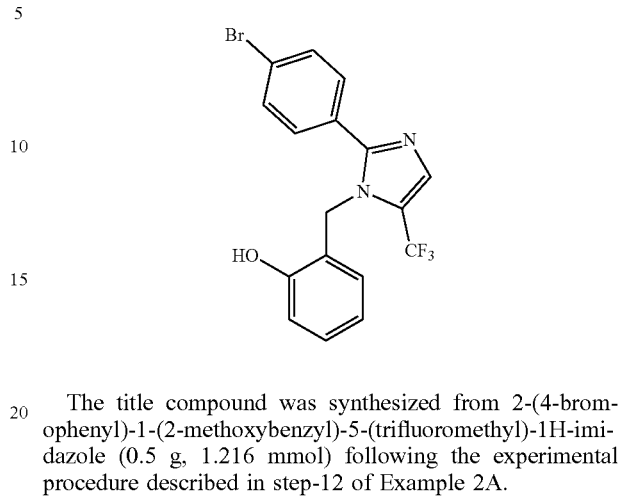

The title compound was synthesized from 2-(4-bromophenyl)-1-(2-methoxybenzyl)-5-(trifluoromethyl)-1H-imidazole (0.5 g, 1.216 mmol) following the experimental procedure described in step-12 of Example 2A.

Yield: 0.252 g, (52.08%).

$^1$H NMR (400 MHz, DMSO-d$_6$): δ 9.91 (s, 1H), 7.86 (s, 1H), 7.66 (d, J=8.4 Hz, 2H), 7.52 (d, J=8.4 Hz, 2H), 7.07 (t, J=7.2 Hz, 1H), 6.79 (d, J=8.0 Hz, 1H), 6.69 (t, J=7.6 Hz, 1H), 6.32 (d, J=7.2 Hz, 1H), 5.26 (s, 2H).

$^{19}$F NMR (400 MHz, DMSO-d$_6$): δ −58.01.

Step-7: Synthesis of ethyl (3R)-6-(2-((2-(4-bromophenyl)-5-(trifluoromethyl)-1H-imidazol-1-yl)methyl)phenoxy)-3-methylhexanoate

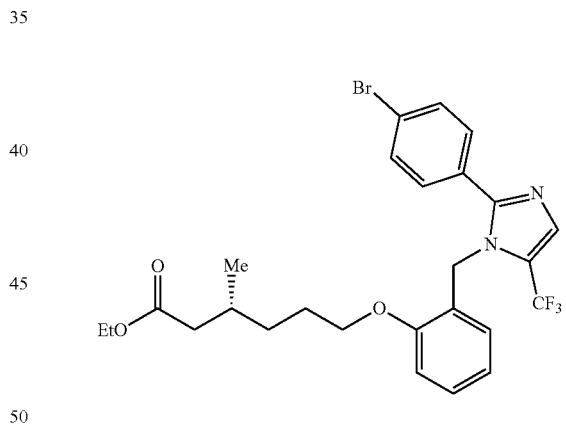

In a 100 mL round bottom flask, a stirred solution of 2-((2-(4-bromophenyl)-5-(trifluoromethyl)-1H-imidazol-1-yl)methyl)phenol (0.5 g, 1.259 mmol) in DMF (20 mL) was treated with KO$^t$Bu (0.435 g, 3.7 mmol) and ethyl (3R)-6-bromo-3-methylhexanoate (0.6 g, 2.518 mmol) at RT under nitrogen atmosphere. The resulting reaction mixture was stirred at RT for 2 h. Upon completion of the reaction (TLC), the reaction mixture quenched with ice cold water and extracted with ethyl acetate (3×25 mL). The combined organic extract was washed with brine, dried over anhydrous Na$_2$SO$_4$ and concentrated under reduced pressure. The residue obtained was purified by silica gel column chromatography (gradient elution, 15-30% EtOAc in hexanes) to afford the title compound.

Yield: 0.35 g (50.28%).

LCMS (ESI+, m/z): 553.3, 555.3 (M+H)+.

Step-8: Synthesis of ethyl (3R)-6-(2-((2-(4-(furan-2-yl)phenyl)-5-(trifluoromethyl)-1H-imidazol-1-yl)methyl)phenoxy)-3-methylhexanoate

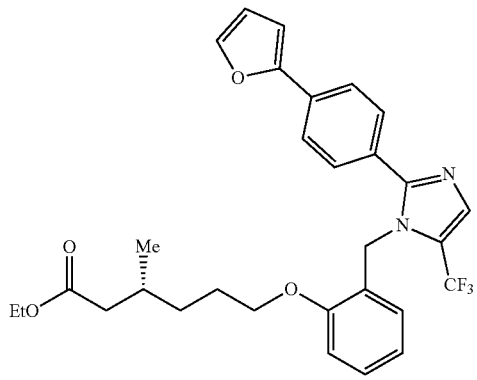 [SMILES: C[C@H](CCCOc1ccccc1Cn1c(C(F)(F)F)cnc1-c1ccc(-c2ccco2)cc1)CC(=O)O]

The title compound was synthesized from ethyl (3R)-6-(2-((2-(4-bromophenyl)-5-(trifluoromethyl)-1H-imidazol-1-yl)methyl)phenoxy)-3-methylhexanoate (0.2 g, 0.361 mmol) and furan-2-boronic acid (81 mg, 0.723 mmol) following the experimental procedure described in step-8 of Example 2H.

Yield: 0.1 g (51.28%).
$^{19}$F NMR (400 MHz, CDCl$_3$): δ –59.18.
LCMS (ESI+, m/z): 541.3 (M+H)$^+$.

Step-9: Synthesis of (3R)-6-(2-((2-(4-(furan-2-yl)phenyl)-5-(trifluoromethyl)-1H-imidazol-1-yl)methyl)phenoxy)-3-methylhexanoic acid

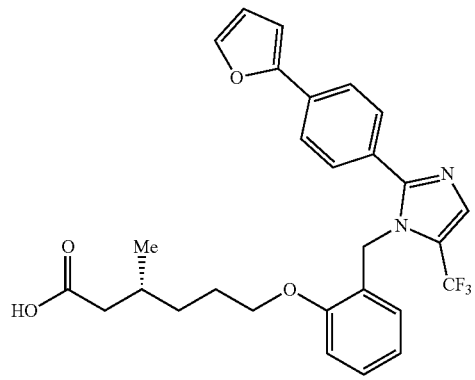

The title compound was synthesized from of ethyl (3R)-6-(2-((2-(4-(furan-2-yl)phenyl)-5-(trifluoromethyl)-1H-imidazol-1-yl)methyl)phenoxy)-3-methylhexanoate (0.25 g, 0.46 mmol) following the experimental procedure described in step-14 of Example 2A.

Yield: 0.135 g (56.96%).
$^1$H NMR (400 MHz, DMSO-d$_6$): δ 12.01 (s, 1H), 7.79 (s, 2H), 7.74 (d, J=8.4 Hz, 2H), 7.61 (d, J=8.8 Hz, 2H), 7.25 (t, J=8.0 Hz, 1H), 7.05 (d, J=3.2 Hz, 1H), 7.01 (d, J=8.0 Hz, 1H), 6.86 (t, J=8.0 Hz, 1H), 6.62 (s, 1H), 6.42 (d, J=6.8 Hz, 1H), 5.34 (s, 2H), 3.97 (t, J=6.0 Hz, 2H), 2.24-2.19 (m, 1H), 2.02-1.96 (m, 1H), 1.90-1.80 (m, 1H), 1.68-1.61 (m, 2H), 1.40-1.30 (m, 1H), 1.30-1.15 (m, 1H), 0.87 (d, J=6.4 Hz, 3H).

$^{19}$F NMR (400 MHz, DMSO-d$_6$): δ –57.83.
LCMS (ESI+, m/z): 512.6 (M+H)$^+$.
HPLC (210 nm): 94.62%.

What is claimed is:

1. A compound of Formula (I):

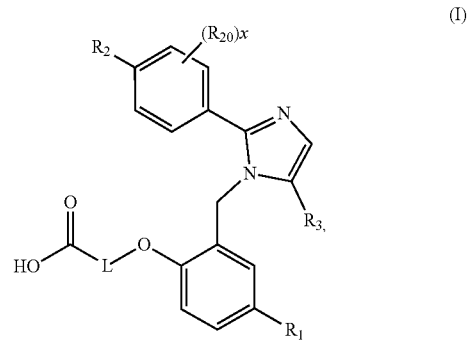

or a pharmaceutically acceptable salt thereof, wherein:

L is (CH$_2$)$_5$, which is optionally substituted by one methyl group;

R$^1$ is hydrogen, halogen, C$_1$-C$_4$-alkyl, C$_1$-C$_4$-haloalkyl, CN, C$_1$-C$_4$-alkoxy, C$_1$-C$_4$-haloalkoxy, or C$_3$-C$_6$-cycloalkyl;

R$^2$ is hydrogen, halogen, CN, C$_1$-C$_4$-alkyl, C$_1$-C$_4$-haloalkyl, C$_3$-C$_6$-cycloalkyl, C$_1$-C$_4$-alkoxy, C$_1$-C$_4$-haloalkoxy, S(C$_1$-C$_4$-alkyl), SO$_2$(C$_1$-C$_4$-alkyl), 5- or 6-membered heterocycle, aryl, 5-membered heteroaryl, ≡—R$^{2A}$, O(CH$_2$)$_m$R$^{2B}$NH(C$_1$-C$_4$-alkyl), N(C$_1$-C$_4$-alkyl)$_2$, or C(O)(C$_1$-C$_4$-alkyl), and wherein m is an integer having value of 1, 2, or 3;

x is an integer having a value of 0 or 1;

R$^{2A}$ and R$^{2B}$ are each independently C$_1$-C$_4$-alkyl, C$_1$-C$_4$-haloalkyl, or C$_3$-C$_6$-cycloalkyl;

R$^3$ is a C$_1$-C$_4$ haloalkyl, —NO$_2$, —CN, halogen, or C(O)O(C$_1$-C$_4$-alkyl); and each R$^{20}$ is independently halogen, C$_1$-C$_4$-alkyl, CN, or C$_1$-C$_4$-alkoxy.

2. The compound of claim 1, having the structure of any one of Formulas (Ia) or (Ib):

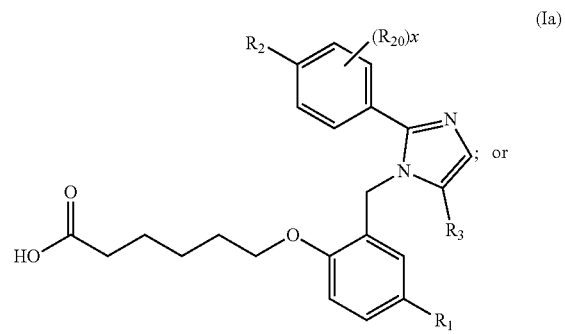

-continued

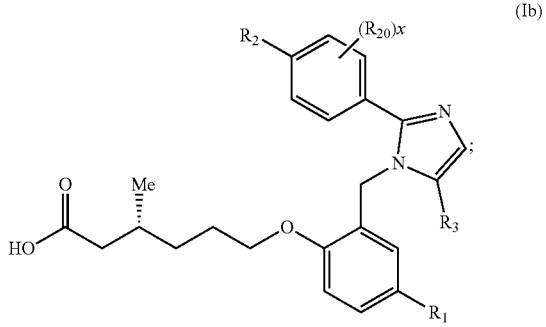

(Ib)

or a pharmaceutically acceptable salt thereof.

3. The compound of claim 2, having the structure of Formula (Ibb):

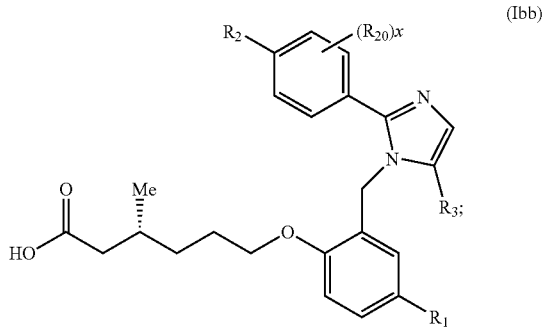

(Ibb)

or a pharmaceutically acceptable salt thereof.

4. The compound of claim 1 or a pharmaceutically acceptable salt thereof, where $R^3$ is halomethyl, CN or halogen.

5. The compound of claim 1 or a pharmaceutically acceptable salt thereof, wherein $R^3$ is $CF_3$, Cl or CN.

6. The compound of claim 5 or a pharmaceutically acceptable salt thereof, wherein $R^2$ is hydrogen, halogen, CN, $C_1$-$C_4$-alkyl, $C_1$-$C_4$ alkoxy, $C_1$-$C_4$-haloalkyl, $C_1$-$C_4$-haloalkoxy, $S(C_1$-$C_4$-alkyl).

7. The compound of claim 6 or a pharmaceutically acceptable salt thereof, wherein $R^2$ is H, halogen, CN, $CH_3$, halomethyl, halomethoxy, or methoxy; and $R^{20}$ is methyl or halogen.

8. The compound of claim 7 or a pharmaceutically acceptable salt thereof, wherein $R^2$ is H, F, Cl, CN, $CF_3$, $OCF_3$; and x is 0.

9. The compound of claim 8 or a pharmaceutically acceptable salt thereof, wherein $R^1$ is hydrogen.

10. The compound of claim 8 or a pharmaceutically acceptable salt thereof, wherein $R^1$ is hydrogen or fluoro.

11. The compound of claim 1 which is (3R)-6-(2-((2-(4-chlorophenyl)-5-(trifluoromethyl)-1H-imidazol-1-yl)methyl)phenoxy)-3-methylhexanoic acid, or a pharmaceutically acceptable salt thereof.

12. The compound of claim 1 which is (R)-6-(2-((5-chloro-2-(4-(trifluoromethyl)phenyl)-1H-imidazol-1-yl)methyl)phenoxy)-3-methylhexanoic acid, or a pharmaceutically acceptable salt thereof.

13. The compound of claim 1 which is (R)-6-(2-((2-(4-cyanophenyl)-5-(trifluoromethyl)-1H-imidazol-1-yl)methyl)phenoxy)-3-methylhexanoic acid or a pharmaceutically acceptable salt thereof.

14. The compound of claim 1 which is (3R)-3-methyl-6-(2-((5-(trifluoromethyl)-2-(4-(trifluoromethyl)phenyl)-1H-imidazol-1-yl)methyl)phenoxy) hexanoic acid or a pharmaceutically acceptable salt thereof.

15. A pharmaceutical composition comprising a pharmaceutically acceptable carrier or excipient and the compound of claim 1, or a pharmaceutically acceptable salt thereof.

16. A method of treating a disease or condition in a subject, comprising administering to the subject in need thereof a therapeutically effective amount of one or more compounds of claim 1, or a pharmaceutically acceptable salt thereof, or a pharmaceutical composition comprising a pharmaceutically acceptable carrier or excipient and the compound of claim 1, or a pharmaceutically acceptable salt thereof, and wherein the disease or condition is nonalcoholic steatohepatitis (NASH), dvslipidemia, or type 2 diabetes.

17. A method of treating a disease or condition in a subject, comprising administering to the subject in need thereof a therapeutically effective amount of a compound of claim 1, or a pharmaceutically acceptable salt thereof, or a pharmaceutical composition comprising a pharmaceutically acceptable carrier or excipient and the compound of claim 1, or a pharmaceutically acceptable salt thereof, and wherein the disease or condition is Duchene muscular dystrophy (DMD), acute renal failure, or chronic fatigue syndrome.

18. A method of treating a disease or condition in a subject, comprising administering to the subject in need thereof a therapeutically effective amount of a compound of claim 1, or a pharmaceutically acceptable salt thereof, or a pharmaceutical composition comprising a pharmaceutically acceptable carrier or excipient and the compound of claim 1, or a pharmaceutically acceptable salt thereof, and wherein the disease or condition is Alpers's Disease, CPEO-Chronic progressive external ophthalmoplegia, Kearns-Sayra Syndrome (KSS), Leber Hereditary Optic Neuropathy (LHON), MELAS-Mitochondrial myopathy, encephalomyopathy, lactic acidosis, and stroke-like episodes, MERRF-Myoclonic epilepsy and ragged-red fiber disease, NARP-neurogenic muscle weakness, ataxia, and retinitis pigmentosa, or Pearson Syndrome.

* * * * *

UNITED STATES PATENT AND TRADEMARK OFFICE
CERTIFICATE OF CORRECTION

PATENT NO. : 11,358,954 B2
APPLICATION NO. : 16/092232
DATED : June 14, 2022
INVENTOR(S) : Bharat Lagu and Ramesh Senaiar It is certified that error appears in the above-identified patent and that said Letters Patent is hereby corrected as shown below:

In the Claims

In Claim 1, Column 78, Line numbers 35-37, please delete the phrase "5- or 6 - membered heterocycle, aryl, 5 - membered heteroaryl".

Signed and Sealed this
Sixth Day of September, 2022

Katherine Kelly Vidal
*Director of the United States Patent and Trademark Office*